US008499759B2

(12) United States Patent
DiBlasi et al.

(10) Patent No.: US 8,499,759 B2
(45) Date of Patent: Aug. 6, 2013

(54) BROAD-BAND, LOW FREQUENCY, HIGH-AMPLITUDE, LONG TIME DURATION, OSCILLATING AIRWAY PRESSURE BREATHING APPARATUS AND METHOD UTILIZING BUBBLES

(75) Inventors: Robert M. DiBlasi, Snoqualmie, WA (US); Jay C. Zignego, Vancouver, WA (US); Thomas N. Hansen, Mercer Island, WA (US); Charles V. Smith, Mercer Island, WA (US); Peter Richardson, Shoreline, WA (US)

(73) Assignee: Seattle Children's Hospital, Seattle, WA (US)

( * ) Notice: Subject to any disclaimer, the term of this patent is extended or adjusted under 35 U.S.C. 154(b) by 518 days.

(21) Appl. No.: 12/899,177

(22) Filed: Oct. 6, 2010

(65) Prior Publication Data

US 2011/0073112 A1   Mar. 31, 2011

Related U.S. Application Data

(63) Continuation of application No. PCT/US2009/039957, filed on Apr. 8, 2009.

(60) Provisional application No. 61/044,002, filed on Apr. 10, 2008, provisional application No. 61/150,670, filed on Feb. 6, 2009.

(51) Int. Cl.
*A62B 7/00* (2006.01)
*A62B 9/00* (2006.01)

(52) U.S. Cl.
USPC .................. 128/204.18; 128/200.24

(58) Field of Classification Search
USPC ............. 128/204.21, 205.23, 200.24, 204.18
See application file for complete search history.

(56) References Cited

U.S. PATENT DOCUMENTS

| 3,710,780 A | 1/1973 | Milch |
| 3,811,671 A | 5/1974 | Turnbull |

(Continued)

FOREIGN PATENT DOCUMENTS

| EP | 0 513 712 A1 | 11/1992 |
| WO | WO 2005/035019 A2 | 4/2005 |

OTHER PUBLICATIONS

Anmari, Amer et al., "Bubble nasal CPAP manual" Riyadh Al-Kharj Hospital Programme Neonatal intensive care 2005, XP-002541077, Dec. 31, 2005.

(Continued)

*Primary Examiner* — Justine Yu
*Assistant Examiner* — Rachel Young
(74) *Attorney, Agent, or Firm* — Knobbe, Martens, Olson & Bear, LLP

(57) ABSTRACT

It has been discovered that high amplitude, low frequency, broadband spectrum pressure oscillations of sufficient time duration can help stabilize lung volumes and improve gas exchange in a patient receiving ventilation assistance by helping to recruit and stabilize alveoli. A novel device is presented which can produce pressure oscillations having high amplitudes, a low broad-band frequency spectrum and long time duration. Additionally, the device can maintain a patient's mean airway pressure at one or more controlled levels. The device can control the oscillatory amplitude, frequency range and composition, time duration, and mean airway pressure levels by adjusting certain device parameters, such as the angle and depth of the device in a fluid. A device and mechanical system for remotely adjusting and measuring the angle of the device in a fluid are also disclosed. Furthermore, a device and system are disclosed that can deliver pressure oscillations having high amplitudes, a low broad-band frequency spectrum, long time duration, and multiple mean airway inspiratory and expiratory pressure levels. The device and system also provide means for controlling respiration timing in a patient, including: breaths per minute, inspiratory time, and the ratio of inspiratory to expiratory time.

61 Claims, 29 Drawing Sheets

U.S. PATENT DOCUMENTS

| | | | |
|---|---|---|---|
| 6,805,120 | B1 | 10/2004 | Jeffrey et al. |
| 7,077,154 | B2 | 7/2006 | Jacobs et al. |
| 2004/0069304 | A1 | 4/2004 | Jam |
| 2006/0078506 | A1 | 4/2006 | Niven et al. |
| 2009/0056719 | A1* | 3/2009 | Newman, Jr. ............ 128/204.18 |

OTHER PUBLICATIONS

Chan, Km et al., "The Use of Bubble CPAP in Premature Infants: Local Experience" Hong Kong Journal of Paediatrics, Dec. 31, 2007, pp. 86-92, vol. 12, No. 2.

Koyamaibole, Lanieta et al., "An Evaluation of Bubble-CPAP in a Neonatal Unit in a Developing Country: Effective Respiratory Support That Can Be Applied By Nurses" Journal of Tropical Pediatrics, 2006, pp. 249-253, vol. 52, No. 4.

Lee, Kyong-Soon et al., "A Comparison of Underwater Bubble Continuous Positive Airway Pressure with Ventilator-Derived Continuous Positive Airway Pressure in Premature Neonates Ready for Extubation" Biol Neonate, 1998, pp. 69-75, vol. 73.

Narendran, Vivek et al., "Early Bubble CPAP and Outcomes in ELBW Preterm Infants" Journal of Perinatology, 2003, pp. 195-199, vol. 23.

Nekvasil, R. et al., "High Frequency Oscillation, "Bubble" Ventilation during the Neonatal Period" Cs. Pediat., 1992, pp. 465-470, vol. 47, No. 8—Abstract.

Nekvasil, R. et al., "High Frequency Oscillation, "Bubble" Ventilation during the Neonatal Period" Cs. Pediat., 1992, pp. 465-470, vol. 47, No. 8.

International Search Report for PCT/US2009/039957 dated Aug. 31, 2009.

Pillow, J. Jane et al., "Bubble CPAP: Is the Noise Important? An In Vitro Study" Pediatric Research, 2005, pp. 826-830, vol. 57, No. 6.

European Search Report for EP 11161162.0 dated Jun. 8, 2011.

* cited by examiner

BROAD-BAND, LOW FREQUENCY, HIGH-AMPLITUDE, LONG TIME DURATION, OSCILLATING AIRWAY PRESSURE BREATHING APPARATUS AND METHOD UTILIZING BUBBLES

CROSS-REFERENCE TO RELATED APPLICATIONS

This application is a continuation of and claims the benefit of priority to International Application PCT/US2009/039957, filed Apr. 8, 2009, which designated the United States and was published in English, and claims priority to U.S. provisional Application No. 61/044,002, filed Apr. 10, 2008 and U.S. Provisional Application No. 61/150,670, filed Feb. 6, 2009, the disclosures of which are hereby expressly incorporated by reference in their entireties.

FIELD OF THE INVENTION

Embodiments described herein concern compositions and methods that assist gas exchange and stabilize lung volume in a host. Some embodiments relate to compositions and methods that employ an angled conduit submersed in a liquid, which promotes efficient gas exchange and stabilizes lung volume when low frequency, high-amplitude oscillating pressure waves are produced.

BACKGROUND OF THE INVENTION

Babies born before 37 completed weeks of pregnancy are called premature. While many of these babies do well, some go on to have lifelong health problems. Approximately 60,000 infants with birth weights under 1500 g (about 1.5% of all newborns) are born in the United States each year and about 20% of these infants develop chronic lung disease (Births: final data for 2003. Hyattsville, Md.: National Center for Health Statistics, Centers for Disease Control and Prevention, 2005).

Severely premature infants have underdeveloped lungs and insufficient surfactant to maintain stable lung volumes. This condition may lead to Respiratory Distress Syndrome (also called hyaline membrane disease) and progress to chronic lung disease, a major contributor to preterm infant morbidity and mortality. Chronic Lung disease in the premature is associated with infants requiring mechanical ventilation via endotracheal tube.

Continuous positive airway pressure (CPAP) has been a mainstay for the treatment of preterm infants in respiratory distress for many years. CPAP provides maintenance of the mean airway pressure throughout the breath cycle to help open and maintain unstable alveoli, which are typically underdeveloped and surfactant deficient. CPAP is frequently applied to patients using commercially available mechanical ventilators. CPAP can be applied to infants either nasally or via an endotracheal tube. Unfortunately, the vast majority of mechanical ventilators are not designed to be used with nasal prongs.

The purchase and maintenance costs of mechanical ventilators render them impractical for use as CPAP devices. CPAP via endotracheal tube is known to increase chronic lung disease in preterm infants. Bronchopulmonary dysplasia makes up the majority of infants with chronic lung disease. Mechanical ventilator devices are complex to operate, requiring a substantial investment to acquire and maintain the devices, as well as, to train the care givers to properly administer the treatment. Importantly, mechanical ventilator devices do not provide broadband oscillations in airway pressure. The high frequency oscillatory ventilator systems described in U.S. Pat. Nos. 4,805,612 4,481,944 and 5,752,506, for example, are capable of delivering large oscillations in airway pressure. However, these devices can only deliver large oscillations in airway pressure at a single frequency (selected by the operator).

Conventional Bubble CPAP (B-CPAP) is thought to improve ventilation in premature infants. By bubbling mechanical ventilator CPAP gases through a fluid with a simple conduit that is submersed vertically in the fluid, B-CPAP causes an infant's chest to vibrate at high frequencies such that the infant breathes at a lower respiratory rate than an infant receiving simple ventilator CPAP. Pillow, et al. (6 (*Pediatr Res* 57: 826-830, 2005)) demonstrated in a mechanical lung model that B-CPAP creates oscillations in airway pressure with predominant frequencies in the ranges of about 10 to 20 Hz and 40 to 100 Hz, for example. In another study, Pillow et al. (7, Am J Respir Crit Care Med Vol 176. pp 63-69, 2007) showed that B-CPAP applied to preterm lambs breathing spontaneously had improved oxygen levels and tended to reach stable lung volumes at lower airway pressures than lambs receiving CPAP generated by a mechanical ventilator. The B-CPAP device used in the studies by Pillow et al., is described in U.S. Pat. No. 6,805,120 entitled "Breathing Assistance Apparatus." Pillow et al. attributed the improved lung stability to the broadband frequency spectrum of oscillations in airway pressure produced by CPAP gas bubbles exiting the vertically oriented conduit submersed in water. The device described by Pillow et al., however, produces small amplitude pressure oscillations that are delivered at a relatively high range of frequencies to the airway of the host, resulting in low amplitude and low time duration pressure waves that do not deliver sufficient gas to the host's lungs.

Nekvasil, et. al., (1992 Čs. Pediat., 47, 8:465-470) demonstrated that high frequency oscillations in airway pressure can be created using a B-CPAP device comprising a glass funnel placed horizontally under a fluid. Placed in this configuration the device provides higher amplitude oscillations in airway pressure, but at a narrow frequency band with low time duration. Thus, although the amplitude of oscillations is high for one frequency (about 1.1 Hz), the volume of gas delivered to the patient is still inadequate because the time duration of the pressure wave is not long enough to push sufficient amounts of gas into the patient's lungs.

Presently, in many neonatal intensive care units, preterm infants requiring respiratory assistance are place on nasal B-CPAP. If the infants fail to meet established gas exchange criteria, they are intubated and placed on mechanical ventilation. A device is needed that can maintain gas exchange and alveolar stability in infants failing B-CPAP and that reduces the number of infants requiring intubation and mechanical ventilation. A respiratory assistance device is needed that can reduce the work of breathing of patients and stabilize the lungs by maintaining mean airway pressures throughout the breath cycle. It is also desirable to provide better gas exchange than that provided by single frequency ventilators, B-CPAP, or funnel B-CPAP devices. For infants requiring mechanical ventilation, a device is need that can be applied via either nasal prongs or endotracheal tube at low peak airway pressures. Additionally, it is desirable to provide a respiratory assistance device that is simple in design, easy to operate, and inexpensive to manufacture.

SUMMARY OF THE INVENTION

It has been discovered that relatively high amplitude, low frequency, broadband spectrum pressure oscillations of sufficient time duration can help stabilize lung volumes and improve gas exchange in a patient receiving ventilation assistance. Embodiments described herein can produce pressure oscillations having high amplitudes, a low broad-band frequency spectrum and long time duration. Additionally, the embodiments described herein maintain a patient's mean airway pressure at one or more controlled levels. In application, a user can control the oscillatory amplitude, frequency range and composition, time duration, and mean airway pressure levels by adjusting certain device parameters, such as the angle and depth of the device in a fluid. Some embodiments also include a mechanical system for remotely adjusting and measuring the angle of the device in a fluid. Additional embodiments include devices and systems that deliver pressure oscillations having high amplitudes, a low broad-band frequency spectrum, long time duration, and multiple mean airway inspiratory and expiratory pressure levels. These embodiments also have features that allow a user to select and modulate respiration timing in a patient, including: breaths per minute, inspiratory time, and the ratio of inspiratory to expiratory time.

Low frequency, broad-band, high amplitude and long duration oscillations in airway pressure are beneficial for patients that have difficulty removing pulmonary secretions. The embodiments described herein can be used to ventilate patients of all ages, including adults. Examples of patients that will benefit from the technology described herein include, but are not limited to: patients with bronchiolitis, pneumonia, cystic fibrosis, neonates with meconium aspiration syndrome, congenital diaphragmatic hernia, and congenital heart disease, premature infants with lung disease or larger infants or adults that require respiratory assistance during surgery and post operative care. Additionally, several embodiments described herein are useful in remote clinical settings, in clinical facilities that do not have access to mechanical ventilators, or in clinical settings that lack power such as catastrophic disaster sites.

In one embodiment, a pressure regulating breathing assistance apparatus having a pressurized gas source, a fluid-filled container and a conduit is provided. The conduit includes proximal and distal ends. The proximal end is adapted for connection to the pressurized gas source and to a patient interface intermediate the proximal and distal ends of the conduit. The distal end of the conduit has at least one peak inspiratory pressure control conduit that is configured to be submerged in the fluid-filled container at varying depths. The distal end of the conduit also has at least one positive end-expiratory pressure control conduit that is also configured to be submerged in the body of fluid at varying depths. The distal end of the conduit also has a valve intermediate the at least one peak inspiratory pressure control conduit and the at least one positive end-expiratory pressure control conduit.

In some embodiments, the distal end of the at least one peak inspiratory pressure control conduit and/or the at least one positive end-expiratory pressure control conduit has any angle except 0 and 90 degrees with respect to a vertical axis so long as the device is configured to produce a high amplitude, low frequency broadband oscillating pressure wave having more than 50% of its average power spectra occur below about 7 Hz when the bias gas flow is at least 2 L/min in a model test lung system comprising a hermetically sealed silastic lung within a calibrated plethysmograph. In other embodiments, the distal end of the positive end-expiratory pressure control conduit is angled greater than 90 degrees with respect to a vertical axis. In further embodiments, the distal end of the peak inspiratory pressure control conduit and/or the end-expiratory pressure control conduit is angled greater than or equal to between about 91-170 degrees, between about 95-165 degrees, between about 100-160 degrees, between about 105-155 degrees, between about 110-150 degrees, between about 115-145 degrees, between about 120-140 degrees, between about 125-135 degrees, between about 130-140 degrees, or about 135 degrees with respect to a vertical axis. In one particular embodiment, the distal end of the peak inspiratory pressure control conduit and/or the end-expiratory pressure control conduit is angled to about 135 degrees with respect to a vertical axis.

In certain embodiments, the distal end of the peak inspiratory pressure control conduit and/or the end-expiratory pressure control conduit is substantially circular having an inside diameter of between about 1-3 cm, between about 1.2-2.0 cm, between about 1.3-1.8 cm, between about 1.4-1.6 cm, or about 1.5 cm.

In further embodiments, the angled portion of the distal end of the peak inspiratory pressure control conduit and/or the end-expiratory pressure control conduit has a length of between about 5-12 cm, between about 6-11 cm, between about 7-10 cm, between about 8-9.5 cm, or about 9 cm.

In other embodiments, the distal end of the peak inspiratory pressure control conduit and/or the end-expiratory pressure control conduit is submerged to a depth of about between 3-200 cm, between about 5-11 cm, about 5 cm, about 7 cm, about 9 cm, or about 11 cm.

In yet other embodiments, the fluid has a density of between about 0.8-1.1 g/cm3 at 20° C., between about 0.85-1.05, between about 0.9-1.0 g/cm3 at 20° C., or about 1.0 g/cm3 at 20° C. In one particularly preferred embodiment, the fluid is water.

In preferred embodiments, the peak inspiratory pressure control conduit is configured to produce an oscillating pressure wave having more than 50% of its average power spectra occur below about 7 Hz when the bias flow of gas is at least 2 L/min in a model test lung system comprising a hermetically sealed silastic lung within a calibrated plethysmograph. In other preferred embodiments, the peak inspiratory pressure control conduit is configured to produce airway pressure oscillation frequencies of between about 1-10 Hz, between about 2-9 Hz, between about 2-7 Hz, or between about 2-5 Hz when the bias flow is 6 L/min in a model test lung system comprising a hermetically sealed silastic lung within a calibrated plethysmograph. In a particularly preferred embodiment, the peak inspiratory pressure control conduit is configured to deliver an average volume of gas greater than about 3.0 ml when the bias flow of gas is 8 L/min in a model test lung system comprising a hermetically sealed silastic lung within a calibrated plethysmograph.

In some embodiments, a conduit swivel member is used at the distal end of the conduit to adjust the angle of the distal end of the conduit with respect to a vertical axis. The conduit swivel member can also have a plurality of marks that indicate the angle of the distal end of the conduit with respect to the vertical axis. The conduit swivel member can be automated such that a user can manually or automatically adjust the angle of said distal end of said conduit with respect to the vertical axis. Additionally, a computer can also be used to operate the swivel member upon user instruction or programmed executable instructions to thereby automatically adjust the angle of the distal end of the conduit with respect to the vertical axis.

In one embodiment, a breathing assistance apparatus is provided having a pressurized gas source, a container holding a liquid, and a conduit. The conduit has proximal and distal ends, the proximal end being adapted for connection to the pressurized gas source, and the distal end of the conduit being configured to be submerged in the liquid. The conduit is also adapted for connection to a patient interface intermediate the proximal and distal ends of the conduit and the distal end of the conduit is angled greater than 90 degrees with respect to a vertical axis. In other embodiments, the distal end of the conduit is angled greater than or equal to between about 91-170 degrees, between about 95-165 degrees, between about 100-160 degrees, between about 105-155 degrees, between about 110-150 degrees, between about 115-145 degrees, between about 120-140 degrees, between about 125-135 degrees, between about 130-140 degrees, or about 135 degrees with respect to a vertical axis. In one particularly preferred embodiment, the distal end of the conduit is angled to about 135 degrees with respect to a vertical axis.

In certain embodiments, the distal end of the conduit is substantially circular having an inside diameter of between about 1-3 cm, between about 1.2-2.0 cm, between about 1.3-1.8 cm, between about 1.4-1.6 cm, or about 1.5 cm.

In further embodiments, the angled portion of the distal end of the conduit has a length of between about 5-12 cm, between about 6-11 cm, between about 7-10 cm, between about 8-9.5 cm, or about 9 cm.

In some embodiments, the distal end of the conduit is submerged to a depth of about between 3-200 cm, between about 5-11 cm, about 5 cm, about 7 cm, about 9 cm, or about 11 cm.

In certain embodiments, the fluid has a density of between about 0.8-1.1 g/cm3 at 20° C., between about 0.85-1.05, between about 0.9-1.0 g/cm3 at 20° C., or about 1.0 g/cm3 at 20° C. In a particularly preferred embodiment, the fluid is water.

In preferred embodiments, the conduit is configured to produce an oscillating pressure wave having more than 50% of its average power spectra occur below about 7 Hz when the bias flow of gas is 2 L/min in a model test lung system comprising a hermetically sealed silastic lung within a calibrated plethysmograph. In other preferred embodiments, the conduit is configured to produce an oscillating pressure wave having more than 50% of its average power spectra occur between about 2-5 Hz when the bias flow of gas is 2 L/min and 1-9 Hz when the bias flow of gas is 12 L/min in a model test lung system comprising a hermetically sealed silastic lung within a calibrated plethysmograph. In one particularly preferred embodiment, the conduit is configured to produce airway pressure oscillation frequencies of between about 1-10 Hz, between about 2-9 Hz, between about 2-7 Hz, or between about 2-5 Hz when the bias flow is 6 L/min in a model test lung system comprising a hermetically sealed silastic lung within a calibrated plethysmograph. In another particularly preferred embodiment, the conduit is configured to deliver an average volume of gas of about 4.0 ml when the bias flow of gas is 8 L/min in a model test lung system comprising a hermetically sealed silastic lung within a calibrated plethysmograph.

In some embodiments, the breathing assistance apparatus has a conduit swivel member at the distal end of the conduit that is configured to adjust the angle of the distal end of the conduit with respect to a vertical axis. The conduit swivel member can also have a plurality of marks that indicate the angle of the distal end of said conduit with respect to the vertical axis. Additionally, the conduit swivel member can also be automated such that a user or a computer can automatically adjust the angle of the distal end of the conduit with respect to the vertical axis. And in certain embodiments, the gas source is a gas compressor or a mechanical or electromechanical ventilator.

In one embodiment, a bubble continuous positive airway pressure (B-CPAP) device is provided having a pressurized gas source, a container holding a liquid and a conduit. The conduit has proximate and distal ends. The proximal end is adapted for connection to the pressurized gas source. The conduit is also adapted for connection to a patient interface intermediate the proximal and distal ends. The distal end of the conduit is configured to be submerged in the liquid at varying depths and the distal end of the conduit has a conduit swivel member that is configured to adjust the angle of the distal end of the conduit with respect to a vertical axis. The conduit swivel member can have a plurality of marks that indicate the angle of the distal end of the conduit with respect to the vertical axis. Furthermore, the conduit swivel member can be automated such that a user, a computer, a processor or a machine can automatically adjust the angle of the distal end of the conduit with respect to the vertical axis. For example, a computer can be configured to operate the conduit swivel member upon user instruction to automatically adjust the angle of the distal end of the conduit with respect to a vertical axis. In some embodiments, the pressurized gas source comprises a gas compressor or a mechanical or electromechanical ventilator.

In another embodiment, a bubble continuous positive airway pressure (B-CPAP) device is provided having a pressurized gas source, a container holding a liquid and a conduit. The conduit has proximate and distal ends. The proximal end is adapted for connection to the pressurized gas source. The conduit is also adapted for connection to a patient interface intermediate the proximal and distal ends. The distal end of the conduit is submerged in the liquid and configured to produce an oscillating pressure wave having more than 50% of its average power spectra occur between about 2-5 Hz when the bias flow of gas is 2 L/min and 1-9 Hz when the bias flow of gas is 12 L/min in a model test lung system comprising a hermetically sealed silastic lung within a calibrated plethysmograph.

In further embodiments, a bubble continuous positive airway pressure (B-CPAP) device is provided having a pressurized gas source, a container holding a liquid and a conduit. The conduit has proximate and distal ends. The proximal end is adapted for connection to the pressurized gas source. The conduit is also adapted for connection to a patient interface intermediate the proximal and distal ends. The distal end of the conduit is submerged in the liquid and configured to deliver an average volume of gas of about 4.0 ml when the bias flow of gas is 8 L/min in a model test lung system comprising a hermetically sealed silastic lung within a calibrated plethysmograph.

In one embodiment, a method is disclosed for increasing the volume of gas delivered to a subject by a bubble continuous positive airway pressure (B-CPAP) device by providing a any of the breathing assistance apparatuses disclosed herein; adjusting the angle of the distal end of the conduit of the breathing assistance apparatus to greater than 90 degrees with respect to a vertical axis; releasing gas from the pressurized gas source into the breathing assistance apparatus, or B-CPAP device; and delivering the gas to the subject. In some embodiments, the distal end of the conduit is adjusted to an angle greater than or equal to between about 91-170 degrees, between about 95-165 degrees, between about 100-160 degrees, between about 105-155 degrees, between about 110-150 degrees, between about 115-145 degrees, between about 120-140 degrees, between about 125-135 degrees, between about 130-140 degrees, or about 135 degrees with respect to a vertical axis. In a particularly preferred embodiment, the distal end of the conduit is adjusted to an angle of about 135 degrees with respect to a vertical axis. In still other embodiments, the distal end of the conduit is adjusted to any angle, except 0 and 90 degrees, so long as the breathing assistance apparatus is configured to produce an oscillating pressure wave having more than 50% of its average power spectra occur below about 7 Hz when the bias flow of gas is at least 2 L/min in a model test lung system comprising a hermetically sealed silastic lung within a calibrated plethysmograph.

In another embodiment, a breathing assistance apparatus is provided having a pressurized gas source, a container holding a liquid, and a conduit. The conduit has proximal and distal ends, the proximal end being adapted for connection to the pressurized gas source, and the distal end of the conduit being configured to be submerged in the liquid. The conduit is also adapted for connection to a patient interface intermediate the proximal and distal ends of the conduit. The distal end of the conduit can have any angle with respect to a vertical axis, except 0 and 90 degrees, so long as the conduit is configured to produce an oscillating pressure wave having more than 50% of its average power spectra occur below about 7 Hz when the bias flow of gas is at least 2 L/min in a model test lung system comprising a hermetically sealed silastic lung within a calibrated plethysmograph.

In another embodiment, a breathing assistance apparatus is provided having a pressurized gas source, a container holding a liquid, and a conduit. The conduit has proximal and distal ends, the proximal end being adapted for connection to the pressurized gas source, and the distal end of the conduit being configured to be submerged in the liquid. The conduit is also adapted for connection to a patient interface intermediate the proximal and distal ends of the conduit. The distal end of the conduit can have any angle with respect to a vertical axis, except 0 and 90 degrees, so long as the conduit is configured to produce an oscillating pressure wave having more than 50% of its average power spectra occur between about 2-5 Hz when the bias flow of gas is 2 L/min and 1-9 Hz when the bias flow of gas is 12 L/min in a model test lung system comprising a hermetically sealed silastic lung within a calibrated plethysmograph.

In yet another embodiment, a breathing assistance apparatus is provided having a pressurized gas source, a container holding a liquid, and a conduit. The conduit has proximal and distal ends, the proximal end being adapted for connection to the pressurized gas source, and the distal end of the conduit being configured to be submerged in the liquid. The conduit is also adapted for connection to a patient interface intermediate the proximal and distal ends of the conduit. The distal end of the conduit can have any angle with respect to a vertical axis, except 0 and 90 degrees, so long as the conduit is configured to produce airway pressure oscillation frequencies of between about 1-10 Hz, between about 2-9 Hz, between about 2-7 Hz, or between about 2-5 Hz when the bias flow is 6 L/min in a model test lung system comprising a hermetically sealed silastic lung within a calibrated plethysmograph.

In further embodiments, a breathing assistance apparatus is provided having a pressurized gas source, a container holding a liquid, and a conduit. The conduit has proximal and distal ends, the proximal end being adapted for connection to the pressurized gas source, and the distal end of the conduit being configured to be submerged in the liquid. The conduit is also adapted for connection to a patient interface intermediate the proximal and distal ends of the conduit. The distal end of the conduit can have any angle with respect to a vertical axis, except 0 and 90 degrees, so long as the conduit is configured to deliver an average volume of gas of about 4.0 ml when the bias flow of gas is 8 L/min in a model test lung system comprising a hermetically sealed silastic lung within a calibrated plethysmograph.

DETAILED DESCRIPTION OF THE PREFERRED EMBODIMENTS

Embodiments described herein provide pressure oscillations having high amplitudes, a low-broadband frequency spectrum, and sufficient time duration to a patient's airway to help stabilize lung volumes and improve gas exchange. Some embodiments, for example, maintain a patient's mean airway pressure at one or more controlled levels during spontaneous breathing and apnea. Some embodiments allow a user to control the oscillatory amplitude, frequency range and composition, time duration, and mean airway pressure levels by adjusting certain device parameters, such as the bias flow, angle and depth of the device in a fluid. In certain embodiments, the device comprises a mechanical system for remotely adjusting and measuring the angle of the device in a fluid. In other embodiments, the device and system can deliver pressure oscillations having high amplitudes, a low broad-band frequency spectrum, long time duration, and multiple mean airway inspiratory and expiratory pressure levels. Some embodiments can also provide means for controlling respiration timing in a patient, including: breaths per minute, time to inspiration and the ratio of inspiratory to expiratory time.

Figure 1:
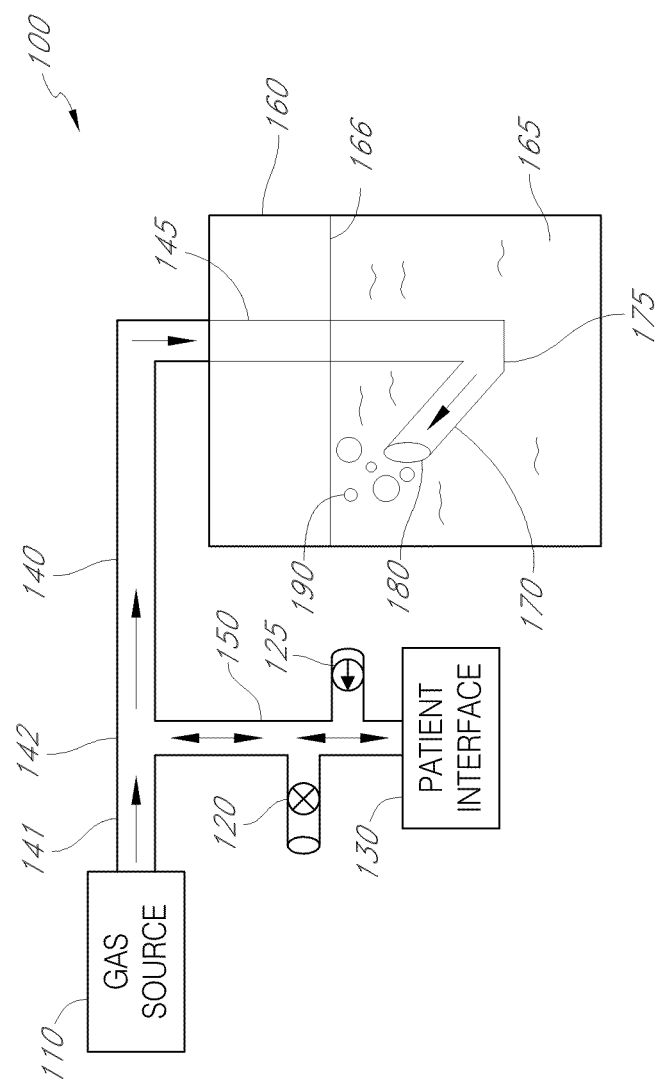
FIG. 1 depicts a patient ventilation system utilizing a conduit submerged in fluid and configured to modulate airway pressures.

FIG. 1 illustrates a patient ventilation system 100 utilizing a bubbler 170 (also referred to herein as an "angled portion" of the submerged conduit, a "bubbleator," or a "High Amplitude Bubbler" (HAB)) submerged in a fluid 165 and configured to modulate the frequency and amplitudes of airway pressures in a patient (not shown) attached to the device at the patient interface 130. A gas source 110 supplies a bias flow of pressurized gas through gas source conduit 141, which splits at 142 into patient conduit 150 and bubbler conduit 140. The lengths and cross-sectional shapes of the bubbler 170, the gas source conduit 141, the patient conduit 150 and the bubbler conduit 140 are preferably short and substantially circular or slightly oval in shape. However, any or all of the bubbler 170, the gas source conduit 141, the patient conduit 150 and the bubbler conduit 140 can have any length or cross-sectional shape including but not limited to: square, rectangular, triangular etc., without departing from the spirit of present disclosure.

The length of the bubbler 170 is preferably measured from any distal edge of the bubbler exit portion 180 to any portion of the bubbler elbow 175, or any point inside of the bubbler elbow 175. However, the length of the bubbler 170 can also be measured from any surface of the bubbler exit portion 180 to any portion of the of the bubbler conduit 140 including any outside surface or edge, any inside surface or edge or from any point inside of the bubbler conduit 140. In some embodiments, the length of the bubbler 170 as measured from the distal edge of the bubbler exit portion 180 to the outside of the bubbler elbow 175 or any point inside of the bubbler elbow 175 is about 0.5 cm to 100 cm, desirably 1 cm to 50 cm, preferably about 3 cm to 15 cm as measured from the distal edge of the bubbler exit portion 180 to the outside of the bubbler elbow 175 or any point inside of the bubbler elbow 175. That is, in some embodiments, the length of the bubbler 170 as measured from the distal edge of the bubbler exit portion 180 to the outside of the bubbler elbow 175 or any point inside of the bubbler elbow 175 can be at least, equal to, greater than or any number in between about 1 cm, 2 cm, 3 cm, 4 cm, 5 cm, 6 cm, 7 cm, 8 cm, 9 cm, 10 cm, 11 cm, 12 cm, 13 cm, 14 cm, 15 cm, 16 cm, 17 cm, 18 cm, 19 cm, 20 cm, 21 cm, 22 cm, 23 cm, 24 cm, 25 cm, 26 cm, 27 cm, 28 cm, 29 cm, 30 cm, 31 cm, 32 cm, 33 cm, 34 cm, 35 cm, 36 cm, 37 cm, 38 cm, 39 cm, 40 cm, 41 cm, 42 cm, 43 cm, 44 cm, 45 cm, 46 cm, 47 cm, 48 cm, 49 cm and 50 cm. Although not a desirable embodiment, the length of the bubbler 170 as measured from the distal edge of the bubbler exit portion 180 to the outside of the bubbler elbow 175 or any point inside of the bubbler elbow 175 can be at least, equal to, greater than or any number in between about 50 cm, 55 cm, 60 cm, 65 cm, 70 cm, 75 cm, 80 cm, 85 cm, 90 cm, 95 cm, and 100 cm. In some embodiments, the length of the bubbler 170 as measured from the distal edge of the bubbler exit portion 180 to the outside of the bubbler elbow 175 or any point inside of the bubbler elbow 175 can be any length so long as the device is configured to produce a high amplitude, low frequency broadband oscillating pressure wave having more than 50% of its average power spectra occur below about 10 Hz, 9 Hz, 8 Hz, 7 Hz, 6 Hz, 5 Hz, 4 Hz, 3 Hz, or 2 Hz when the bias gas flow is at least 2 L/min in a model test lung system comprising a hermetically sealed silastic lung within a calibrated plethysmograph.

In certain embodiments of the bubbler 170, the diameter of the bubbler 170 is about 0.1 cm to 10 cm, desirably 0.25 cm to 5 cm, preferably 1 cm to 2 cm. That is, in some embodiments, the diameter of the bubbler 170 can be at least, equal to, greater than or any number in between about 0.25 cm, 0.5 cm, 0.75 cm, 1.0 cm, 1.25 cm, 1.5 cm, 1.75 cm, 2.0 cm, 2.25 cm, 2.5 cm, 2.75 cm, 3.0 cm, 3.25 cm, 3.5 cm, 3.75 cm, 4.0 cm, 4.25 cm, 4.5 cm, 4.75 cm and 5.0 cm. Although not a desirable embodiment, the diameter of the bubbler 170 can be at least, equal to, greater than or any number in between about 5 cm, 5.5 cm, 6.0 cm, 6.5 cm, 7.0 cm, 7.5 cm, 8.0 cm, 8.5 cm, 9.0 cm, 9.5 cm, and 10.0 cm. In some embodiments, the diameter of the bubbler 170 can be any size so long as the device is configured to produce a high amplitude, low frequency broadband oscillating pressure wave having more than 50% of its average power spectra occur below about 10 Hz, 9 Hz, 8 Hz, 7 Hz, 6 Hz, 5 Hz, 4 Hz, 3 Hz, or 2 Hz when the bias gas flow is at least 2 L/min in a model test lung system comprising a hermetically sealed silastic lung within a calibrated plethysmograph.

In some embodiments, the cross-sectional area of the bubbler 170, as defined by a plane transverse to the longitudinal axis of the bubbler 170, is about 0.005 $cm^2$ to 350 $cm^2$, desirably 0.2 $cm^2$ to 80 $cm^2$, and preferably about 3.10 $cm^2$ to 13 $cm^2$. That is, in some embodiments, the cross-sectional area of the bubbler 170 can be at least, equal to, greater than, or any number in between about 0.2 $cm^2$, 0.5 $cm^2$, 0.75 $cm^2$, 1 $cm^2$, 2 $cm^2$, 3 $cm^2$, 4 $cm^2$, 5 $cm^2$, 6 $cm^2$, 7 $cm^2$, 8 $cm^2$, 9 $cm^2$, 10 cm², 11 cm², 12 cm², 13 cm², 14 cm², 15 cm², 16 cm², 17 cm², 18 cm², 19 cm², 20 cm², 25 cm², 30 cm², 35 cm², 40 cm², 45 cm², 50 cm², 55 cm², 60 cm², 65 cm², 70 cm², 75 cm², and 80 cm². Although not a desirable embodiment, the cross-sectional area of the bubbler 170 can be at least, equal to, greater than, or any number in between about 80 cm², 90 cm², 100 cm², 110 cm², 120 cm², 130 cm², 140 cm², 150 cm², 160 cm², 170 cm², 180 cm², 190 cm², 200 cm², 210 cm², 220 cm², 230 cm², 240 cm², 250 cm², 260 cm², 270 cm², 280 cm², 290 cm², 300 cm², 310 cm², 320 cm², 330 cm², 340 cm², and 350 cm². In some embodiments, the cross-sectional area of the bubbler 170 can be any size so long as the device is configured to produce a high amplitude, low frequency broadband oscillating pressure wave having more than 50% of its average power spectra occur below about 10 Hz, 9 Hz, 8 Hz, 7 Hz, 6 Hz, 5 Hz, 4 Hz, 3 Hz, or 2 Hz when the bias gas flow is at least 2 L/min in a model test lung system comprising a hermetically sealed silastic lung within a calibrated plethysmograph.

The depth at which the bubbler 170 is submerged in the fluid 165 can be measured from the fluid surface to the bubbler elbow 175, the bubbler exit portion 180, or any other portion of the bubbler 170 there between. In some embodiments of the patient ventilation system 100, the depth at which the bubbler 170 is submerged in the fluid 165, as measured from the fluid surface to either the bubbler elbow 175, the bubbler exit portion 180, or any other portion of the bubbler 170 there between, is about 0.1 cm to 500 cm, desirably 1 cm to 200 cm, and preferably about 1.5 cm to 30 cm. That is, in some embodiments, the depth of the bubbler 170 as measured from the fluid surface to either the bubbler elbow 175, the bubbler exit portion 180, or any other portion of the bubbler 170 there between can be at least, equal to, greater than, or any number in between about 1 cm, 2 cm, 3 cm, 4 cm, 5 cm, 6 cm, 7 cm, 8 cm, 9 cm, 10 cm, 11 cm, 12 cm, 13 cm, 14 cm, 15 cm, 16 cm, 17 cm, 18 cm, 19 cm, 20 cm, 21 cm, 22 cm, 23 cm, 24 cm, 25 cm, 26 cm, 27 cm, 28 cm, 29 cm, 30 cm, 31 cm, 32 cm, 33 cm, 34 cm, 35 cm, 36 cm, 37 cm, 38 cm, 39 cm, 40 cm, 41 cm, 42 cm, 43 cm, 44 cm, 45 cm, 46 cm, 47 cm, 48 cm, 49 cm, 50 cm, 51 cm, 52 cm, 53 cm, 54 cm, 55 cm, 56 cm, 57 cm, 58 cm, 59 cm, 60 cm, 61 cm, 62 cm, 63 cm, 64 cm, 65 cm, 66 cm, 67 cm, 68 cm, 69 cm, 70 cm, 71 cm, 72 cm, 73 cm, 74 cm, 75 cm, 76 cm, 77 cm, 78 cm, 79 cm, 80 cm, 81 cm, 82 cm, 83 cm, 84 cm, 85 cm, 86 cm, 87 cm, 88 cm, 89 cm, 90 cm, 91 cm, 92 cm, 93 cm, 94 cm, 95 cm, 96 cm, 97 cm, 98 cm, 99 cm, 100 cm, 101 cm, 102 cm, 103 cm, 104 cm, 105 cm, 106 cm, 107 cm, 108 cm, 109 cm, 110 cm, 111 cm, 112 cm, 113 cm, 114 cm, 115 cm, 116 cm, 117 cm, 118 cm, 119 cm, 120 cm, 121 cm, 122 cm, 123 cm, 124 cm, 125 cm, 126 cm, 127 cm, 128 cm, 129 cm, 130 cm, 131 cm, 132 cm, 133 cm, 134 cm, 135 cm, 136 cm, 137 cm, 138 cm, 139 cm, 140 cm, 141 cm, 142 cm, 143 cm, 144 cm, 145 cm, 146 cm, 147 cm, 148 cm, 149 cm, 150 cm, 151 cm, 152 cm, 153 cm, 154 cm, 155 cm, 156 cm, 157 cm, 158 cm, 159 cm, 160 cm, 161 cm, 162 cm, 163 cm, 164 cm, 165 cm, 166 cm, 167 cm, 168 cm, 169 cm, 170 cm, 171 cm, 172 cm, 173 cm, 174 cm, 175 cm, 176 cm, 177 cm, 178 cm, 179 cm, 180 cm, 181 cm, 182 cm, 183 cm, 184 cm, 185 cm, 186 cm, 187 cm, 188 cm, 189 cm, 190 cm, 191 cm, 192 cm, 193 cm, 194 cm, 195 cm, 196, 197 cm, 198 cm, 199 cm, and 200 cm. Although not a desirable embodiment, the depth of the bubbler 170 as measured from the fluid surface to either the bubbler elbow 175, the bubbler exit portion 180, or any other portion of the bubbler 170 there between can be at least, equal to, greater than, or any number in between about 200 cm, 210 cm, 220 cm, 230 cm, 240 cm, 250 cm, 260 cm, 270 cm, 280 cm, 290 cm, 300 cm, 310 cm, 320 cm, 330 cm, 340 cm, 350 cm, 360 cm, 370 cm, 380 cm, 390 cm, 400 cm, 410 cm, 420 cm, 430 cm, 440 cm, 450 cm, 460 cm, 470 cm, 480 cm, 490 cm, and 500 cm. In some embodiments, the depth at which the bubbler 170 is submerged in the fluid 165, as measured from the fluid surface to either the bubbler elbow 175, the bubbler exit portion 180, or any other portion of the bubbler 170 there between, can be any depth so long as the device is configured to produce a high amplitude, low frequency broadband oscillating pressure wave having more than 50% of its average power spectra occur below about 10 Hz, 9 Hz, 8 Hz, 7 Hz, 6 Hz, 5 Hz, 4 Hz, 3 Hz, or 2 Hz when the bias gas flow is at least 2 L/min in a model test lung system comprising a hermetically sealed silastic lung within a calibrated plethysmograph.

Continuing with FIG. 1, the frequencies and amplitudes of pressure oscillations can be controlled by adjusting the angle of the bubbler 170 placed in the liquid 165. For the purposes of this application, the angle of bubbler 170 can be adjusted between 0° and 180° with respect to a line normal to the surface of the fluid 166, where 0° corresponds to the bubbler exit portion 180 being oriented straight down, away from the fluid surface 166 and 180° corresponds to the bubbler exit portion 180 being oriented straight up, toward the fluid surface 166. Alternatively, or in addition thereto, the angle of bubbler 170 can be adjusted between 0° and 180° with respect to a vertical axis defined by gravity and pointing toward the Earth's center of mass, where 0° corresponds to the bubbler exit portion 180 being oriented straight down, toward the Earth's center of mass and 180° corresponds to the bubbler exit portion 180 being oriented straight up, away from the Earth's center of mass.

In some embodiments, the angle of the bubbler 170 is about 1° to 89° or about 91° to 180°, preferably 100° to 170°. That is, in some embodiments, the angle of the bubbler 170 as measured with respect to a line normal to the surface of the fluid 166 or with respect to a vertical axis can be at least, equal to, greater than or any number in between about 1°, 2°, 3°, 4°, 5°, 6°, 7°, 8°, 9°, 10°, 11°, 12°, 13°, 14°, 15°, 16°, 17°, 18°, 19°, 20°, 21°, 22°, 23°, 24°, 25°, 26°, 27°, 28°, 29°, 30°, 31°, 32°, 33°, 34°, 35°, 36°, 37°, 38°, 39°, 40°, 41°, 42°, 43°, 44°, 45°, 46°, 47°, 48°, 49°, 50°, 51°, 52°, 53°, 54°, 55°, 56°, 57°, 58°, 59°, 60°, 61°, 62°, 63°, 64°, 65°, 66°, 67°, 68°, 69°, 70°, 71°, 72°, 73°, 74°, 75°, 76°, 77°, 78°, 79°, 80°, 81°, 82°, 83°, 84°, 85°, 86°, 87°, 88°, 89°, 91°, 92°, 93°, 94°, 95°, 96°, 97°, 98°, 99°, 100°, 101°, 102°, 103°, 104°, 105°, 106°, 107°, 108°, 109°, 110°, 111°, 112°, 113°, 114°, 115°, 116°, 117°, 118°, 119°, 120°, 121°, 122°, 123°, 124°, 125°, 126°, 127°, 128°, 129°, 130°, 131°, 132°, 133°, 134°, 135°, 136°, 137°, 138°, 139°, 140°, 141°, 142°, 143°, 144°, 145°, 146°, 147°, 148°, 149°, 150°, 151°, 152°, 153°, 154°, 155°, 156°, 157°, 158°, 159°, 160°, 161°, 162°, 163°, 164°, 165°, 166°, 167°, 168°, 169°, 170°, 171°, 172°, 173°, 174°, 175°, 176°, 177°, 178°, 179°, and 180°. In some embodiments, the angle of the bubbler 170 as measured with respect to a line normal to the surface of the fluid 166 or with respect to a vertical axis can be any angle that is not 0° or 90° so long as the device is configured to produce a high amplitude, low frequency broadband oscillating pressure wave having more than 50% of its average power spectra occur below about 10 Hz, 9 Hz, 8 Hz, 7 Hz, 6 Hz, 5 Hz, 4 Hz, 3 Hz, or 2 Hz when the bias gas flow is at least 2 L/min in a model test lung system comprising a hermetically sealed silastic lung within a calibrated plethysmograph.

Figure 25:
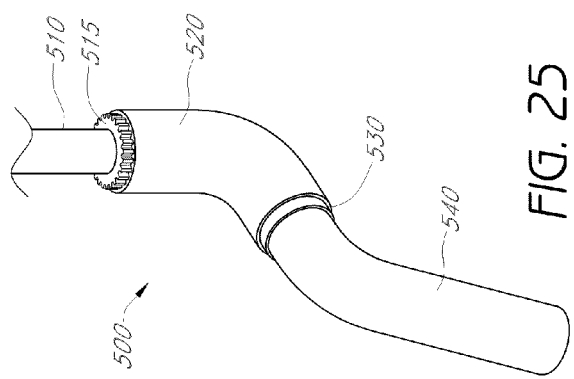
FIG. 25 shows a top perspective view of the gas-flow control tube of FIG. 24 adjusted to direct gas flow in a downward direction.
Figure 24:
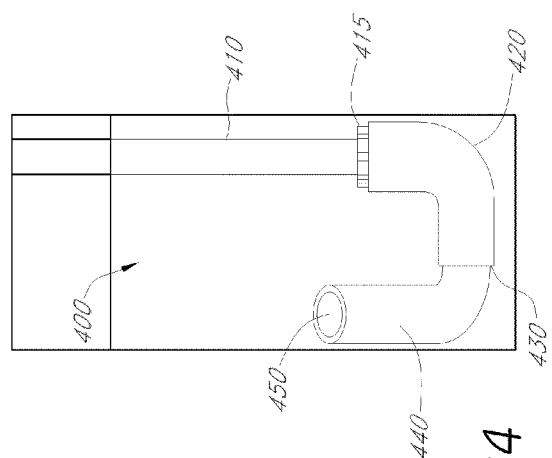
FIG. 24 depicts a side view of the gas-flow control conduit of FIG. 23 submerged in a fluid-filled container.
Figure 23:
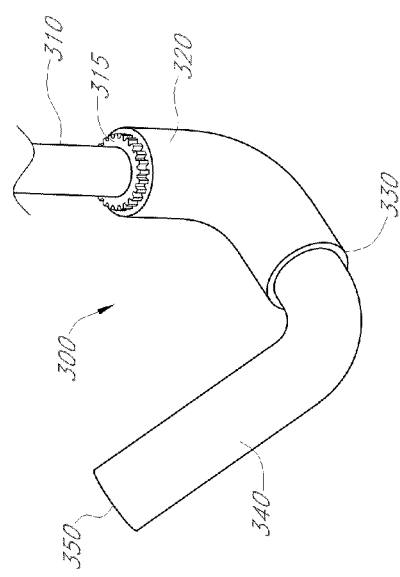
FIG. 23 illustrates a top perspective view of a gas-flow control conduit configured to vary the exit angle of gas from the conduit.
Figure 28:
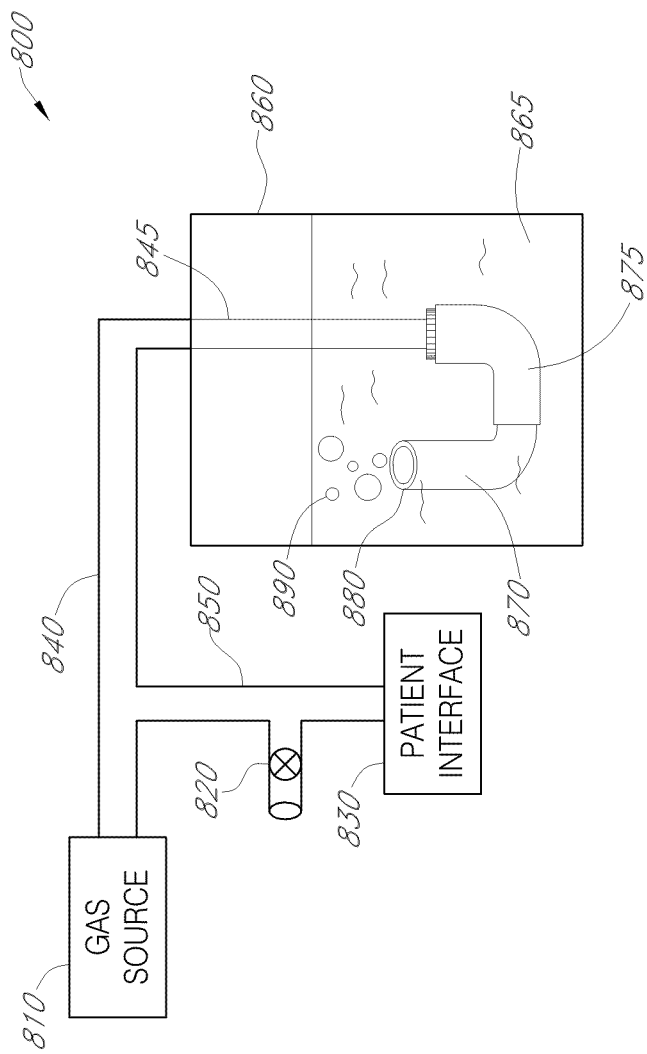
FIG. 28 shows the patient ventilation system of FIG. 1 with a gas-flow control conduit configured to vary the exit angle of gas from the conduit.

FIGS. 23-25 illustrate one embodiment of a swivel device 300 for controlling the angle of bubble gases released into a fluid. Referring to FIG. 23, the bubbler conduit 310 is attached to the elbow 320 via connector 315. The elbow 320 is a hollow conduit configured to receive bubbler swivel 340 at the distal end of the elbow 330 so as to allow the bubbler swivel 340 to rotate within the elbow 320 and allow the bubbler swivel exit portion 350 to assume different angles. The connecting interface between the elbow 320 and the bubbler swivel 340 preferably forms a substantially water tight seal. However, in other embodiments the connecting interface formed between the elbow 320 and the bubbler swivel 340 does not form a substantially water tight seal. In one embodiment, the bubbler swivel 340 and/or elbow 320 have angle markings (not shown) so that the user can visually set and measure the angle manually. In some embodiments, the bubbler swivel 340 may be automated such that a user or a computer can change or direct the change of the bubbler angle. FIG. 25 shows the bubbler swivel of FIG. 23 adjusted downward and FIG. 24 shows the bubbler swivel of FIG. 23 immersed in a container holding a fluid 400. FIG. 28 shows the device of FIGS. 23-25 implemented with the patient ventilation system 100 of FIG. 1.

Figures 26, 27:
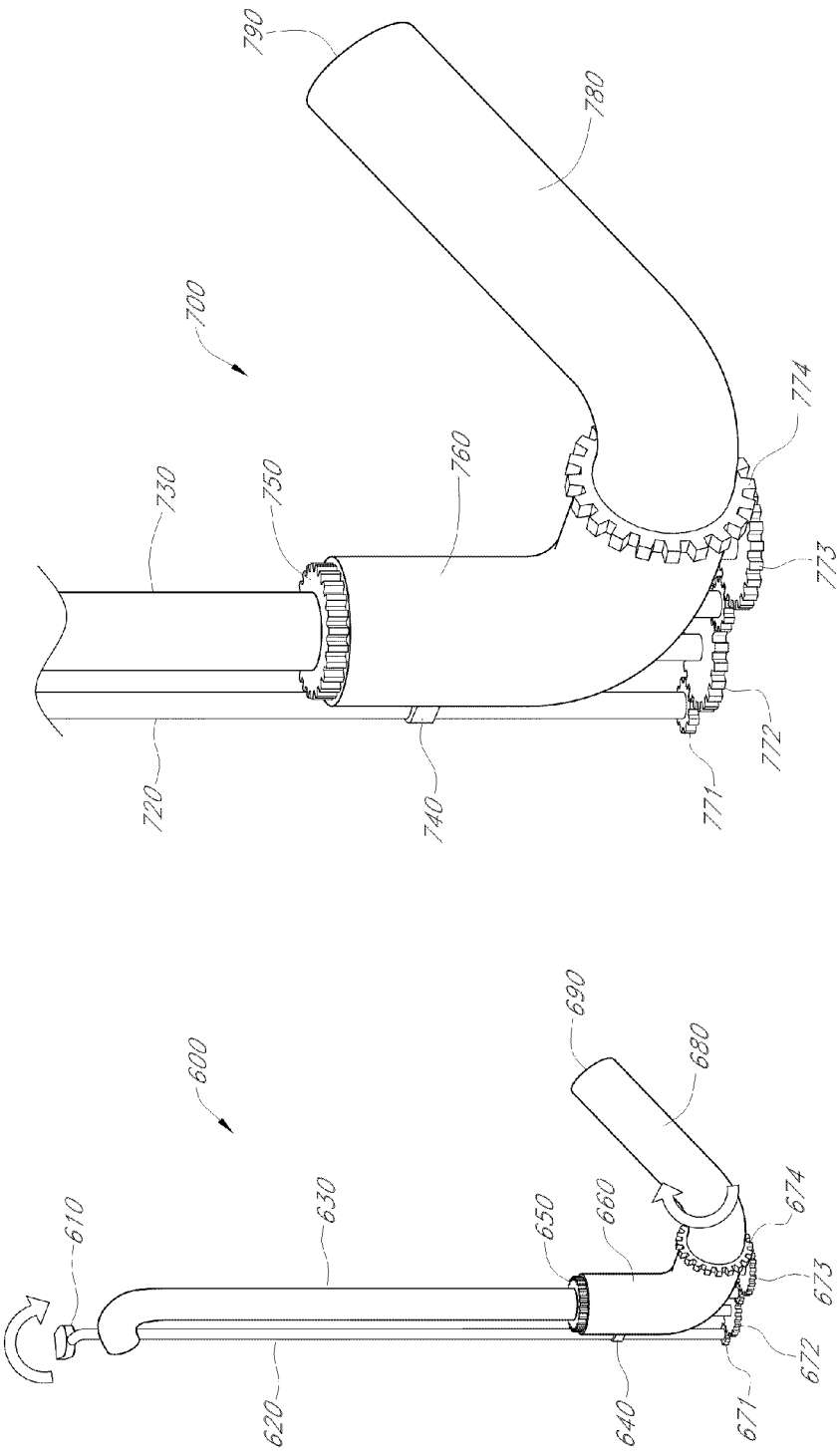
FIG. 26 illustrates a top perspective view of the gas-flow control conduit of FIG. 23 with a mechanical gear system configured to vary the exit angle of gas from the conduit.
FIG. 27 depicts a closer view of the gas-flow control conduit with the mechanical gear system of FIG. 26.

FIGS. 26 and 27 show another embodiment of the swivel device of FIGS. 23-25 employing a mechanical gear and rod mechanism to adjust the angle of the bubbler swivel 680. The operator rotates handle 610 connected to shaft 620, which is secured to elbow 660 at 640, causing gears 671-674 to rotate, thereby rotating bubbler swivel 680. This allows the operator to adjust the bubbler swivel angle from above the fluid. FIG. 27 is a closer view of the device of FIG. 26.

Referring back to FIG. 1, gas delivered by the gas source 110 may comprise atmospheric gases or any combination, mixture or blend of suitable gases, including but not limited to: atmospheric air, oxygen, nitrogen, carbon dioxide, helium, or combinations thereof. The gas source 110 may comprise a gas compressor, a mechanical ventilator, an electromechanical ventilator, a container of pressurized gas, a substantially portable container of pre-pressurized gas, a gas-line hookup (such as found in a hospital) or any other suitable source of pressurized gas, or combinations thereof. The gas source 110 is preferably controlled or configured to have a substantially constant bias gas flow rate, which can be controlled by the care giver and adjusted according to the individual characteristics of each patient. For example, the patient ventilation system 100 or gas source 110 may also include one or more flow control devices (not shown) such as a mechanical valve, an electronically controlled mechanical valve, a rotameter, a pressure regulator, a flow transducer, or combinations thereof Bias gas flow rates, which are commonly used in the art, typically range from about 2 L/min to about 10 L/min. However, one of skill in the art will understand that bias gas flow rates below about 2 L/min and above about 10 L/min may also be used. For example, larger patients generally require larger bias flow rates.

In some embodiments, the bias gas flow rate is about 0.1 L/min to 30 L/min, 1 L/min to 20 L/min, preferably 2 L/min to 10 L/min. That is, in some embodiments, the bias gas flow rate can be at least, equal to, greater than or any number in between about 1 L/min, 2 L/min, 3 L/min, 4 L/min, 5 L/min, 6 L/min, 7 L/min, 8 L/min, 9 L/min, 10 L/min, 11 L/min, 12 L/min, 13 L/min, 14 L/min, 15 L/min, 16 L/min, 17 L/min, 18 L/min, 19 L/min, and 20 L/min. Although not a desirable embodiment, the bias gas flow rate can be at least, equal to, greater than or any number in between about 20 L/min, 21 L/min, 22 L/min, 23 L/min, 24 L/min, 25 L/min, 26 L/min, 27 L/min, 28 L/min, 29 L/min, and 30 L/min. In some embodiments, the bias gas flow rate can be any rate so long as the device is configured to produce a high amplitude, low frequency broadband oscillating pressure wave having more than 50% of its average power spectra occur below about 10 Hz, 9 Hz, 8 Hz, 7 Hz, 6 Hz, 5 Hz, 4 Hz, 3 Hz, or 2 Hz when the bias gas flow is at least 2 L/min in a model test lung system comprising a hermetically sealed silastic lung within a calibrated plethysmograph.

The patient conduit 150 can include a high pressure "pop-off" or "pop-open" safety valve 120 to protect the patient from receiving airway pressures greater than a pre-determined threshold to help prevent lung damage and to prevent high pressures from reaching the patient in the unlikely event that the patient circuit is occluded between the patient and the gas exiting the system through the fluid container. Additionally, the patient conduit 150 can include a low pressure "pop-open" or one way valve 125 to protect the patient from receiving airway pressures lower than a pre-determined threshold, for example sub-atmospheric pressures. In this manner, the one way valve 125 can help prevent alveoli from collapsing and/or help prevent the patient from inhaling fluid 165. Fresh gas of controlled concentration (not shown) can also be supplied to the one way valve 125.

A Heat and Moisture Exchanger (HME) (not shown) can also be included in the patient ventilation system 100 to control the temperature and moisture content of gas delivered to the patient interface. Additionally, the patient ventilation system 100 can also include a valve system 125 to prevent the patient from re-breathing exhalation gases. For example, if the patient inhalation flow rate is greater than the bias flow rate then the patient will tend to rebreathe exhaled gases. A One-way valve 125 can be provided to allow room air, or gas of a controlled concentration, to help reduce or prevent the patient from rebreathing exhalation gases.

Bias gas flows from the gas source 110 to the patient interface 130 for inhalation by the patient. The patient interface 130 can be invasive or non-invasive, including but not limited to: facial or nasal masks, nasal prongs, tube(s) placed in the nasal pharynx, endotracheal tubes, tracheostomy tubes, or combinations thereof Bias gas and patient exhalation gases flow through bubbler conduit 140 to bubbler 170, which is placed in a container 160 holding a fluid 165. Preferably, the fluid 165 comprises water. However, the fluid 165 may comprise any number of suitable fluids or liquids exhibiting a wide range of densities, masses and viscosities including, but not limited to: water, oil, ethylene glycol, ethanol, any fluid containing hydrocarbons, or combinations thereof.

In some embodiments, the fluid or liquid density is about 0.5 to 1.5 g/cm$^3$ at 20° C., desirably about 0.8 to 1.1 g/cm$^3$ at 20° C., and preferably about 0.85 to 1.05 g/cm$^3$ at 20° C. That is, in some embodiments, the fluid density can be at least, equal to, greater than, or any number in between about 0.50 g/cm$^3$ at 20° C., 0.55 g/cm$^3$ at 20° C., 0.60 g/cm$^3$ at 20° C., 0.65 g/cm$^3$ at 20° C., 0.70 g/cm$^3$ at 20° C., 0.75 g/cm$^3$ at 20° C., 0.80 g/cm$^3$ at 20° C., 0.85 g/cm$^3$ at 20° C., 0.90 g/cm$^3$ at 20° C., 0.95 g/cm$^3$ at 20° C., 1.00 g/cm$^3$ at 20° C., 1.05 g/cm$^3$ at 20° C., 1.10 g/cm$^3$ at 20° C., 1.15 g/cm$^3$ at 20° C., 1.20 g/cm$^3$ at 20° C., 1.25 g/cm$^3$ at 20° C., 1.30 g/cm$^3$ at 20° C., 1.35 g/cm$^3$ at 20° C., 1.40 g/cm$^3$ at 20° C., 1.45 g/cm$^3$ at 20° C., and 1.50 g/cm$^3$ at 20° C. In some embodiments, the fluid or liquid density can be any density so long as the device is configured to produce a high amplitude, low frequency broadband oscillating pressure wave having more than 50% of its average power spectra occur below about 10 Hz, 9 Hz, 8 Hz, 7 Hz, 6 Hz, 5 Hz, 4 Hz, 3 Hz, or 2 Hz when the bias gas flow is at least 2 L/min in a model test lung system comprising a hermetically sealed silastic lung within a calibrated plethysmograph.

Figure 29:
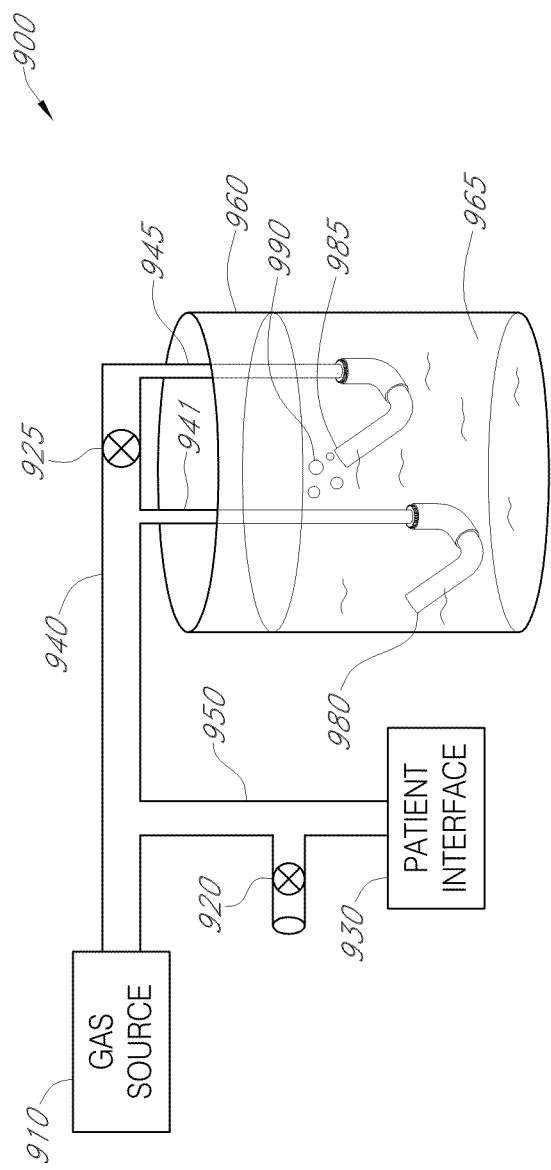
FIG. 29 shows a patient ventilation system utilizing multiple bubblers submerged in fluid and configured to differentially modulate inspiratory and expiratory airway pressures.
Figure 30:
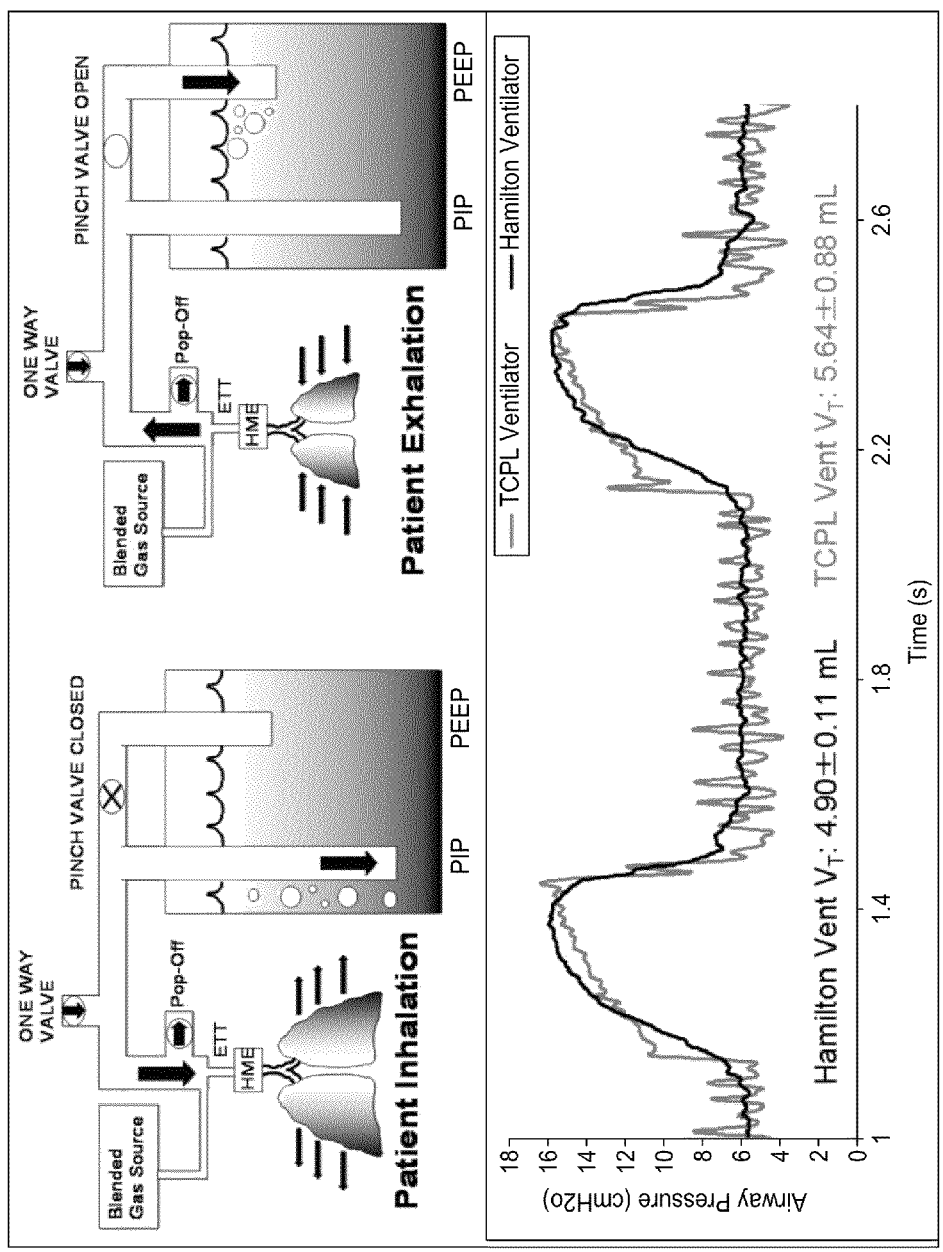
FIG. 30 compares the airway pressure signals generated by a conventional ventilator and a Hansen Ventilator and demonstrates the two different gas flow directions during inhalation (valve closed) and exhalation (valve open).

FIG. 29 illustrates a patient ventilation system 900 (also referred to herein as a "Hansen Ventilator") utilizing two bubblers 985 and 980 (also referred to as a "bubbleators" or "High Amplitude Bubblers" (HAB) or "positive end-expiratory pressure control conduits" or "peak inspiratory pressure control conduits" or in some embodiments, "simple conduits") submerged in a fluid 965 and configured to modulate airway pressures in a patient receiving Bi-PAP. However, in other embodiments the two bubblers 985 and 980 need not be used, and may be replaced by simple conduits (not shown). In other embodiments, more than two bubblers and/or simple conduits may be used. In yet other embodiments, the bubblers (and/or simple conduits) may each have substantially similar lengths and diameters or different lengths and diameters. A gas source 910 supplies a bias flow of pressurized gas to patient conduit 950 and bubbler conduit 940. The lengths and cross-sectional shapes of the bubblers 985 and 980 (or simple conduits), the patient conduit 950 and the bubbler conduit 940 are preferably short and substantially circular or slightly oval in shape. However, any or all of the bubblers 985 and 980 (or simple conduits) the patient conduit 950 and the bubbler conduit 940 can have any length or cross-sectional shape including but not limited to: square, rectangular, triangular etc., without departing from the spirit of the present disclosure.

In some embodiments the length of each of the bubblers 985 and 980 as measured from the distal edge of the bubbler exit portion to the outside of the bubbler elbow or any point inside of the bubbler elbow can be about 0.5 cm to 100 cm, desirably 1 cm to 50 cm, preferably 3 cm to 15 cm. That is, in some embodiments, the length of each of the bubblers 985 and 980 as measured from the distal edge of the bubbler exit portion to the outside of the bubbler elbow or any point inside of the bubbler elbow can be at least, equal to, greater than or any number in between about 1 cm, 2 cm, 3 cm, 4 cm, 5 cm, 6 cm, 7 cm, 8 cm, 9 cm, 10 cm, 11 cm, 12 cm, 13 cm, 14 cm, 15 cm, 16 cm, 17 cm, 18 cm, 19 cm, 20 cm, 21 cm, 22 cm, 23 cm, 24 cm, 25 cm, 26 cm, 27 cm, 28 cm, 29 cm, 30 cm, 31 cm, 32 cm, 33 cm, 34 cm, 35 cm, 36 cm, 37 cm, 38 cm, 39 cm, 40 cm, 41 cm, 42 cm, 43 cm, 44 cm, 45 cm, 46 cm, 47 cm, 48 cm, 49 cm and 50 cm. Although not a desirable embodiment, the length of the bubblers 985 and 980 as measured from the distal edge of the bubbler exit portion to the outside of the bubbler elbow or any point inside of the bubbler elbow can be at least, equal to, greater than or any number in between about 50 cm, 55 cm, 60 cm, 65 cm, 70 cm, 75 cm, 80 cm, 85 cm, 90 cm, 95 cm, and 100 cm. In some embodiments, the length of the bubblers as measured from the distal edge of the bubbler exit portion to the outside of the bubbler elbow or any point inside of the bubbler elbow can be any length so long as the device is configured to produce a high amplitude, low frequency broadband oscillating pressure wave having more than 50% of its average power spectra occur below about 10 Hz, 9 Hz, 8 Hz, 7 Hz, 6 Hz, 5 Hz, 4 Hz, 3 Hz, or 2 Hz when the bias gas flow is at least 2 L/min in a model test lung system comprising a hermetically sealed silastic lung within a calibrated plethysmograph.

In certain embodiments of the bubblers 985 and 980 (and/or simple conduits), the diameters of the bubblers 985 and 980 (and/or simple conduits) are about 0.1 cm to 10 cm, desirably 0.25 cm to 5 cm, preferably 1 cm to 2 cm. That is, in some embodiments, the diameter of the bubblers 985 and 980 (and/or simple conduits) can be at least, equal to, greater than or any number in between about 0.25 cm, 0.5 cm, 0.75 cm, 1.0 cm, 1.25 cm, 1.5 cm, 1.75 cm, 2.0 cm, 2.25 cm, 2.5 cm, 2.75 cm, 3.0 cm, 3.25 cm, 3.5 cm, 3.75 cm, 4.0 cm, 4.25 cm, 4.5 cm, 4.75 cm and 5.0 cm. Although not a desirable embodiment, the diameter of the bubblers 985 and 980 (and/or simple conduits) can be at least, equal to, greater than or any number in between about 5 cm, 5.5 cm, 6.0 cm, 6.5 cm, 7.0 cm, 7.5 cm, 8.0 cm, 8.5 cm, 9.0 cm, 9.5 cm, and 10.0 cm. In some embodiments, the diameter of the bubblers 985 and 980 (and/or simple conduits) can be any size so long as the device is configured to produce a high amplitude, low frequency broadband oscillating pressure wave having more than 50% of its average power spectra occur below about 10 Hz, 9 Hz, 8 Hz, 7 Hz, 6 Hz, 5 Hz, 4 Hz, 3 Hz, or 2 Hz when the bias gas flow is at least 2 L/min in a model test lung system comprising a hermetically sealed silastic lung within a calibrated plethysmograph.

In some embodiments, the cross-sectional area of at least one of the bubblers (or simple conduits), as defined by a plane transverse to the longitudinal axis of the bubbler, is about 0.005 cm$^2$ to 350 cm$^2$, desirably 0.2 cm$^2$ to 80 cm$^2$, and preferably about 3.10 cm$^2$ to 13 cm$^2$. That is, in some embodiments, the cross-sectional area of the bubblers can be at least, equal to, greater than, or any number in between about 0.2 cm$^2$, 0.5 cm$^2$, 0.75 cm$^2$, 1 cm$^2$, 2 cm$^2$, 3 cm$^2$, 4 cm$^2$, 5 cm$^2$, 6 cm$^2$, 7 cm$^2$, 8 cm$^2$, 9 cm$^2$, 10 cm$^2$, 11 cm$^2$, 12 cm$^2$, 13 cm$^2$, 14 cm$^2$, 15 cm$^2$, 16 cm$^2$, 17 cm$^2$, 18 cm$^2$, 19 cm$^2$, 20 cm$^2$, 25 cm$^2$, 30 cm$^2$, 35 cm$^2$, 40 cm$^2$, 45 cm$^2$, 50 cm$^2$, 55 cm$^2$, 60 cm$^2$, 65 cm$^2$, 70 cm$^2$, 75 cm$^2$, and 80 cm$^2$. Although not a desirable embodiment, the cross-sectional area of the bubblers can be at least, equal to, greater than, or any number in between about 80 cm$^2$, 90 cm$^2$, 100 cm$^2$, 110 cm$^2$, 120 cm$^2$, 130 cm$^2$, 140 cm$^2$, 150 cm$^2$, 160 cm$^2$, 170 cm$^2$, 180 cm$^2$, 190 cm$^2$, 200 cm$^2$, 210 cm$^2$, 220 cm$^2$, 230 cm$^2$, 240 cm$^2$, 250 cm$^2$, 260 cm$^2$, 270 cm$^2$, 280 cm$^2$, 290 cm$^2$, 300 cm$^2$, 310 cm$^2$, 320 cm$^2$, 330 cm$^2$, 340 cm$^2$, and 350 cm$^2$. In some embodiments, the cross-sectional area of the bubblers can be any size so long as the device is configured to produce a high amplitude, low frequency broadband oscillating pressure wave having more than 50% of its average power spectra occur below about 10 Hz, 9 Hz, 8 Hz, 7 Hz, 6 Hz, 5 Hz, 4 Hz, 3 Hz, or 2 Hz when the bias gas flow is at least 2 L/min in a model test lung system comprising a hermetically sealed silastic lung within a calibrated plethysmograph.

The depth at which the bubblers 980 and 985 (and/or simple conduits) are submerged in the fluid 965 can be measured from the fluid surface to either the elbow of the bubbler, the bubbler exit portions, or any other portion of the bubblers there between, or the distal end of the simple conduit, if any. In some embodiments of the patient ventilation system 900, the depth at which the bubblers 980 and 985 (and/or simple conduits) are submerged in the fluid 965 is about 0.1 to 500 cm, desirably 1 cm to 200 cm, and preferably about 1.5 cm to 50 cm. That is, in some embodiments, the depth of the bubblers (and/or simple conduits) as measured from the fluid surface to either the bubbler elbow, the bubbler exit portion, any other portion of the bubbler or simple conduit there between, can be at least, equal to, greater than, or any number in between about 1 cm, 2 cm, 3 cm, 4 cm, 5 cm, 6 cm, 7 cm, 8 cm, 9 cm, 10 cm, 11 cm, 12 cm, 13 cm, 14 cm, 15 cm, 16 cm, 17 cm, 18 cm, 19 cm, 20 cm, 21 cm, 22 cm, 23 cm, 24 cm, 25 cm, 26 cm, 27 cm, 28 cm, 29 cm, 30 cm, 31 cm, 32 cm, 33 cm, 34 cm, 35 cm, 36 cm, 37 cm, 38 cm, 39 cm, 40 cm, 41 cm, 42 cm, 43 cm, 44 cm, 45 cm, 46 cm, 47 cm, 48 cm, 49 cm, 50 cm, 51 cm, 52 cm, 53 cm, 54 cm, 55 cm, 56 cm, 57 cm, 58 cm, 59 cm, 60 cm, 61 cm, 62 cm, 63 cm, 64 cm, 65 cm, 66 cm, 67 cm, 68 cm, 69 cm, 70 cm, 71 cm, 72 cm, 73 cm, 74 cm, 75 cm, 76 cm, 77 cm, 78 cm, 79 cm, 80 cm, 81 cm, 82 cm, 83 cm, 84 cm, 85 cm, 86 cm, 87 cm, 88 cm, 89 cm, 90 cm, 91 cm, 92 cm, 93 cm, 94 cm, 95 cm, 96 cm, 97 cm, 98 cm, 99 cm, 100 cm, 101 cm, 102 cm, 103 cm, 104 cm, 105 cm, 106 cm, 107 cm, 108 cm, 109 cm, 110 cm, 111 cm, 112 cm, 113 cm, 114 cm, 115 cm, 116 cm, 117 cm, 118 cm, 119 cm, 120 cm, 121 cm, 122 cm, 123 cm, 124 cm, 125 cm, 126 cm, 127 cm, 128 cm, 129 cm, 130 cm, 131 cm, 132 cm, 133 cm, 134 cm, 135 cm, 136 cm, 137 cm, 138 cm, 139 cm, 140 cm, 141 cm, 142 cm, 143 cm, 144 cm, 145 cm, 146 cm, 147 cm, 148 cm, 149 cm, 150 cm, 151 cm, 152 cm, 153 cm, 154 cm, 155 cm, 156 cm, 157 cm, 158 cm, 159 cm, 160 cm, 161 cm, 162 cm, 163 cm, 164 cm, 165 cm, 166 cm, 167 cm, 168 cm, 169 cm, 170 cm, 171 cm, 172 cm, 173 cm, 174 cm, 175 cm, 176 cm, 177 cm, 178 cm, 179 cm, 180 cm, 181 cm, 182 cm, 183 cm, 184 cm, 185 cm, 186 cm, 187 cm, 188 cm, 189 cm, 190 cm, 191 cm, 192 cm, 193 cm, 194 cm, 195 cm, 196, 197 cm, 198 cm, 199 cm, and 200 cm. Although not a desirable embodiment, the depth of the bubblers (and/or simple conduits) as measured from the fluid surface to either the bubbler elbow, the bubbler exit portion, any other portion of the bubbler or simple conduit there between can be at least, equal to, greater than, or any number in between about 200 cm, 210 cm, 220 cm, 230 cm, 240 cm, 250 cm, 260 cm, 270 cm, 280 cm, 290 cm, 300 cm, 310 cm, 320 cm, 330 cm, 340 cm, 350 cm, 360 cm, 370 cm, 380 cm, 390 cm, 400 cm, 410 cm, 420 cm, 430 cm, 440 cm, 450 cm, 460 cm, 470 cm, 480 cm, 490 cm, and 500 cm. In some embodiments, the depth at which the bubblers 980 and 985 (and/or simple conduits) can be submerged in the fluid 965, as measured from the fluid surface to either the bubbler elbow, the bubbler exit portion, or any other portion of the bubbler there between, can be any depth so long as the device is configured to produce a high amplitude, low frequency broadband oscillating pressure wave having more than 50% of its average power spectra occur below about 10 Hz, 9 Hz, 8 Hz, 7 Hz, 6 Hz, 5 Hz, 4 Hz, 3 Hz, or 2 Hz when the bias gas flow is at least 2 L/min in a model test lung system comprising a hermetically sealed silastic lung within a calibrated plethysmograph.

Gas delivered by the gas source 910 may comprise atmospheric gases or any combination, mixture, or blend of suitable gases, including but not limited to: atmospheric air, oxygen, nitrogen, carbon dioxide, helium, or combinations thereof. The gas source 910 may comprise a gas compressor, mechanical ventilator, an electromechanical ventilator, a container of pressurized gas, a substantially portable container of pre-pressurized gas, a gas-line hookup (such as found in a hospital) or any other suitable source of pressurized gas, or combinations thereof. The gas source 910 is preferably controlled or configured to have a substantially constant bias gas flow rate which can be controlled by the care giver and adjusted according to the individual characteristics of each patient. However, in some embodiments the gas source can be controlled or configured to have a variable bias gas flow rate which increases or decreases over time or during breaths. The patient ventilation system 900 or gas source 910 may also include one or more flow control devices (not shown) such as a mechanical valve, an electronically controlled mechanical valve, a rotameter, a pressure regulator, a flow transducer, or combinations thereof. Bias gas flow rates, which are commonly used in the art, typically range from about 2 L/min to about 10 L/min. However, one of skill in the art will understand that bias gas flow rates below about 2 L/min and above about 10 L/min can also be used. For example, larger patients will require larger bias gas flows and it can be desirable to have increasing or decreasing bias flow rates during inhalation, exhalation, or both.

In some embodiments, the bias gas flow rate is about 0.1 L/min to 30 L/min, 1 L/min to 20 L/min, preferably 2 L/min to 10 L/min. That is, in some embodiments, the bias gas flow rate can be at least, equal to, greater than, or any number in between about 1 L/min, 2 L/min, 3 L/min, 4 L/min, 5 L/min, 6 L/min, 7 L/min, 8 L/min, 9 L/min, 10 L/min, 11 L/min, 12 L/min, 13 L/min, 14 L/min, 15 L/min, 16 L/min, 17 L/min, 18 L/min, 19 L/min, and 20 L/min. Although not a desirable embodiment, the bias gas flow rate can be at least, equal to, greater than or any number in between about 20 L/min, 21 L/min, 22 L/min, 23 L/min, 24 L/min, 25 L/min, 26 L/min, 27 L/min, 28 L/min, 29 L/min, and 30 L/min. In some embodiments, the bias gas flow rate can be any rate so long as the device is configured to produce a high amplitude, low frequency broadband oscillating pressure wave having more than 50% of its average power spectra occur below about 10 Hz, 9 Hz, 8 Hz, 7 Hz, 6 Hz, 5 Hz, 4 Hz, 3 Hz, or 2 Hz when the bias gas flow is at least 2 L/min in a model test lung system comprising a hermetically sealed silastic lung within a calibrated plethysmograph.

The patient conduit 950 can include a high pressure "pop-off" or "pop-open" safety valve 920 to protect the patient (not shown) from receiving airway pressures greater than a pre-determined threshold to help prevent lung damage and to prevent high pressures from reaching the patient in the unlikely event that the patient circuit is occluded between the patient and the gas exiting the system through the fluid container. Additionally, the patient conduit 950 can include a low pressure "pop-open" or one way valve (not shown) to protect the patient from receiving airway pressures lower than a pre-determined threshold, for example sub-atmospheric pressures. In this manner, the one way valve can help prevent alveoli from collapsing, help prevent the patient from inhaling fluid 965, and help prevent the patient from re-breathing exhalation gases. Fresh gas of controlled concentration (not shown) can also be supplied to the one way valve.

A Heat and Moisture Exchanger (HME) (not shown) can also be included in the patient ventilation system 900 to control the temperature and moisture content of gas delivered to the patient interface.

Continuing with FIG. 29, Bias gas flows from the gas source 910 to the patient interface 930 for inhalation by the patient. The patient interface 930 can be invasive or non-invasive, including but not limited to: facial or nasal masks, nasal prongs, tube(s) placed in nasal pharynx, endotracheal tubes, tracheostomy tubes, or combinations thereof. Bias gas and patient exhalation gases flow through bubbler conduit 940 to the bubblers which are placed in a container 960 holding a fluid 965. The fluid 965 may comprise any number of suitable fluids or liquids exhibiting a wide range of densities, masses and viscosities including, but not limited to: water, oil, ethylene glycol, ethanol, fluids containing hydrocarbons, or combinations thereof.

In some embodiments, the fluid density is about 0.5 to 1.5 $g/cm^3$ at 20° C., desirably about 0.8 to 1.1 $g/cm^3$ at 20° C., and preferably about 0.85 to 1.05 $g/cm^3$ at 2° C. That is, in some embodiments, the fluid density can be at least, equal to, greater than, or any number in between about 0.50 $g/cm^3$ at 20° C., 0.55 $g/cm^3$ at 20° C., 0.60 $g/cm^3$ at 20° C., 0.65 $g/cm^3$ at 20° C., 0.70 $g/cm^3$ at 20° C., 0.75 $g/cm^3$ at 20° C., 0.80 $g/cm^3$ at 20° C., 0.85 $g/cm^3$ at 20° C., 0.90 $g/cm^3$ at 20° C., 0.95 $g/cm^3$ at 20° C., 1.00 $g/cm^3$ at 20° C., 1.05 $g/cm^3$ at 20° C., 1.10 $g/cm^3$ at 20° C., 1.15 $g/cm^3$ at 20° C., 1.20 $g/cm^3$ at 20° C., 1.25 $g/cm^3$ at 20° C., 1.30 $g/cm^3$ at 20° C., 1.35 $g/cm^3$ at 20° C., 1.40 $g/cm^3$ at 20° C., 1.45 $g/cm^3$ at 20° C., and 1.50 $g/cm^3$ at 20° C. In some embodiments, the fluid or liquid density can be any density so long as the device is configured to produce a high amplitude, low frequency broadband oscillating pressure wave having more than 50% of its average power spectra occur below about 10 Hz, 9 Hz, 8 Hz, 7 Hz, 6 Hz, 5 Hz, 4 Hz, 3 Hz, or 2 Hz when the bias gas flow is at least 2 L/min in a model test lung system comprising a hermetically sealed silastic lung within a calibrated plethysmograph.

The bubbler conduit 940 comprises a valve 925 placed between the two bubblers 980 and 985 (which are at different depths in the fluid 965) to control mean airway pressures, the rate of ventilation, and the inspiratory time for the ventilation system 900. The valve 925 may comprise a mechanical or electromechanical valve, or the valve may be operated by simply pinching flexible tubing (by hand or otherwise). The valve 925 may be electronically controlled or mechanically controlled such that the user is able to set the ventilation rate and inspiratory time or the ratio of inspiratory to expiratory time. The valve 925 is preferably "normally open" such that in the event of failure the valve would be open and the patient would be subjected to the lower pressure and capable of breathing freely through the system. When the valve 925 is open, bias gases flow through bubbler 985, which is set to a lesser depth than bubbler 980, thereby controlling the mean expiratory airway pressure (or positive end expiratory pressure) in the circuit. When the valve 925 is closed, gas in the pressurized circuit flows through bubbler 980, which is deeper than bubbler 985, thereby raising the mean airway pressure in the circuit (or peak inspiratory pressure) and delivering a "mandatory breath" to the patient. The valve 925 can then be opened again to allow the patient to exhale, and the process may be repeated. In this manner, a patient can receive Bi-PAP ventilation (peak inspiratory pressure and positive end expiratory pressure) with superimposed oscillating airway pressures during both inhalation and exhalation cycles. In some embodiments, any number of valves and bubbler conduits can be used to alternate between any number of different mean airway pressures.

The angle of bubblers 980 and 985 may be altered between 0° and 180° to control the amplitude and frequency of airway pressure oscillations superimposed on top of the airway pressure wave form for both the inhalation and exhalation cycles. In some embodiments, more than two bubblers (or simple conduits) may be used. In other embodiments, the angles of the two or more bubblers may be substantially similar. In still other embodiments, the angles of the two or more bubblers may be different.

In some embodiments, the angle of one or more of the bubblers as measured with respect to a line normal to the surface of the fluid or with respect to a vertical axis is about 1° to 89° or about 91° to 180°, preferably about 100° to 170°. That is, in some embodiments, the angle of one or more of the bubblers as measured with respect to a line normal to the surface of the fluid or with respect to a vertical axis can be at least, equal to, greater than or any number in between about 1°, 2°, 3°, 4°, 5°, 6°, 7°, 8°, 9°, 10°, 11°, 12°, 13°, 14°, 15°, 16°, 17°, 18°, 19°, 20°, 21°, 22°, 23°, 24°, 25°, 26°, 27°, 28°, 29°, 30°, 31°, 32°, 33°, 34°, 35°, 36°, 37°, 38°, 39°, 40°, 41°, 42°, 43°, 44°, 45°, 46°, 47°, 48°, 49°, 50°, 51°, 52°, 53°, 54°, 55°, 56°, 57°, 58°, 59°, 60°, 61°, 62°, 63°, 64°, 65°, 66°, 67°, 68°, 69°, 70°, 71°, 72°, 73°, 74°, 75°, 76°, 77°, 78°, 79°, 80°, 81°, 82°, 83°, 84°, 85°, 86°, 87°, 88°, 89°, 91°, 92°, 93°, 94°, 95°, 96°, 97°, 98°, 99°, 100°, 101°, 102°, 103°, 104°, 105°, 106°, 107°, 108°, 109°, 110°, 111°, 112°, 113°, 114°, 115°, 116°, 117°, 118°, 119°, 120°, 121°, 122°, 123°, 124°, 125°, 126°, 127°, 128°, 129°, 130°, 131°, 132°, 133°, 134°, 135°, 136°, 137°, 138°, 139°, 140°, 141°, 142°, 143°, 144°, 145°, 146°, 147°, 148°, 149°, 150°, 151°, 152°, 153°, 154°, 155°, 156°, 157°, 158°, 159°, 160°, 161°, 162°, 163°, 164°, 165°, 166°, 167°, 168°, 169°, 170°, 171°, 172°, 173°, 174°, 175°, 176°, 177°, 178°, 179°, and 180°. In some embodiments, the angle of the bubblers as measured with respect to a line normal to the surface of the fluid or with respect to a vertical axis can be any angle that is not 0° or 90° so long as the device is configured to produce a high amplitude, low frequency broadband oscillating pressure wave having more than 50% of its average power spectra occur below about 10 Hz, 9 Hz, 8 Hz, 7 Hz, 6 Hz, 5 Hz, 4 Hz, 3 Hz, or 2 Hz when the bias gas flow is at least 2 L/min in a model test lung system comprising a hermetically sealed silastic lung within a calibrated plethysmograph.

Referring back to FIG. 1, the action of bubbles 190 escaping from the bubbler exit portion 180 serves to modulate the pressure of the gases in the patient ventilation system 100 which in turn modulates the pressure of the gases delivered to the patient's airway (not shown), which is connected to the patient interface 130. In general, gravity is a significant force by which gas pressures are modulated in the patient ventilation system 100. Gas flowing through the bubbler 170 must overcome the weight of the fluid column above the bubbler exit portion 180 to allow bubbles to escape, generating back pressure. As bubbles escape, they form a less dense, low pressure region above the bubbler exit portion, thereby reducing or even reversing the back pressure. Liquid (or fluid) can then rush back into the bubbler (gurgling) to generate greater back pressure and the cycle can repeat itself. The inertia of the liquid rushing back into the bubbler is reversed and accelerated back out the bubbler, generating air pressure oscillations in the conduit. The frequencies and amplitudes of the oscillations are controlled by: (1) the angle of the bubbler; (2) the bias gas flow rate; (3) the depth of the bubbler in the fluid (4) the length of the bubbler; (5) the diameter or cross-sectional area of the bubbler; and (6) the density of the fluid. The angle of the bubbler and the bias gas flow rate are significant features, which can be modulated to vary the amplitudes and frequencies of the oscillations.

More embodiments concern methods of using one or more of the aforementioned compositions to assist the breathing of a subject (e.g., an adult, child, infant human being or a mammal). By some approaches, a subject in need of breathing assistance is identified or selected and said subject is joined to one or more of the devices described herein. In some aspects the subject is attached to the device by nasal prongs and in other embodiments, the subject is attached to the device by facial or nasal masks, tube(s) placed in the nasal pharynx, endotracheal tubes, tracheostomy tubes, or combinations thereof. Once the subject and device are connected, gas flow is initiated. Preferable gas flows for infants are 1 to 10 L/min, whereas adults may require gas flows of 1 to 30 L/min and large mammals may require 1 to 100 L/min or more. Optionally, the frequency, amplitude of oscillating pressure, or volume of gas delivered is monitored so as to adjust the breathing assistance for the particular subject. By modulating the angle of the bubbler, the bias gas flow rate, or the depth of bubbler in the fluid, one may regulate the frequency and amplitude of the oscillations and these aspects may be automated in some embodiments (e.g., executable by a computer, software, and/or hardware). In some embodiments, a device having a particular length of bubbler, diameter or cross-sectional area of bubbler, or particular liquid density can be selected for a subject's unique needs. That is, in some embodiments, a patient in need of breathing assistance is selected or identified and a breathing assistance device, as described herein, is selected or identified according to a subject's age, size, or therapeutic need.

Preferred embodiments include a method for providing continuous positive airway pressure with oscillating positive end-expiratory pressure to a subject by providing any of the devices or apparatuses described herein, releasing gas from the gas source into the apparatus and delivering the gas to the subject. Other preferred embodiments include a method for increasing the volume of gas delivered to a subject by providing any of the breathing assistance devices or apparatuses described herein, adjusting the angle of the distal end of the conduit with respect to a vertical axis and releasing gas from the gas source into the apparatus to deliver gas to the subject. In some embodiments, the distal end of the conduit is adjusted to an angle greater than or equal to between about 91-170 degrees, between about 95-165 degrees, between about 100-160 degrees, between about 105-155 degrees, between about 110-150 degrees, between about 115-145 degrees, between about 120-140 degrees, between about 125-135 degrees, between about 130-140 degrees, or about 135 degrees with respect to a vertical axis. In other embodiments, the distal end of the conduit is adjusted to an angle of about 135 degrees with respect to a vertical axis. In yet other embodiments, the distal end of the conduit is adjusted to any angle, except 0 and 90 degrees, wherein the breathing assistance apparatus is configured to produce an oscillating pressure wave having more than 50% of its average power spectra occur below about 7 Hz when the bias flow of gas is at least 2 L/min in a model test lung system comprising a hermetically sealed silastic lung within a calibrated plethysmograph.

The patient ventilation systems described herein were evaluated in several bench tests and animal experiments. In one set of experiments, a model system was used to evaluate the performance of the embodiments described herein (Example 1). The silastic model lung test is a well accepted system to evaluate the performance of a breathing apparatus.

In another set of experiments, the patient ventilation system of FIG. 1 was evaluated in bench tests to determine the affect of the angle of the bubbler on the frequency bandwidth and amplitude composition of the pressure oscillations. It was discovered that the angle of the bubbler greatly affected both the frequency bandwidth and amplitude composition of the pressure oscillations (see Example 2).

In other experiments, the patient ventilation system of FIG. 1 was evaluated in bench tests to determine the affect of the angle of the bubbler on the frequencies and amplitudes of the pressure oscillations, as well as, the corresponding volume of gas delivered to the silastic lung model. It was discovered that the bubbler angle has an unexpected and profound influence on the amplitude of oscillations in airway pressure and volume delivered to the mechanical lung model (see Example 3).

In yet another experiment, the patient ventilation system of FIG. 1 was evaluated in bench tests to determine the affect of the bias gas flow rate on the amplitude of oscillations in airway pressure and lung volume delivered to the lung model. It was discovered that in general, as the bias flow rate increases, the amplitude of oscillations in airway pressure and lung volume delivered to the lung model also increase. Furthermore, surprising and unexpected results were obtained showing that the Funnel configuration used in Nekvasil, which yields the highest amplitudes in pressure oscillations, does not yield the highest amplitudes of gas delivered to the lung model (see Example 4).

In another set of experiments, the patient ventilation system of FIG. 1 was evaluated in bench tests to determine the affect of the depth of the bubbler in the fluid on the mean airway pressure and on the amplitude of airway pressure oscillations, given a constant angle, bubbler diameter, bubbler length and bias gas flow rate. It was discovered that, in general, the deeper the bubbler is in the fluid, the greater the mean airway pressure that is generated. It was also discovered that, for this embodiment, a depth between about 7 and 9 cm yielded the maximum amplitude of airway pressure oscillations (see Example 5).

In another set of experiments, the patient ventilation system of FIG. 1 was evaluated in bench tests to determine the affect of the length and diameter on the amplitude of airway pressure oscillations. It was discovered that, for this embodiment, a bubbler diameter of 1.5 cm and a bubbler length of 9 cm yielded the highest amplitudes of airway pressure oscillations (see Example 6).

In other experiments, the patient ventilation system of FIG. 1 was evaluated in bench tests to determine the affect of the angle of the bubbler on the amplitude and frequency characteristics of the power spectra derived from the airway pressure time signal. It was discovered that the angle of the bubbler had a great impact on the amplitude and frequency characteristics of the power spectra, especially for angles greater than 90° (see Example 7).

In another set of experiments, the patient ventilation system of FIG. 1 was evaluated in bench tests to determine the affect of the bias gas flow rate on the amplitude and frequency characteristics of the power spectra derived from the airway pressure time signal. It was discovered that the bias gas flow rate had a great impact on the amplitude and frequency characteristics of the power spectra (see Example 8).

In another set of experiments, the funnel as described in the Nekvasil reference (cited in the background section above) and the patient ventilation system of FIG. 1 were evaluated in bench tests to determine the amplitudes of the airway pressure oscillations and the delivered gas volume oscillations of each device. It was discovered that the Nekvasil funnel produced high amplitude pressure oscillations in a narrow frequency bands centered around 9 Hz and harmonics of 9 Hz, relatively independent of bias gas flow rates. It was also discovered that the Nekvasil funnel produced amplitude pressure oscillations with short time durations, leading to small volumes of gas being delivered to the model lung. In contrast, it was shown that patient ventilation system of FIG. 1 produced high amplitude, long time duration pressure oscillations in a broad band of frequencies resulting in large volumes of gas being delivered to the model lung (see Example 9).

In another set of experiments, the patient ventilation system of FIG. 1 was evaluated in live animal tests to determine the affect of the angle of the bubbler on oxygenation in the animals, as well as, to compare the effectiveness of the patient ventilation system of FIG. 1 to conventional mechanical ventilation. It was discovered that the angle of the bubbler had a profound effect on the oxygenation of the animals. It was also discovered that the patient ventilation system of FIG. 1 was more effective at oxygenating and ventilating the animals than the conventional mechanical ventilator (see Example 10).

In another set of experiments, the patient ventilation system of FIG. 1 was evaluated in live animal tests to determine the effectiveness of the ventilation system in comparison to conventional mechanical ventilation with respect to work of breathing, oxygenation and ventilation characteristics. It was discovered that the patient ventilation system of FIG. 1 had a positive and profound effect on the work of breathing, oxygenation and ventilation in the animals (see Example 11).

In other experiments, the patient ventilation system of FIG. 29 was evaluated in bench tests to compare the ventilation characteristics of the ventilation system with a common mechanical ventilator. It was discovered that the ventilation system of FIG. 29 produced a similar airway pressure profile as the mechanical ventilator, with the exception of superimposed oscillations in the airway pressure during both the inspiratory and expiratory cycles (see Example 12).

In another experiment, the patient ventilation system of FIG. 29 was evaluated in live animal tests to determine the effectiveness of the ventilation system in comparison to conventional mechanical ventilation with respect to oxygenation and ventilation. It was discovered that the patient ventilation system of FIG. 29 had a positive and profound effect on oxygenation and ventilation in the animals (see Example 13).

Example 1

Figure 2A:
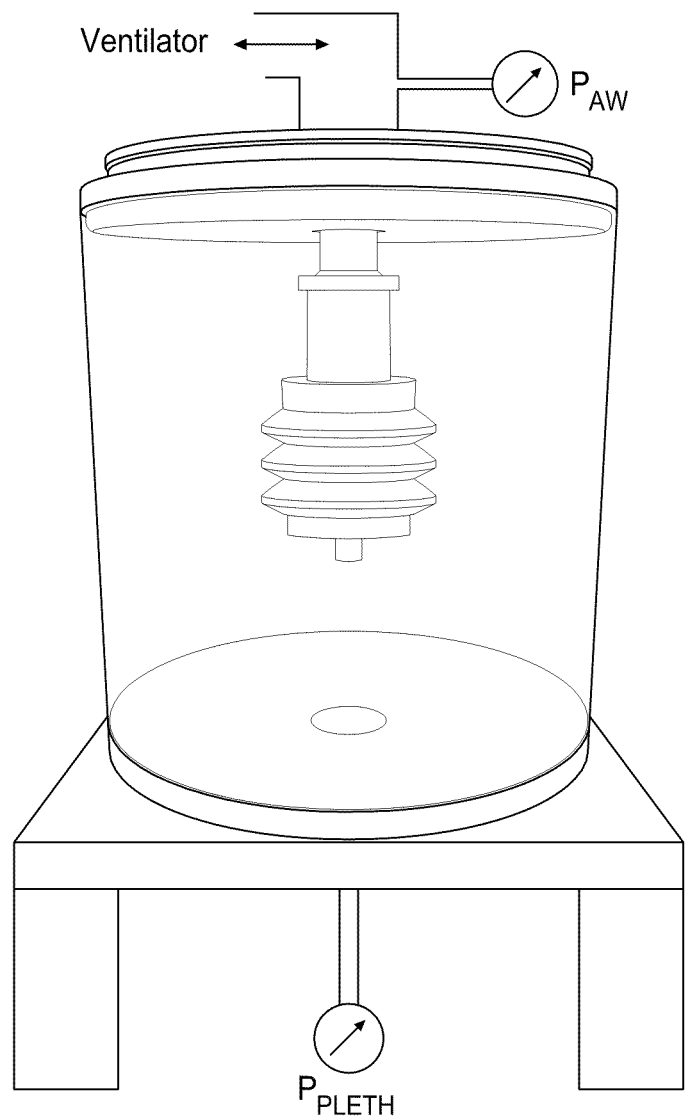
FIGS. 2A-B shows a silastic test lung model housed within a plethysmograph and a method for selecting oscillations in airway pressure for measurement.

This example describes the silastic test lung system, methods and experiments that were performed to calculate the embodiments described herein in this model system. FIG. 2A shows the model test lung (hermetically sealed within a calibrated plethysmograph) that was used to bench test the patient ventilation system 100 of FIG. 1. Steel wool (not shown) can also be used to surround the silastic lung within the plethysmograph to maintain near isothermal conditions. The plethysmograph pictured in FIG. 2A was purchased from Ingmar Medical®. The silastic test lung was made by Maquet Critical Care (Test Lung 191 63 01 720 E380E). Unless stated otherwise, the lung compliance is set to about 0.47 mL/cmH$_2$O and the airway resistance is set to about 200 cmH$_2$O/L/Sec. In some embodiments, an infant head model (with an internal volume of about 300 mL, including connectors) with Hudson nasal prongs (not shown) was connected to the silastic lung model and leak rates around the nasal prongs were measured at about 1.2 and 2.0 L/min at pressures of 5 and 10 cmH$_2$O respectively. Pressures at the airway (proximal to the nasal prongs) and inside the plethysmograph were measured using Honeywell® XRA515GN temperature compensated pressure sensors. Signals from the pressure sensors were recorded on a desktop computer via a DataTranslation DT9804-EC-I-BNC analog/digital converter. The sample frequency was 1024 Hz and the sample period was 8 seconds. The first 100 msec of data were left unfiltered in order to obviate the initial deviations caused by the filtering.

The plethysmograph was calibrated by adding known volumes of 5, 10, 15 and 20 mL to the lung model using a glass syringe and recording the pressure inside the plethysmograph. The volumes were plotted as a function of pressure and a linear regression through the data gave a calibration factor of 1.8 mL/cmH2O. The pressure transducers were calibrated using a two point calibration. The system was open to atmospheric pressure for a zero calibration. Pressure was then applied to the pressure transducers and measured using a calibrated manometer (Digitron® Model PM-23). The pressures were recorded digitally using the A/D converter and averaged over two seconds of readings while sampled at 1000 Hz resulting in zero and slope calibration factors.

Figure 2B:
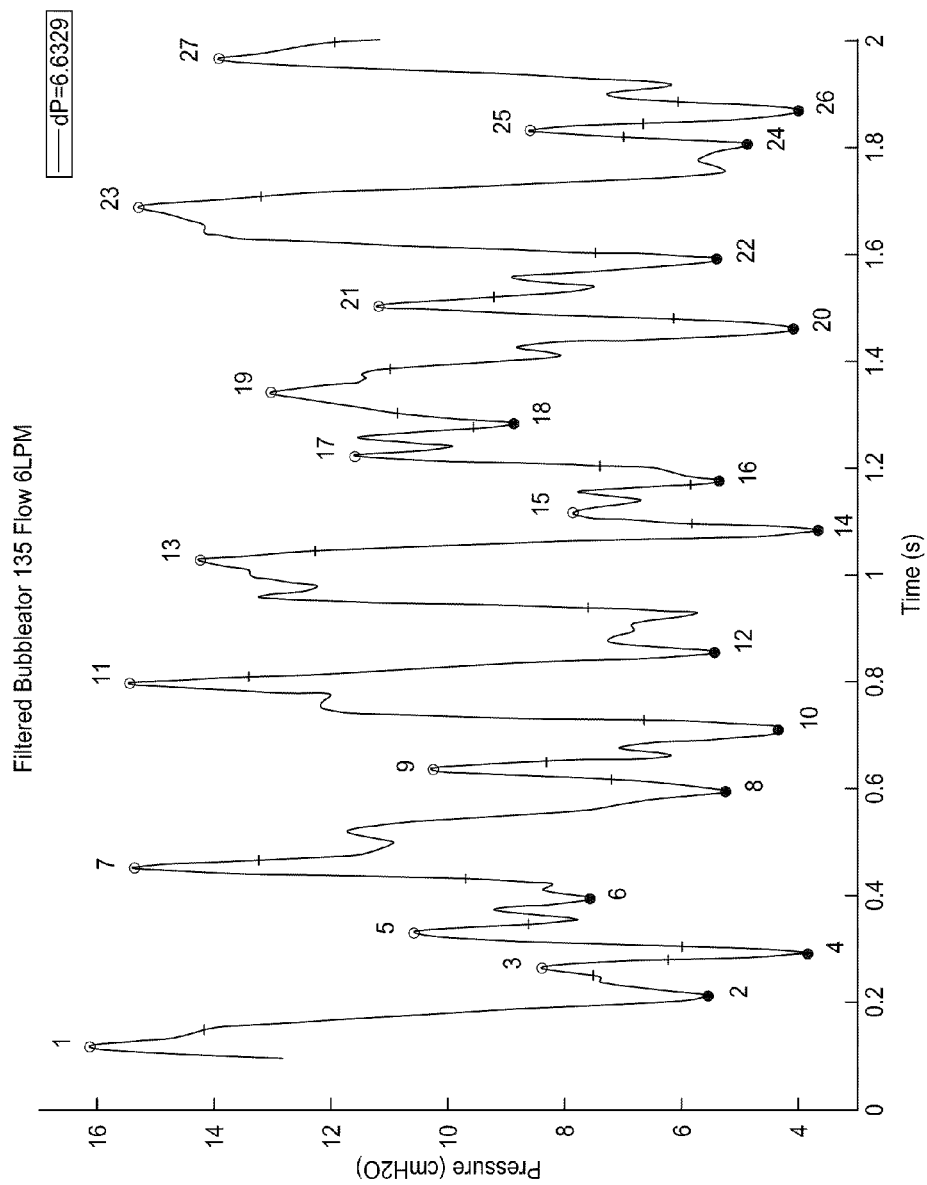

The amplitudes of oscillations in airway pressure were calculated from the airway pressure signal. The pressure signals were filtered using a low-pass $4^{th}$ order Butterworth filter with a cut-off frequency of 50 Hz prior to the amplitude analyses. A minimum threshold change in volume was established by calculating 15% of the absolute maximum and minimum of the 8 second period of airway pressures and local maxima and minima on the signal were found by stepping through the data. For example, in FIG. 2B a local maxima is found at point 1. Stepping forward in time through the data one passes the plus sign indicating the 15% threshold. Stepping further, point 2 is found. Stepping even further toward point 3, the threshold plus sign is passed indicating that point 2 is a minimum. Thus, point 1 is the peak and point 2 is the trough of an oscillation. Notice the small oscillation between points 5 and 6 that is not counted because the 15% threshold criterion was not met. The mean and standard error of the pressure oscillations were calculated for the period of 8 seconds of measurements. A similar process was used to determine the amplitude of oscillations in lung volume.

Example 2

Figure 3:
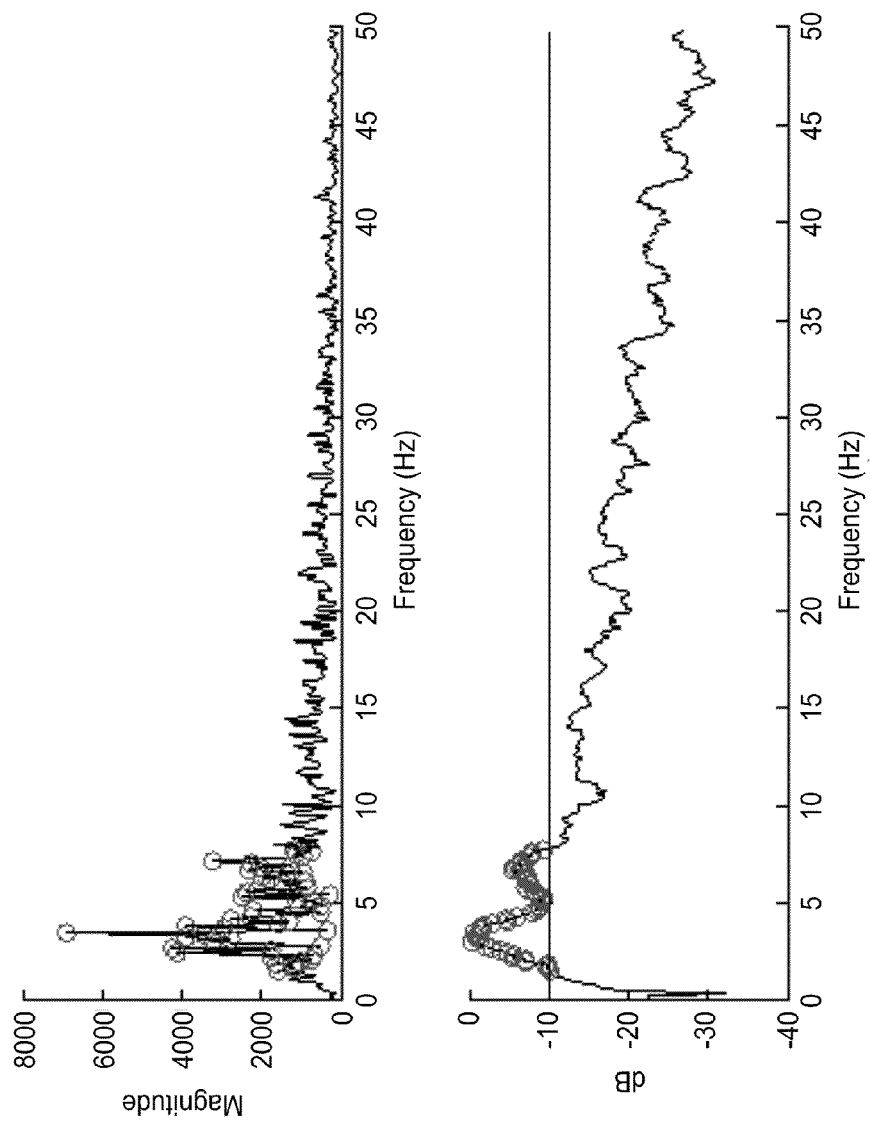
FIG. 3 demonstrates methods used to determine frequency band from a fast Fourier transformation of the original pressure signal.
Figure 4:
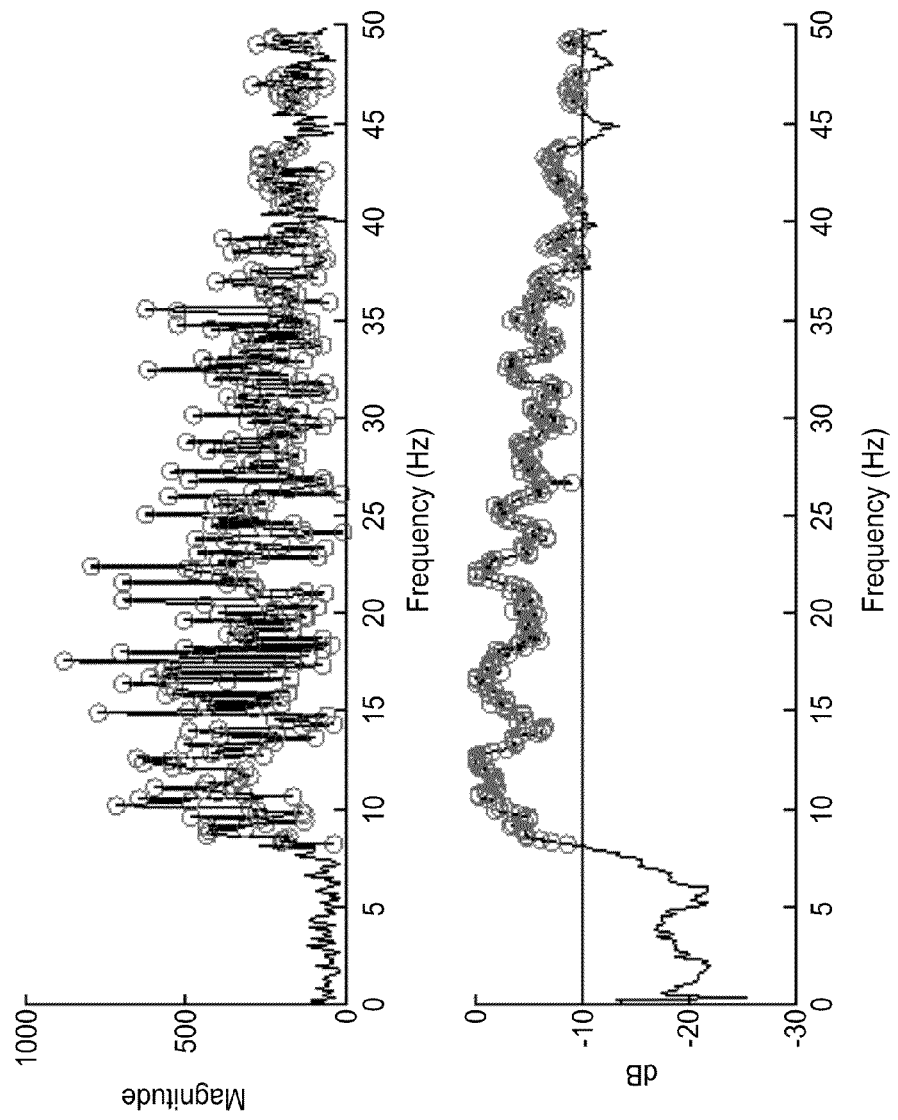
FIG. 4 shows how the frequency band was determined from another signal at different conditions from FIG. 3.

This example describes how the patient ventilation system of FIG. 1 was evaluated with a method (disclosed below) to determine the affect of the angle of the bubbler on the frequency bandwidth and composition of the pressure oscillations. To determine the bandwidth of the oscillation in airway pressure, the airway pressure-time waveform (unfiltered) was transformed into the frequency domain using fast Fourier transformation (FFT). The frequencies were then filtered using a 10-point boxcar. A relevant range of frequencies was defined as the longest set of contiguous frequencies with amplitudes greater than −7 dB relative to the peak magnitude. The magnitude of oscillations is the square root of the sum of the real and imaginary parts of the FFT each squared, with units of cmH$_2$O. Outlier frequencies that were more than 1 Hz away from the set of frequencies were not considered. The frequencies yielding the maximum power were also recorded. For example, FIGS. 3 and 4 show measurements made with the bubbler angle set to 135° and 0° respectively. At 135° the frequencies ranged from 2 to 7 Hz while at 0° the range was from 8 to 37 Hz. Note that the magnitude at 135° is much greater (around 4000) than at 0° (around 700) which is consistent with the greater amplitude of airway pressure oscillations measured at 135°.

Example 3

Figure 5:
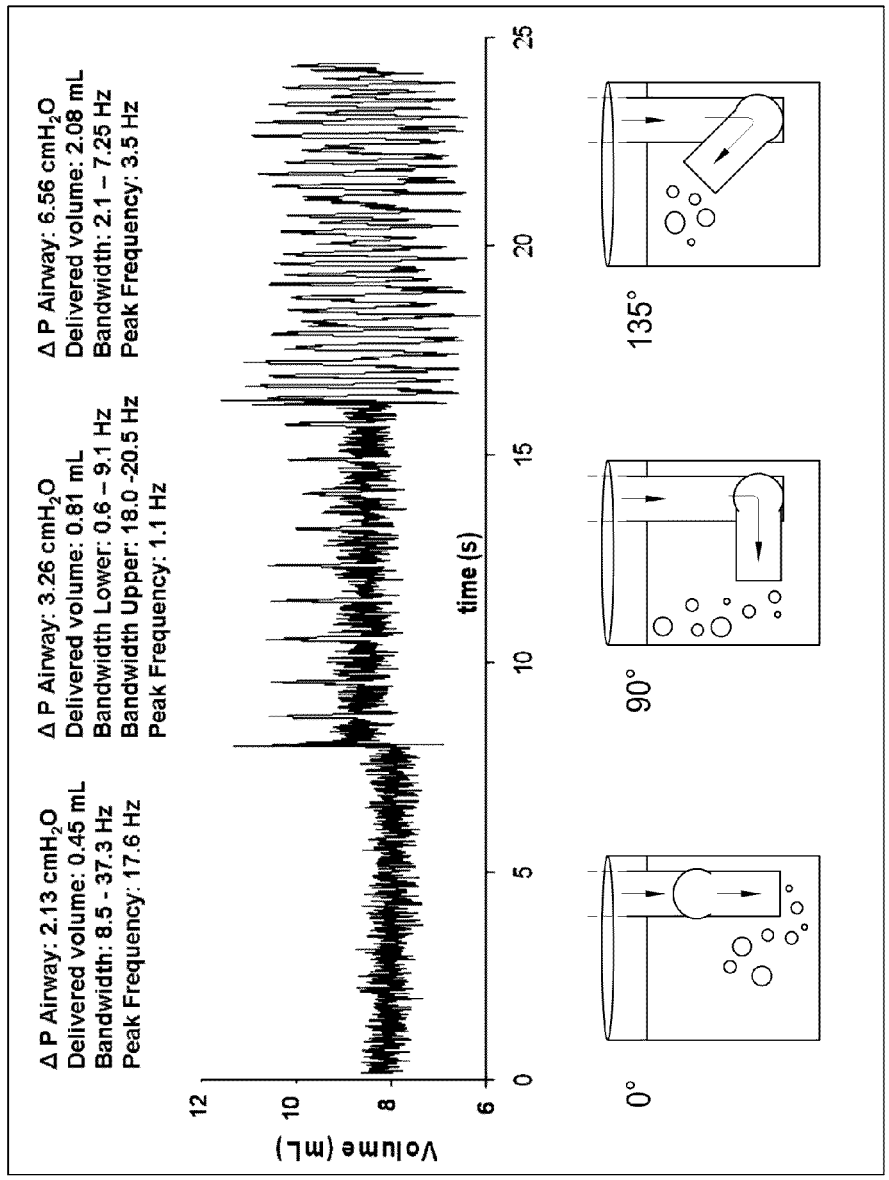
FIG. 5 depicts the delivered volume of gas to a test lung with different bubbler angles.

This example describes how the patient ventilation system of FIG. 1 was evaluated in bench tests to determine the affect of the angle of the bubbler on the frequencies and amplitudes of the pressure oscillations, as well as the corresponding volume of gas delivered to the silastic lung model. Referring to FIG. 5, three different bubbler angle configurations of 0°, 90° and 135° were used to illustrate the effect of the bubbler angle on pressure oscillations delivered to the silastic lung model (a constant bias flow of 6 L/min was used). When the bubbler angle is oriented vertically in the liquid (0° from the vertical to the water surface), only relatively high frequency, low-amplitude pressure oscillations are generated, resulting in very little gas being delivered to the lung. In this configuration, the system is similar to conventional B-CPAP. When the bubbler angle is adjusted horizontally (90° from the vertical and parallel with the liquid surface) both high and low frequency oscillations in pressure are obtained with the largest amplitudes in pressure oscillations occurring at about 1.1 Hz. When the bubbler angle is adjusted to 135°, the amplitude of the airway pressure oscillations increases dramatically, while maintaining a relatively low frequency profile. In this position, gas flowing through the tubing releases bubbles and periodically accelerates liquid up the tubing (gurgling) generating relatively large pressure oscillations at relatively low frequencies (2.1-7.25 Hz). For purposes of this application, low frequencies are generally defined as any frequency below about 10 Hz, desirably any frequency below about 7 Hz and preferably any frequency below about 5 Hz. This configuration (135°) delivers a much greater volume of gas to the lung than either of the other two angles. Thus, the bubbler angle has an unexpected and profound influence on the amplitude of oscillations in airway pressure and volume delivered to the mechanical lung model. FIG. 5 shows a 462% increase in oscillations in volume delivered to the mechanical lung model when the bubbler 170 angle was increased from 0° to 135°. The amplitude of oscillations in airway pressure also increased 308% when the bubbler 170 angle was increased from 0° to 135°.

Figure 6:
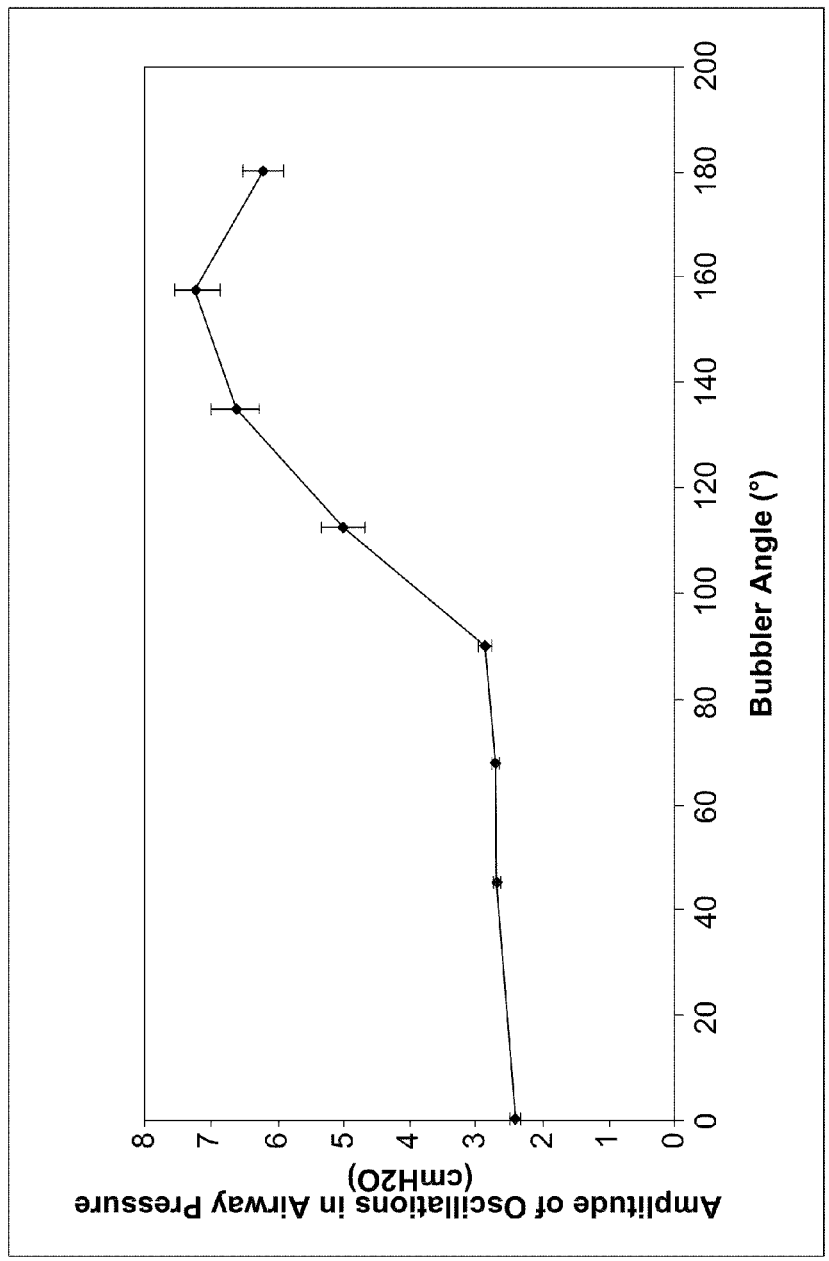
FIG. 6 illustrates how the amplitudes of oscillations in airway pressure vary with bubbler angle.
Figure 7:
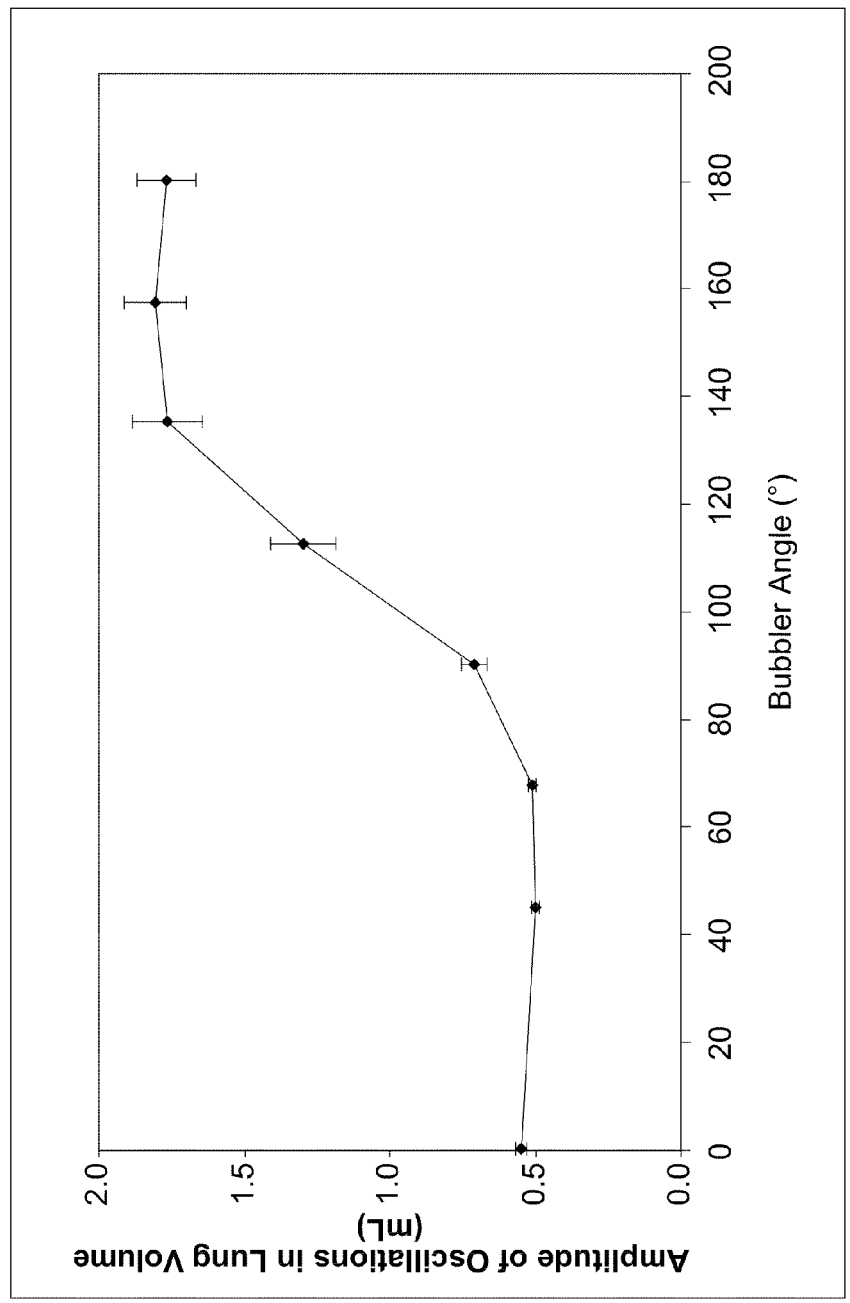
FIG. 7 depicts how the amplitudes of oscillations in lung volume vary with bubbler angle.
Figure 8:
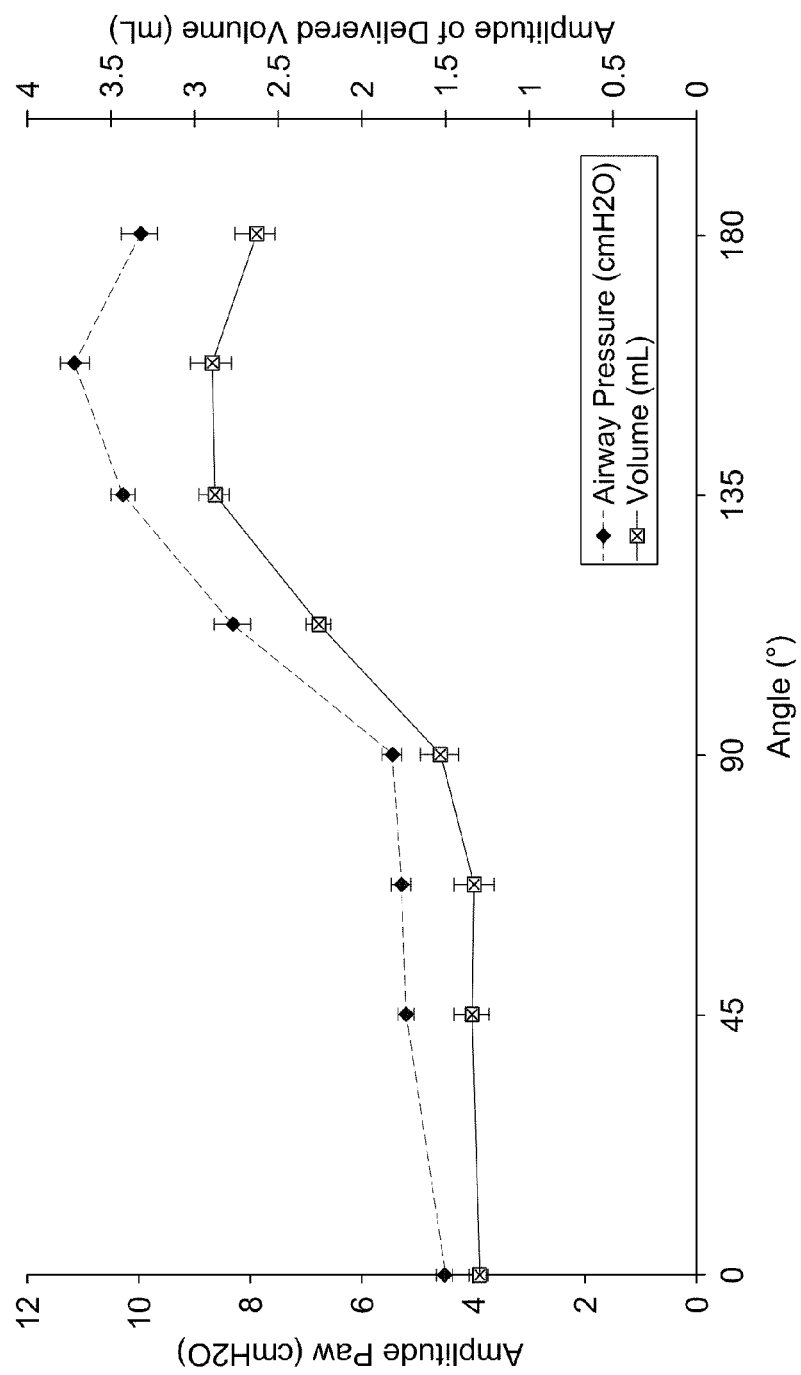
FIG. 8 shows how the amplitudes of oscillations in airway pressure and lung volume vary with bubbler angle in a different embodiment.

FIGS. 6 and 7 illustrate how the amplitude of oscillations in airway pressure and lung volume can change for various bubbler angles between 0° and 180°, given a constant bias flow rate. FIG. 8 shows how the amplitude of oscillations in airway pressure and lung volume vary for bubbler angles between 0° and 180° for a patient ventilation system having another constant bias flow rate.

Example 4

Figure 9:
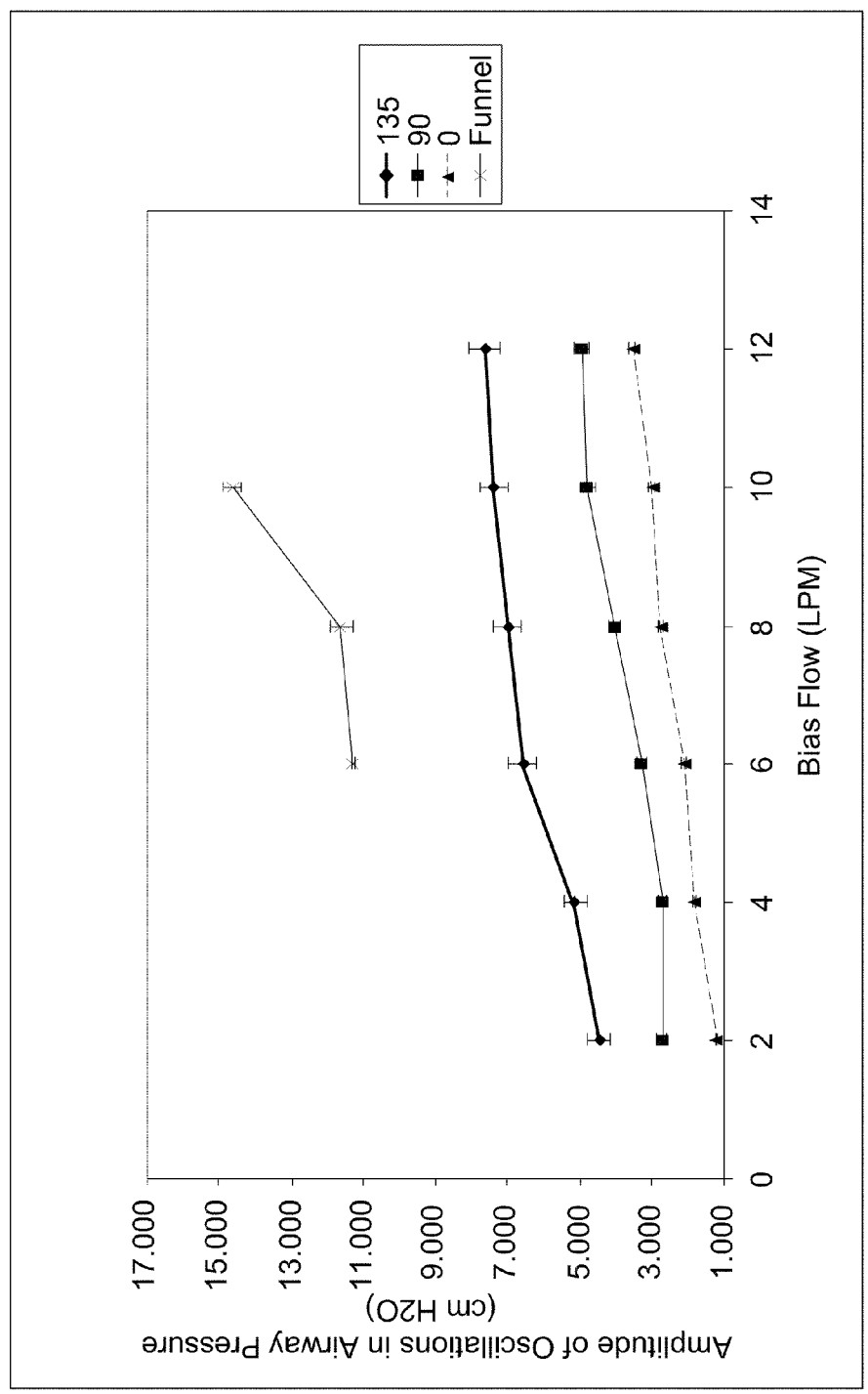
FIG. 9 demonstrates how the amplitudes of oscillations in airway pressure vary with different bias flow rates for different bubbler angles.
Figure 10:
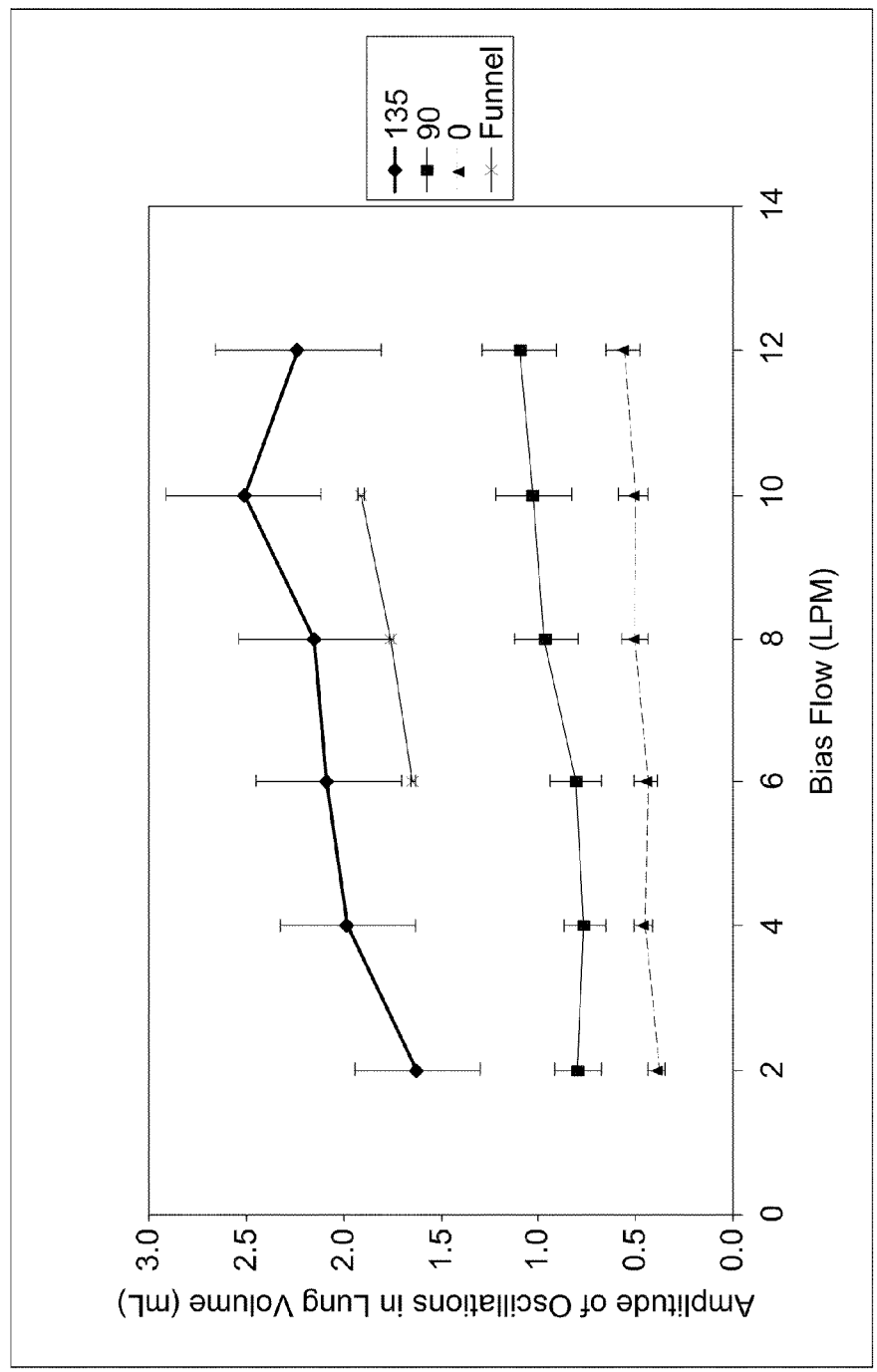
FIG. 10 illustrates how the amplitudes of oscillations in lung volume vary with different bias flow rates for different bubbler angles.

This example describes how the patient ventilation system of FIG. 1 was evaluated in bench tests to determine the affect of the bias gas flow rate on the amplitude of oscillations in airway pressure and lung volume delivered to the lung model. FIG. 9 demonstrates the typical effects of bias flow on the amplitude of oscillations in airway pressure for bubbler angles of 0°, 90° and 135°, as well as, for a funnel-shaped bubbler exit portion oriented at 90°. In general, the greater the bias flow, the greater the amplitude of oscillations in airway pressures. Upon first inspection of FIG. 9, it appears that the funnel shaped bubbler exit portion oriented at 90° should deliver the most volume to the lung given the fact that this configuration yields the largest amplitudes in pressure oscillations at the airway. However, surprising and unexpected results were observed when measuring the amplitude of oscillations in lung volume. FIG. 10 shows the amplitude of oscillations in lung volume corresponding to the amplitudes of airway pressures in FIG. 9. Note that, while the funnel has by far the largest amplitudes of airway pressures in FIG. 9, the bubbler oriented at 135° has the greatest amplitudes of oscillations in lung volume. In order to understand this unexpected result, a more in-depth analysis of all of the variables affecting the system was made.

Referring back to FIG. 5, it was discovered that the relationships between amplitude, frequency and time duration of pressure waves control the amount of gas delivered to the lung. Specifically, large amplitude, low frequency, and relatively long time duration pressure oscillations deliver the most volume of gas to the lung. The time duration of a pressure oscillation is defined by the amount of time it takes for the oscillation to complete one cycle (minima→maxima→minima). For example, in FIG. 5 with the bubbler adjusted to 90°, there is a relatively large amplitude oscillation wave having a frequency of about 1.1 Hz. However, note the small time duration of the 1.1 Hz oscillation compared to the larger time duration of the pressure wave when the bubbler angle is set to 135°. An oscillating pressure wave with longer time duration has more time to deliver gas to the lung, and therefore results in more gas delivered to the lung.

Example 5

This example describes how the patient ventilation system of FIG. 1 was evaluated in bench tests to determine the affect of the depth of the bubbler in the fluid on the mean airway pressure and on the amplitude of airway pressure oscillations, given a constant angle, bubbler diameter, bubbler length and bias gas flow rate. Continuing with reference to FIGS. 1 and 5, the depth of the bubbler exit portion in the liquid controls the lower or mean airway pressure delivered to the lung. This creates a baseline offset in pressure and lung volume to which the pressure oscillations are essentially added to or superimposed upon. Accordingly, the mean airway pressure delivered to the patient can be controlled by adjusting the depth at which the bubbler 170 is placed beneath the fluid surface 166. In general, the deeper the bubbler is placed beneath the fluid surface 166, the greater the mean airway pressure delivered to the patient. In one embodiment, the depth of the bubbler 170 in the fluid is controlled by adjusting the length and/or orientation of the bubbler conduit 140 to adjust the depth at which the bubbler 170 is placed beneath the fluid surface 166. In another embodiment, the depth of the bubbler 170 in the fluid is controlled by moving the container 160 relative to the bubbler 170 to adjust the depth at which the bubbler 170 is placed beneath the fluid surface 166. In yet another embodiment, the depth of the bubbler 170 in the fluid is controlled by adjusting the fluid surface 166 relative to the bubbler 170, by adding or removing fluid from the container 160.

Figure 11:
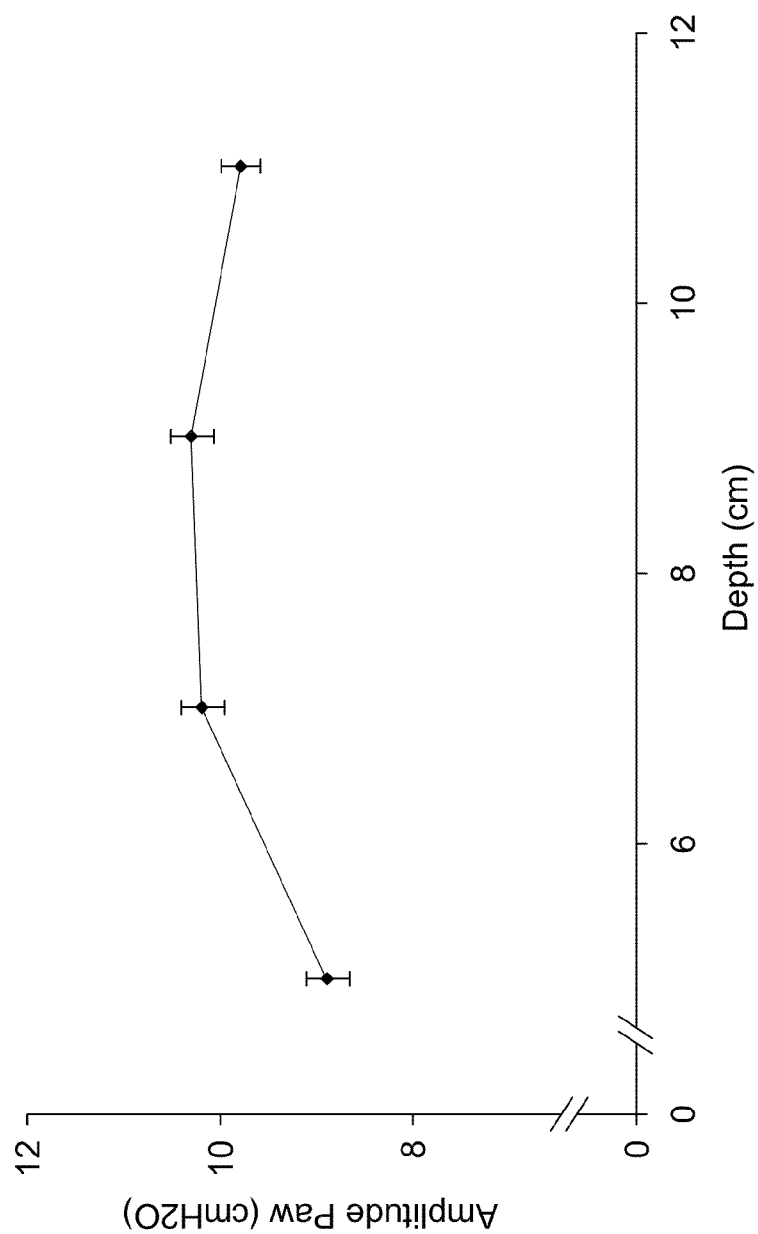
FIG. 11 shows how the depth of the bubbler in a fluid affects the amplitude of oscillations in airway pressure.

The depth of the bubbler in the fluid also affects the amplitudes of the oscillation in airway pressure. FIG. 11 illustrates one embodiment with the bubbler 170 set to 135°, at a bias gas flow rate of 6 L/min. The depth of the bubbler beneath the water surface was varied between 5 and 11 cm. The amplitude of oscillations in airway pressure, corresponding to depths of 5, 7, 9, and 11 cm, yielded airway pressures of 8.9±1.3, 10.2±1.2, 10.3±1.3, and 9.8±1.1 cmH2O, respectively (mean±SD, n=32).

Example 6

Figure 12:
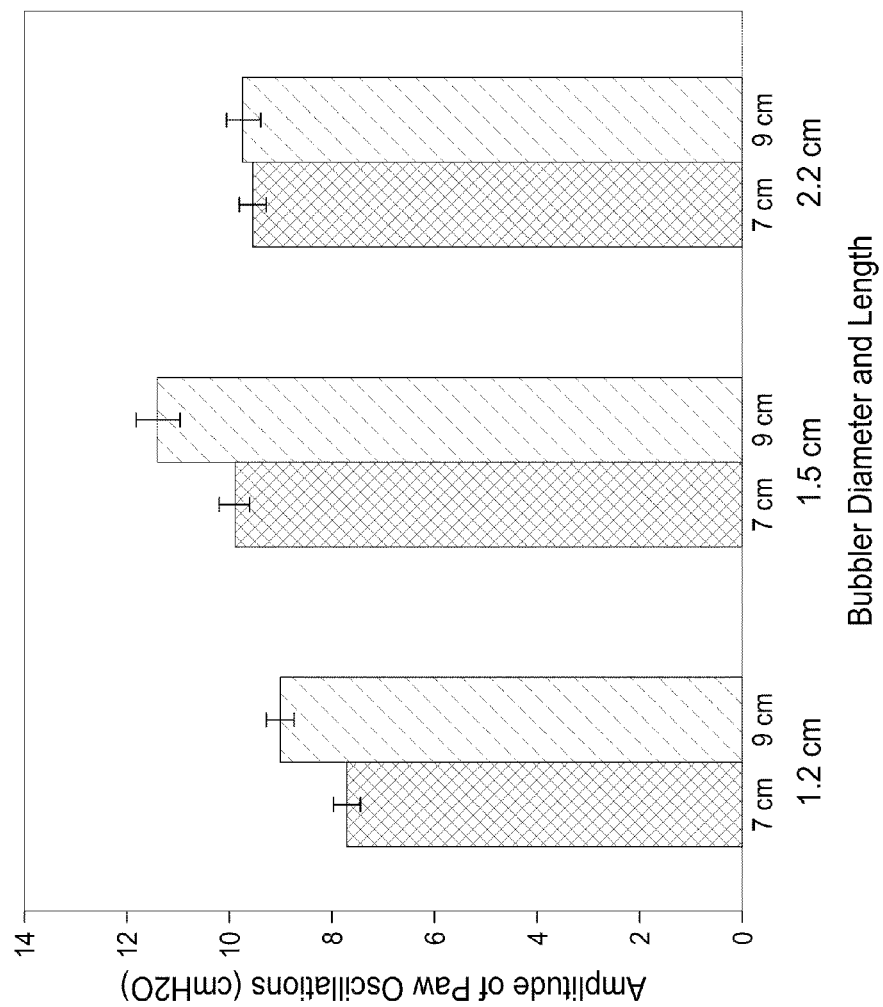
FIG. 12 shows how the bubbler diameter and length affect the amplitude of oscillations in airway pressure.

This example describes how the patient ventilation system of FIG. 1 was evaluated in bench tests to determine the affect of the length and diameter on the amplitude of airway pressure oscillations. The geometric shape of the bubbler and bias flow rate influence the rate at which bubbles break up as they travel through and exit the bubbler. In the typical case of using round tubing for the bubbler, the diameter and length of the bubbler are the major bubbler geometric factors that influence the amplitude of oscillations in airway pressure. FIG. 12 shows how the amplitude of airway pressures change as the inside diameter of the bubbler is varied from 1.2 cm to 2.2 cm and the length of the bubbler is varied between 7 and 9 cm (the bias flow was held constant at 6 L/min). In this embodiment, the optimal geometric dimensions for the bubbler are 1.5 cm diameter and 9 cm length.

Example 7

Figure 13:
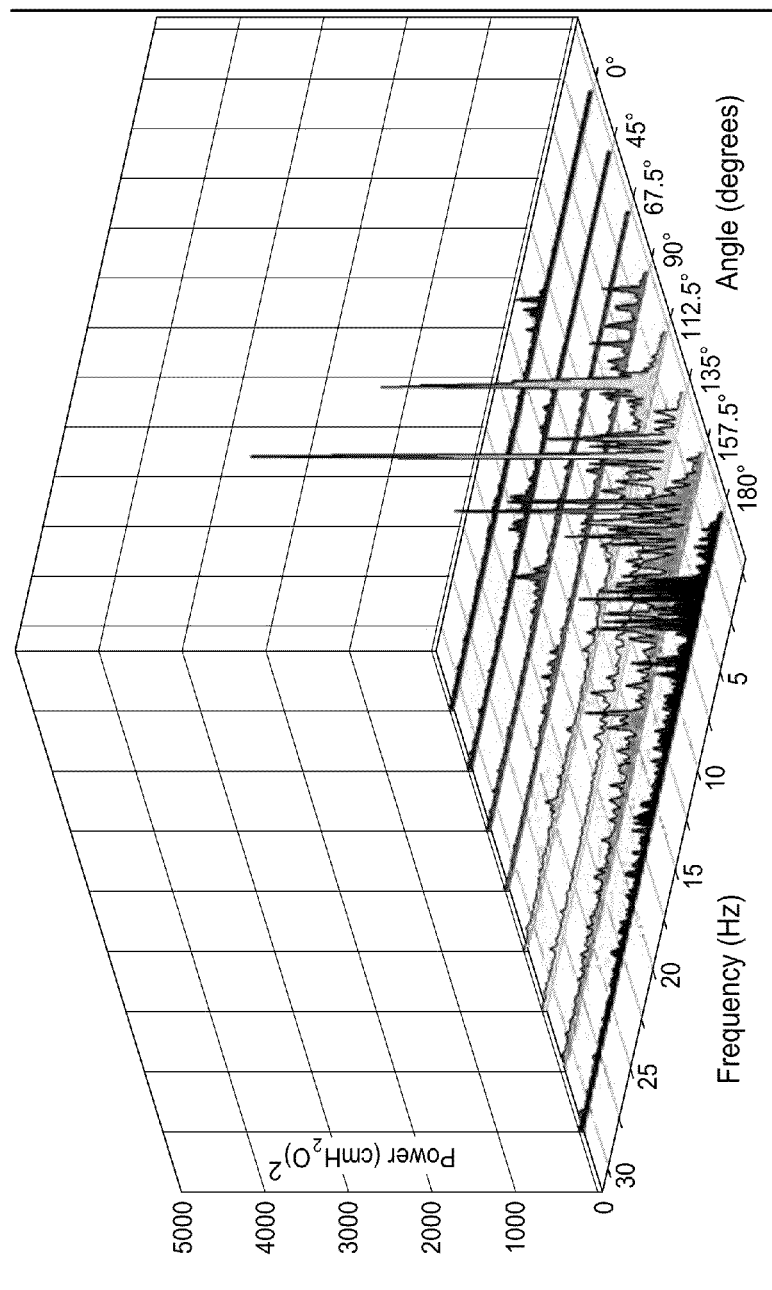
FIG. 13 illustrates how the power spectra vary with frequency and angle.

This example describes how the patient ventilation system of FIG. 1 was evaluated in bench tests to determine the affect of the angle of the bubbler on the amplitude and frequency characteristics of the power spectra derived from the airway pressure time signal. The frequency spectrum and range of oscillations is also greatly affected by the angle of the bubbler, as can be seen in FIG. 13. The angle of the bubbler was varied between 0° and 180° and the airway pressure time signal was measured at each of the angles shown in FIG. 13. Fourier analyses were performed on each of these airway pressure signals to find the power spectra characteristics for each airway pressure signal, as can be seen in FIG. 10, demonstrating an increase in frequency range and power when the bubbler angle is increased from 0° to 180°, with the maximum power amplitude occurring at about 135°. Furthermore, note the broad range of frequencies for the power spectral signals at angles greater than 90°. This broadband range of frequencies helps recruit and stabilize atelectatic (closed) alveoli in a patient.

Example 8

This example describes how the patient ventilation system of FIG. 1 was evaluated in bench tests to determine the affect of the bias gas flow rate on the amplitude and frequency characteristics of the power spectra derived from the airway pressure time signal. Bias flow alters the frequency range of the oscillations, with higher bias flows shifting the frequency spectrum toward higher frequencies and lower bias flows shifting the frequency spectrum toward lower frequencies.

Figure 14:
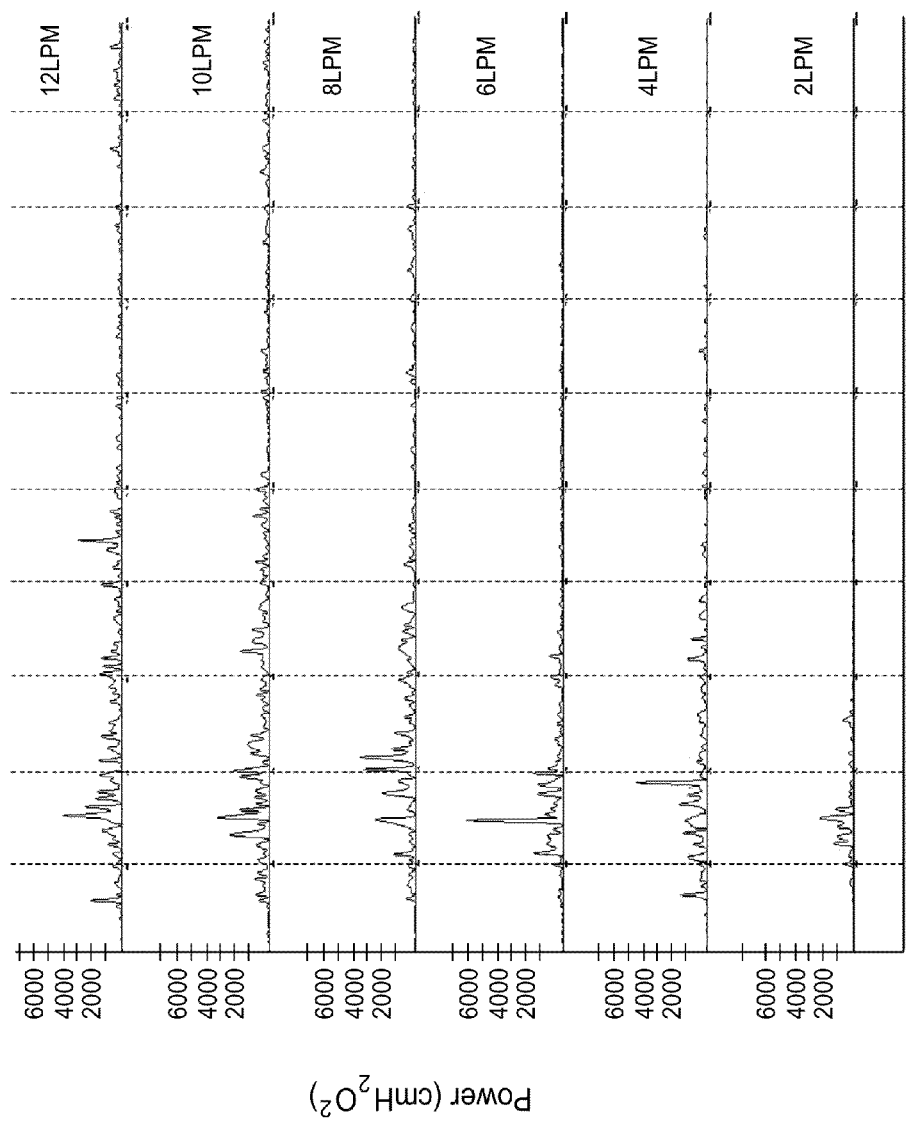
FIG. 14 demonstrates how the power spectra vary with bias flow rate.

FIG. 14 shows how the power spectra vary in the frequency domain with different bias flow rates (the bubbler angle was held constant at 135°). The major range of oscillations increases from a range of about 2 to 5 Hz (bias flow of 2 L/min) to a range of 1 to 9 Hz (bias flow of 12 L/min). Thus, in general, higher bias flows lead to an increase in the magnitude and range of frequencies of oscillations.

Example 9

Figure 15:
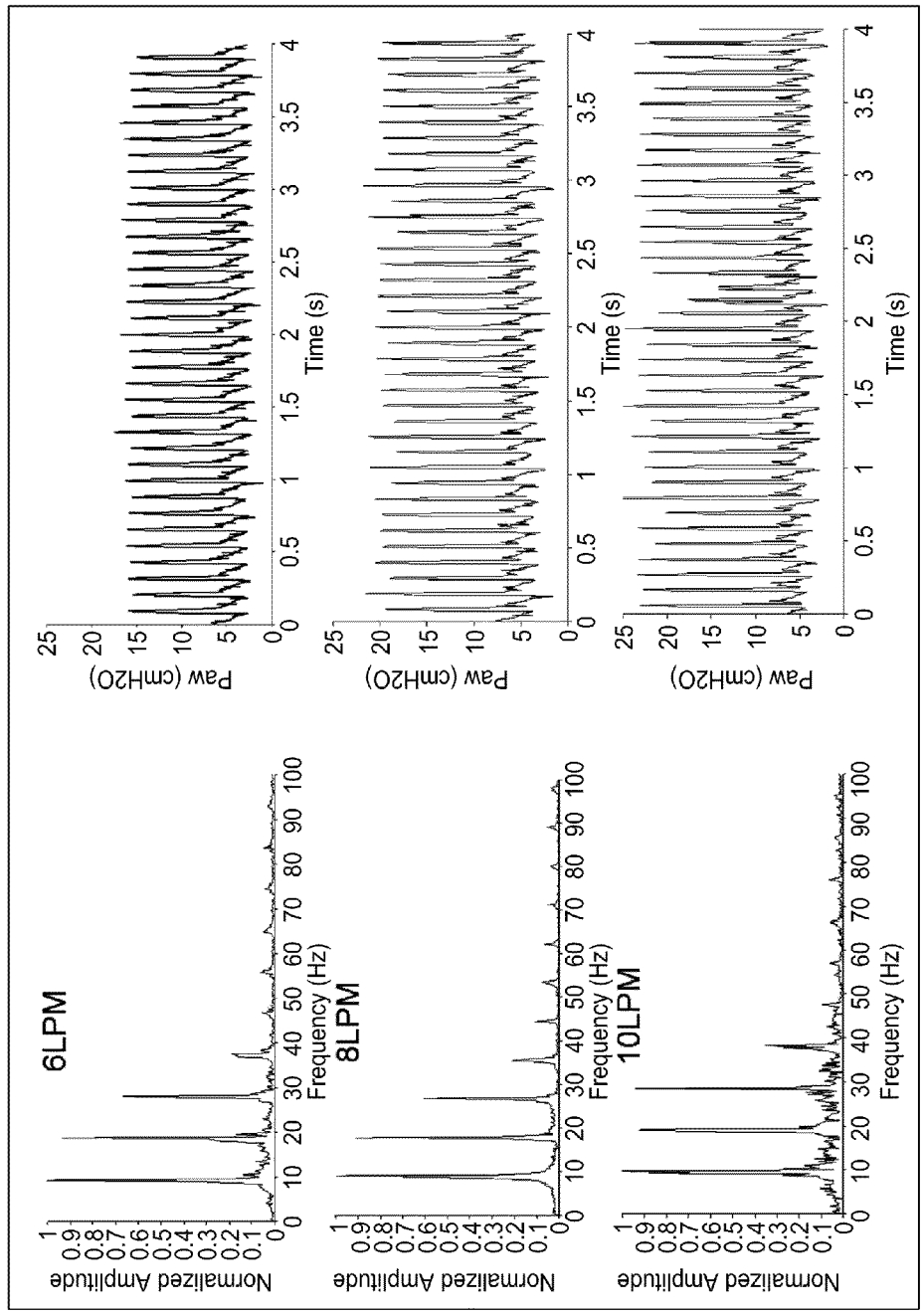
FIG. 15 shows how the normalized amplitude of the power spectra varies with different bias flow rates for a funnel shaped bubbler.

This example describes how the funnel, as described in the Nekvasil reference (cited in the background section above), and the patient ventilation system of FIG. 1 were evaluated in bench tests to determine the amplitudes of the airway pressure oscillations and the delivered gas volume oscillations of each device. In this experiment, a 30 mm funnel, identical to the one used in the Nekvasil reference, was affixed to the end of the bubbler. Measurements of airway pressures were obtained and analyzed in the frequency domain using FFT to determine the frequency composition of oscillations in Paw caused by bubbles exiting the funnel. FIG. 15 shows the normalized amplitude of the power spectra of airway pressure oscillations vs. frequency for 6, 8, and 10 L/min bias flow rates. FIG. 15 reveals that changes in bias flow affected the amplitudes of oscillations, while the frequencies of oscillation remained relatively constant and independent of bias flow. Note how consistent the airway pressure rises in time and the narrowness (short time duration) of the pressure spikes. Also, notice that the pressure wave form resembles a half sine wave. This is readily seen in the power spectral analysis where the major frequency of oscillation is around 9 Hz and the subsequent spikes are just harmonics of the 9 Hz, namely, 18, 27, 36, etc. Also, note that the amplitude in oscillations increases as bias flow increases, however, the frequency remains constant.

Figure 16:
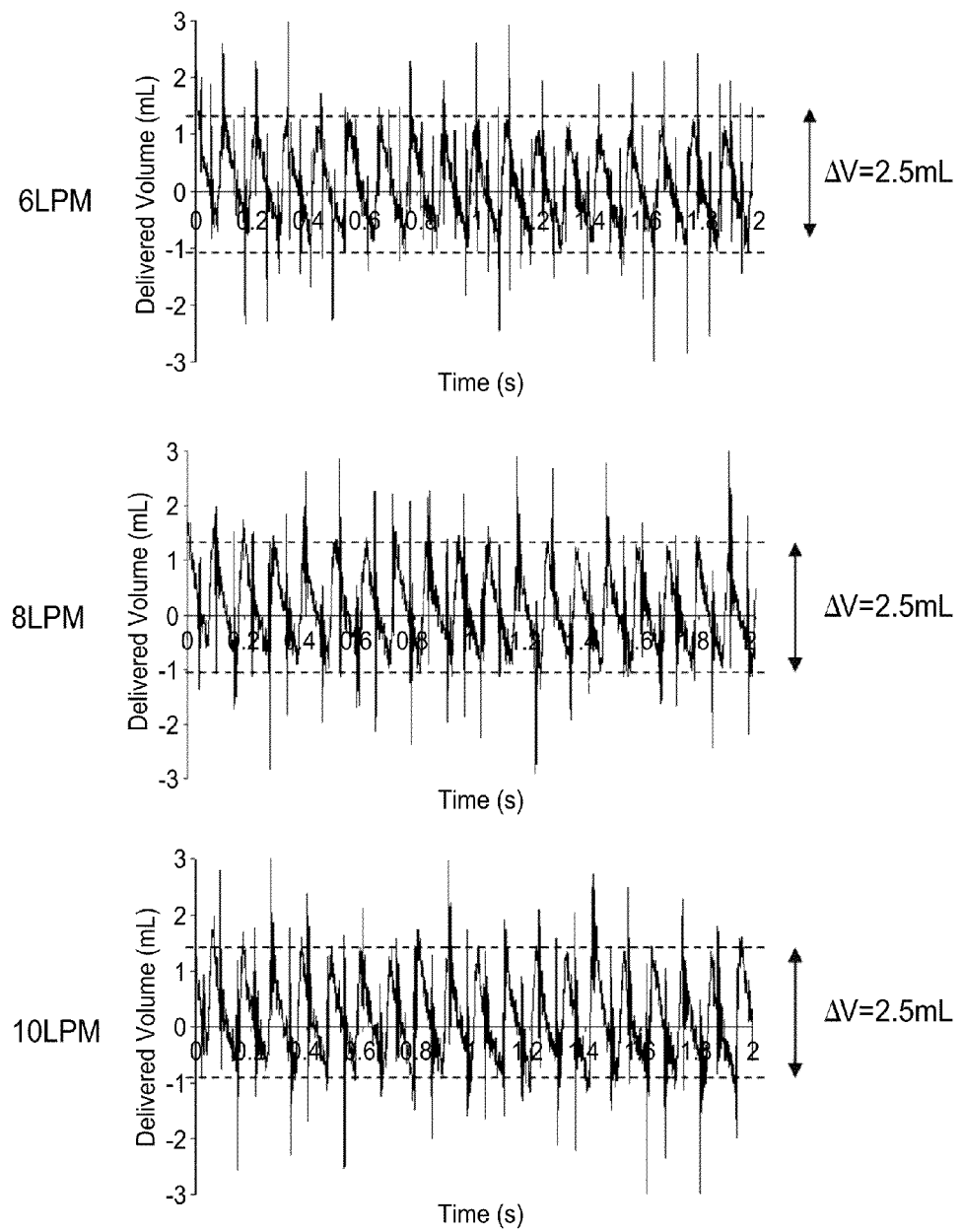
FIG. 16 shows the delivered lung volumes corresponding to different bias flow rates for a funnel shaped bubbler.
Figure 17:
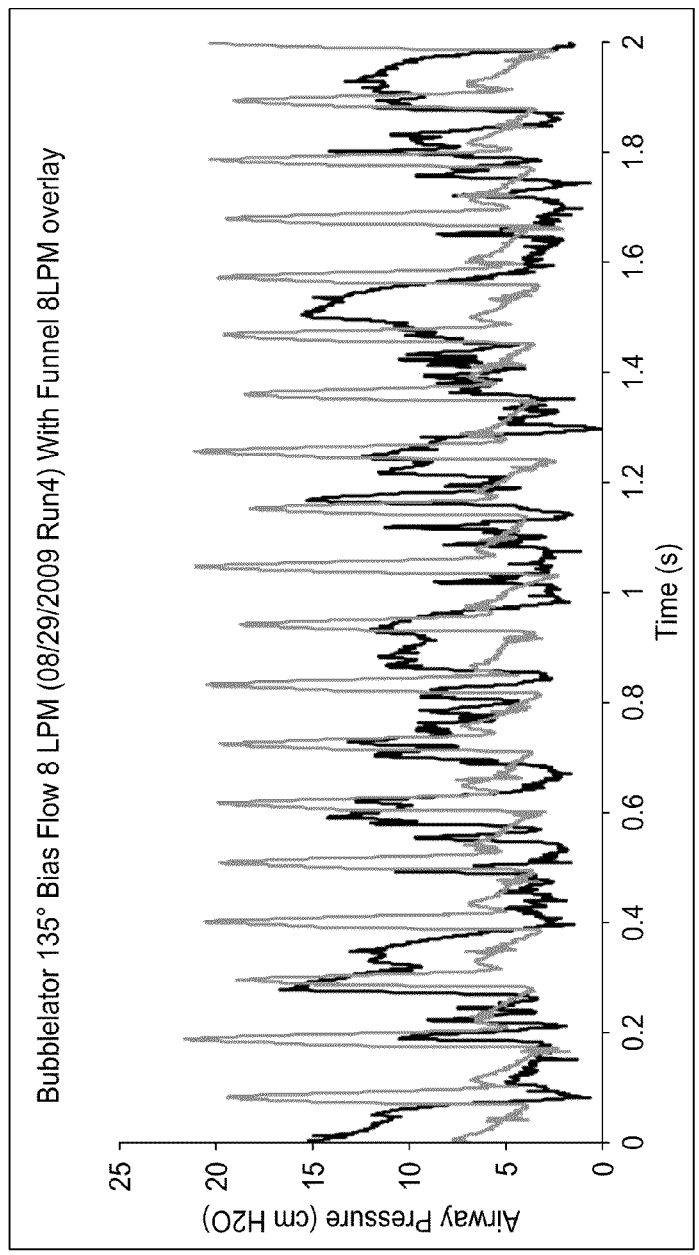
FIG. 17 shows the funnel data of FIG. 15 (gray) superimposed with oscillating airway pressure waves obtained from a bubbler set to 135° (black).

FIG. 16 shows how the volume of gas delivered to the lung model varied for each of the bias flow rates of FIG. 15. FIG. 16 shows that, even though the amplitude in airway pressure oscillations increased as bias flow increased, the volume of gas delivered to the lung model did not increase. This is due to the short time duration of the airway pressure spikes, which did not last long enough to push very much gas into the lung. This phenomenon is more evident in FIG. 17, which compares the airway pressure using the funnel (gray signal) with the airway pressure of the bubbler (black signal) adjusted to an angle of 135° without a funnel. Both measurements were taken with bias flow rates of 8 L/min. Note that the bubbler delivers pressures with a greater time duration resulting in larger volumes of gas delivered to the patient. The oscillations in pressure delivered by the funnel are shorter in duration than the bubbler and the funnel delivers only about 60% of the tidal volume delivered by the bubbler.

Figure 18:
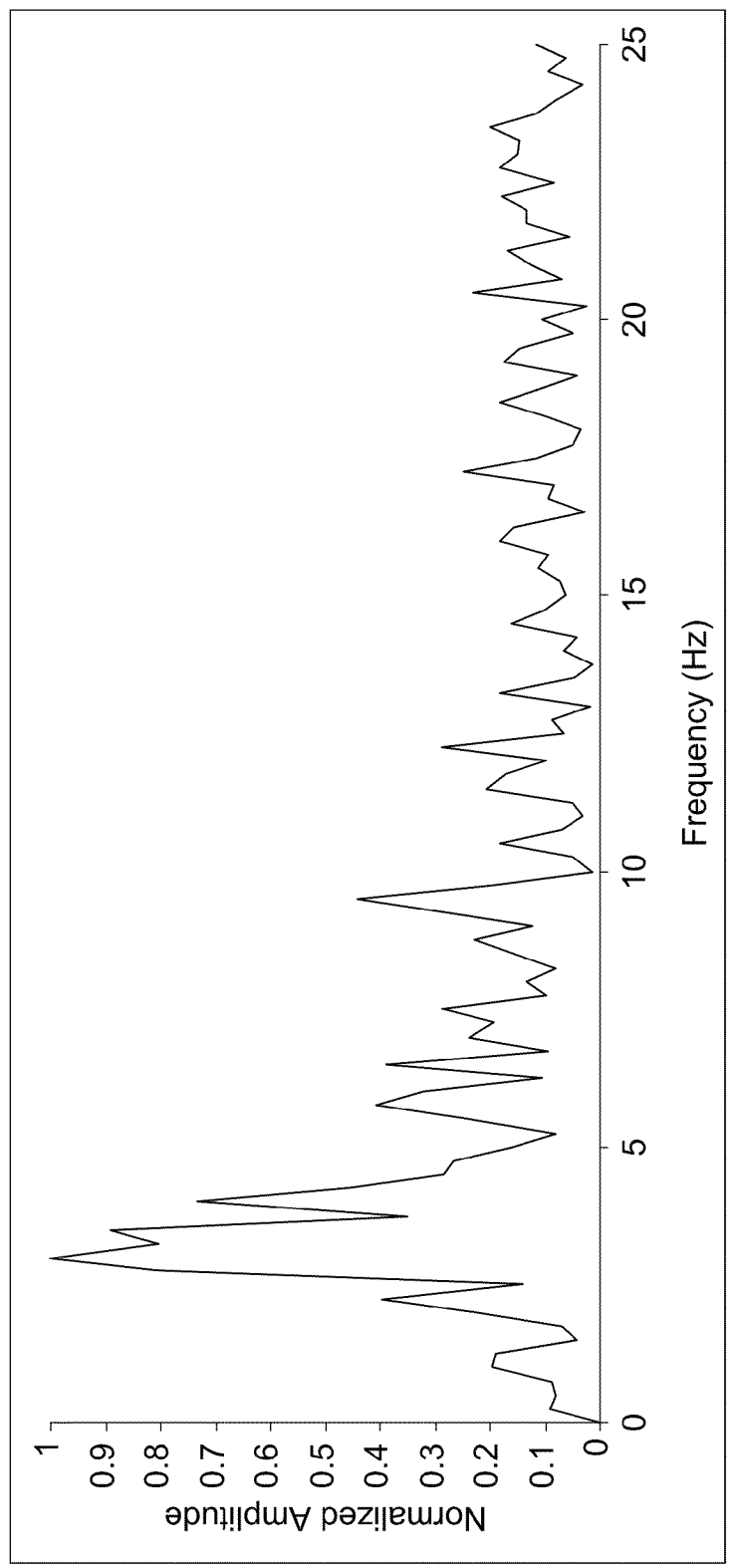
FIG. 18 shows how the normalized amplitude of the power spectra varies with different bias flow rates for a bubbler set to 135°.

FIG. 18 shows the normalized amplitude of the power spectra of airway pressure oscillations vs. frequency for the bubbler adjusted to an angle of 135°, without a funnel and with an 8 L/min bias flow rate. Note the broad-band nature of the power spectra in FIG. 18 compared to the narrow band power spectra in FIG. 15. This is considered to be good for recruiting and maintaining collapsed alveoli, as previously discussed.

Figure 19:
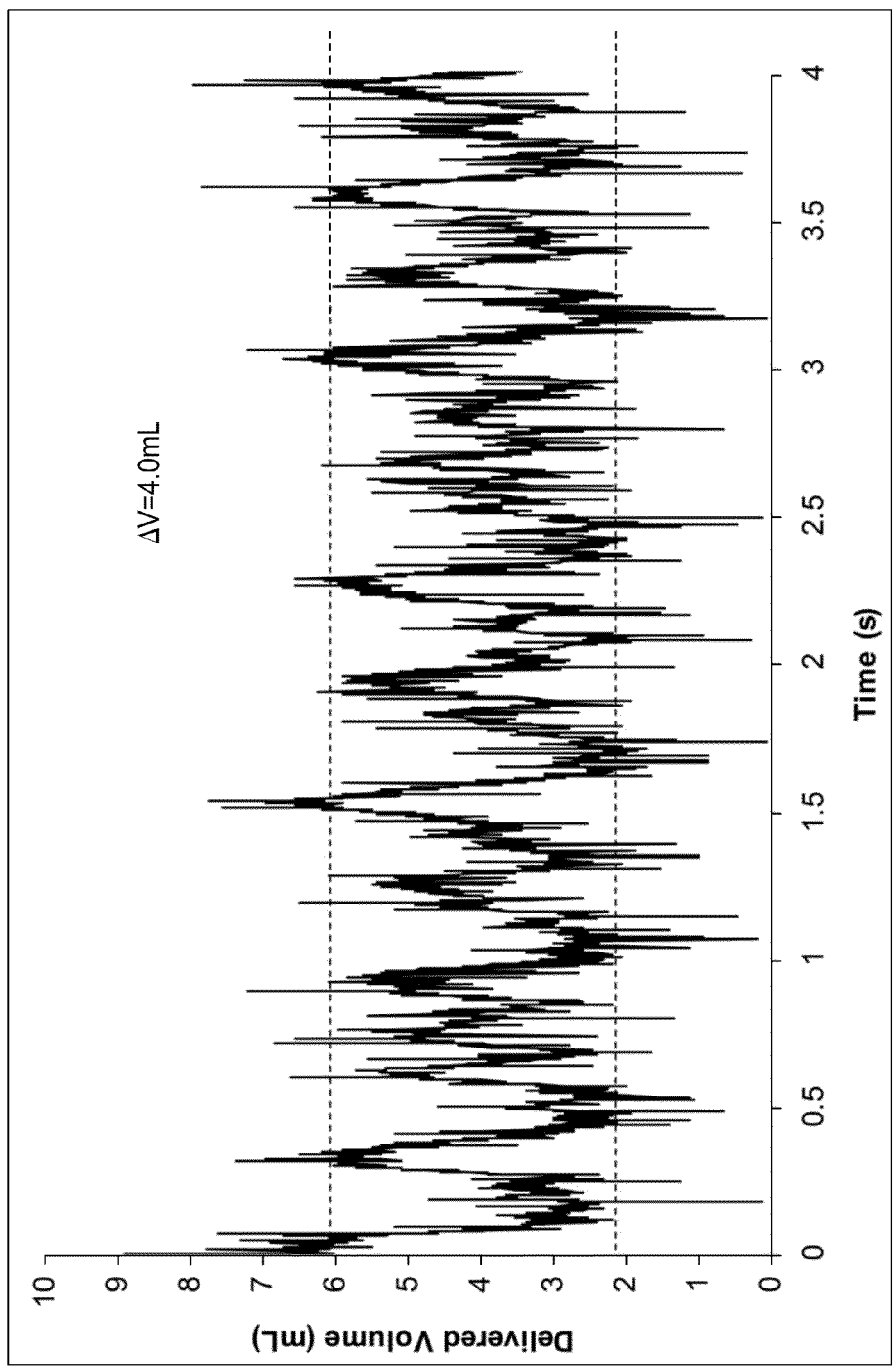
FIG. 19 illustrates the delivered lung volume for a given bias flow rate for a bubbler set to 135°.

FIG. 19 shows the delivered gas volume in time for the bubbler at 135° at 8 L/min discussed above. Dashed Lines represent maximum and minimum volumes representing an average volume delivered to the lung of 4.0 mL, which is larger than the volume delivered by the funnel (FIG. 16). Also, note that the signal of FIG. 19 has larger variations in size and frequency of oscillations in volume compared to the funnel.

Example 10

This example describes how the patient ventilation system of FIG. 1 was evaluated in live animal tests to determine the affect of the angle of the bubbler on oxygenation in the animals as well as to compare the effectiveness of the patient ventilation system of FIG. 1 to conventional mechanical ventilation. In this experiment, New Zealand White rabbits were used to study the effects of the "Bubbleator" CPAP on oxygenation of arterial blood (PaO2) and removal of carbon dioxide (PaCO2) from arterial blood. Thirteen rabbits were sedated, anesthetized, paralyzed and a tube was placed in their trachea (intubation). The animals were stabilized and managed by ventilating them on a conventional mechanical ventilator (CV). The animals were paralyzed to prevent them from breathing spontaneously so measurements of the effects of the Bubblelator on gas exchange in the lungs could be obtained independent of breathing. Measurements were made while the animals were managed on CV and the Bubblelator with bubbler angles of 0°, 90° and 135°.

Figure 20:
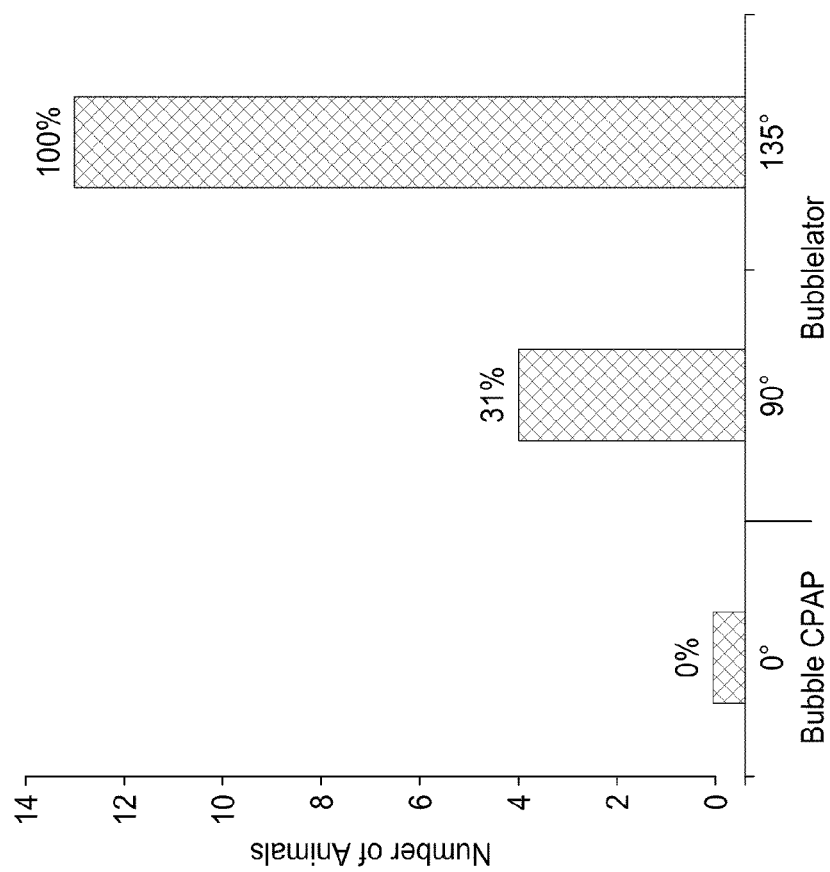
FIG. 20 shows the number of adequately oxygenated paralyzed animals with bubbler angles of 0°, 90° and 135°.

Referring to FIG. 20, all of the animals failed within 60 seconds after being placed on the Bubblelator angled at 0°. The criteria for failure occurs when the arterial blood oxygen saturation of the animal drops below 80%. Setting the Bubblelator to 0° is equivalent to using conventional bubble CPAP, which is a mainstay of therapy in preterm infants. Thus, without spontaneous breathing efforts, standard B-CPAP will not support life in these animals. When the bubbler angle was adjusted to 90° only 4 of the 13 paralyzed rabbits were well oxygenated and ventilated. In 9 of 13 animals the arterial blood oxygen saturation dropped below 80% within 5 minutes and thus reached the failure criteria. However, all of the animals had good gas exchange when placed on the Bubblelator at 135°.

Figure 21:
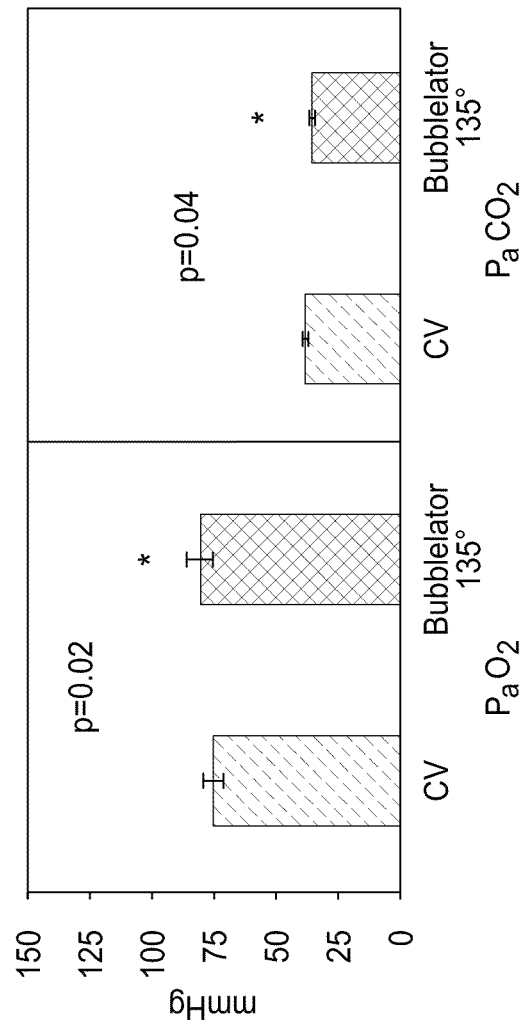
FIG. 21 demonstrates the oxygenation and ventilation characteristics of two different ventilation systems.

Referring now to FIG. 21, the mean airway pressures of the rabbits (while managed on the Bubblelator at 135°) were adjusted to the same level as measured when the rabbits were on CV. Surprisingly, gas exchange (PaO2) was significantly better when the rabbits were managed on the Bubblelator at 135° than while being ventilated with the expensive mechanical CV.

Example 11

Figure 22:
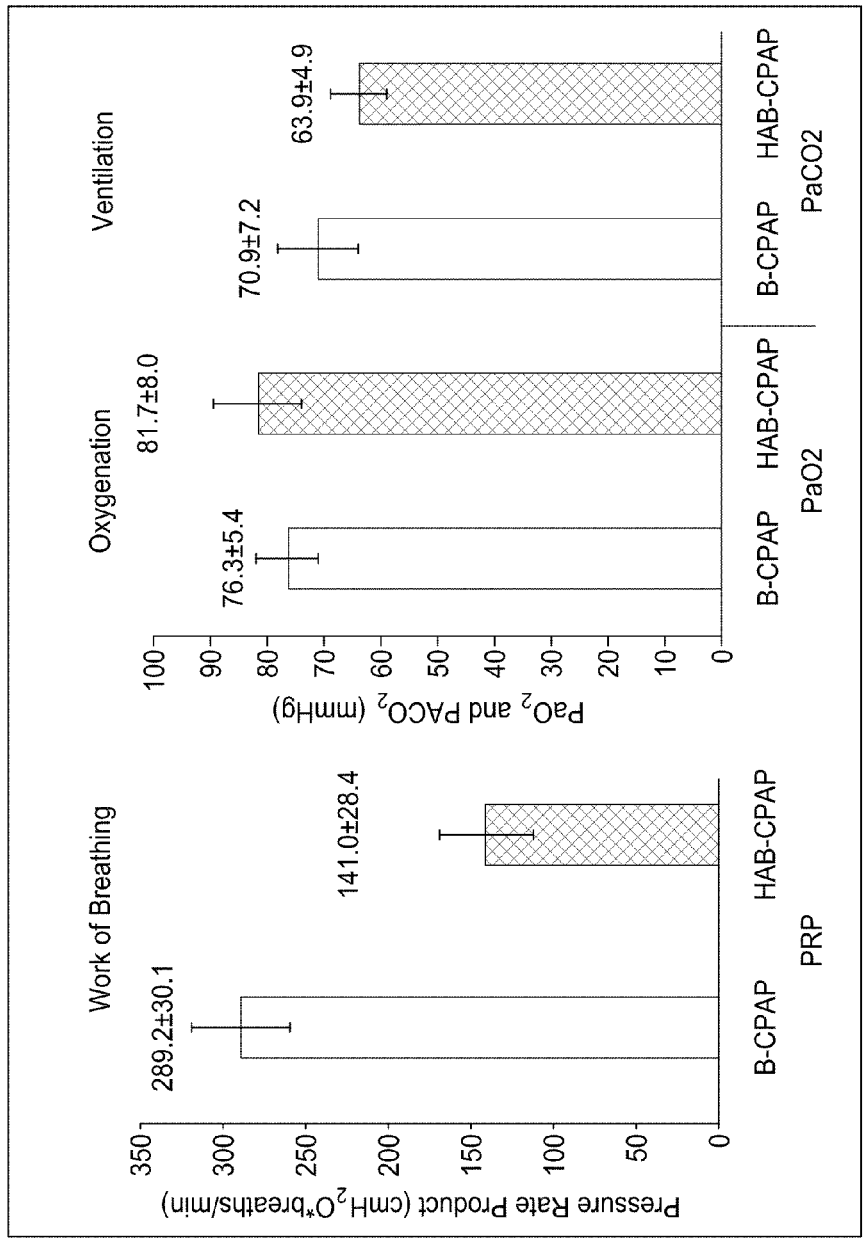
FIG. 22 depicts the work of breathing and the oxygenation and ventilation characteristics of two different ventilation systems.

This example describes how the patient ventilation system of FIG. 1 was evaluated in live animal tests to determine the effectiveness of the ventilation system in comparison to conventional mechanical ventilation with respect to work of breathing, oxygenation and ventilation characteristics. In an experiment, twelve New Zealand White rabbits were used to study the effects of the "Bubbleator" CPAP on "work of breathing" (WOB) as well as oxygenation of arterial blood (PaO2) and removal of carbon dioxide (PaCO2) from arterial blood. The WOB was estimated using the pressure-rate-product (PRP) method. All twelve animals were allowed to breathe spontaneously through nasal prongs placed into the nasal pharynx (similar to manage preterm infants on bubble CPAP). The lungs of the animals were then lavaged using 25 mL/kg 0.9% saline to induce lung injury then they were managed on the two modes of assisted ventilation, conventional bubble CPAP (B-CPAP) set to 0° and High Amplitude Bubble CPAP (HAB-CPAP) set to 135. Gas concentrations and WOB were measured under both conditions, the results of which can be seen in FIG. 22. While breathing on the Bubblelator at 135°, two of the animals ceased spontaneous efforts altogether and a third animal had a greatly reduced WOB. The PaCO2 values of the two apneic animals were 41 and 49 mm Hg suggesting that they were not hyperventilated (35 to 45 mm Hg is considered normal). WOB decreased from 289.2±26.9 (mean±SE) on the Bubblelator at 0° to 141.0±13.1 on the Bubblelator at 135° (p=0.001). The units for PRP are cmH$_2$O times breaths per min. P$_a$O$_2$ values were higher (p=0.007) with the Bubblelator set to 135° (range 49-166 mm Hg) than with the Bubblelator set to 0° (range 51-135 mm Hg). P$_a$CO$_2$ values were not significantly different between the Bubblelator set at 135° and the Bubblelator set at 0° (p=0.073) (70.9±7.2 vs. 63.9±4.9 torr). Thus, oxygenation improved during HAP-CPAP, with comparable ventilation, and reduced WOB. These results indicate that HAB-CPAP may be useful in avoiding intubation and mechanical ventilation of patients in moderate respiratory distress.

Example 12

This example describes how the patient ventilation system of FIG. 29 was evaluated in bench tests to compare the ventilation characteristics of the ventilation system with a common mechanical ventilator. In an experiment, eleven New Zealand White rabbits were used to compare the gas exchange characteristics of the Hansen Ventilator and a conventional mechanical ventilator (CV). The rabbits were sedated, anesthetized and paralyzed so all of the ventilation for gas exchange was supplied by the ventilators, without any spontaneous breathing. The lungs of the animals were lavaged repeatedly with 25 mL/kg of pre-warmed 0.9% saline to produce severe surfactant deficiency. The animals were stabilized with CV and then managed onto the Hansen Ventilator with the same settings as the CV. Arterial blood gas and mean airway pressure measurements were then obtained after ten minutes and paired t-tests were then used to compare values.

Example 13

Figure 31:
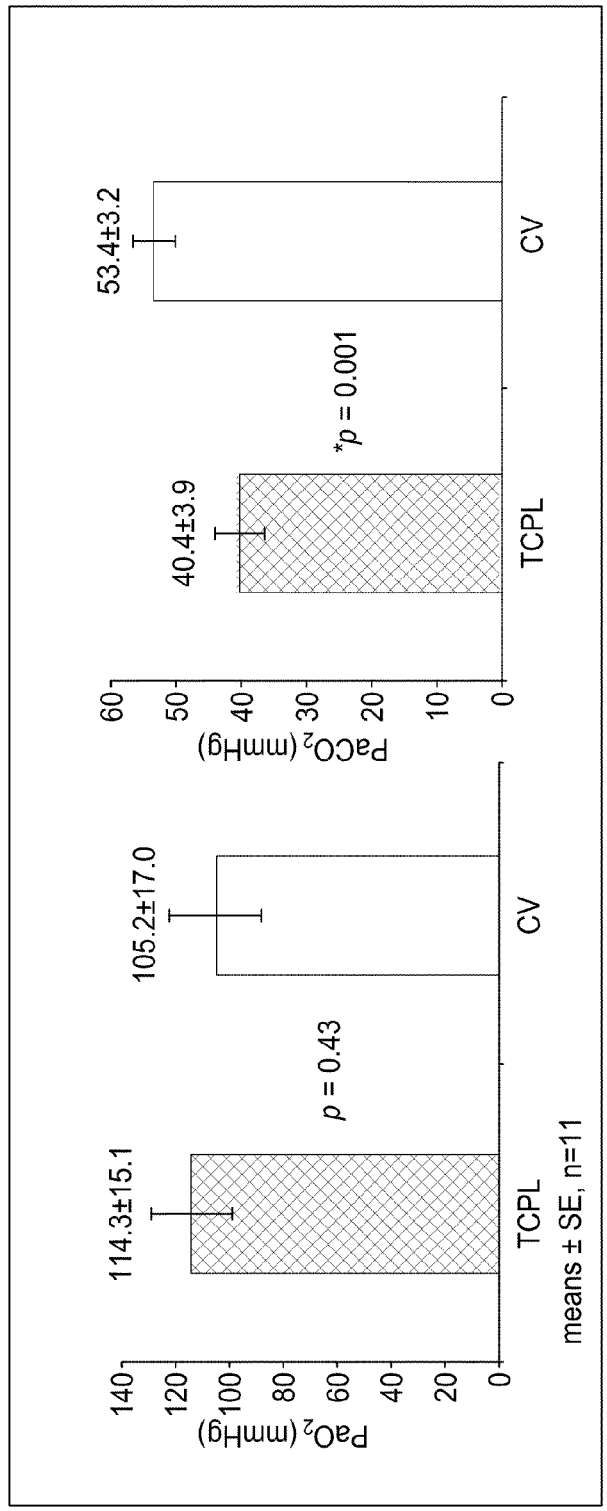
FIG. 31 compares the oxygenation and ventilation characteristics between a conventional ventilator and a Hansen Ventilator.

This example describes how the patient ventilation system of FIG. 29 was evaluated in live animal tests to determine the effectiveness of the ventilation system in comparison to conventional mechanical ventilation with respect to oxygenation and ventilation. FIG. 31 shows the average arterial blood gas results for the animals during ventilation with the Hansen Ventilator and the mechanical ventilator (CV). Note that the Hansen Ventilator (labeled TCPL in FIG. 31 for "time cycled-pressure limited") had improved oxygenation and ventilation, which suggests that the bubbling created by gas exiting the exhalation circuit plays a significant role in ventilation, and may provide additional physiologic advantages in recruiting diseased lung units.

It is to be understood that the detailed description and specific examples, while indicating preferred embodiments of the present invention, are given by way of illustration and not limitation. Many changes and modifications within the scope of the present invention can be made without departing from the spirit thereof, and the invention includes all such modifications.

What is claimed is:

1. A pressure regulating breathing assistance apparatus comprising:
    a pressurized gas source;
    a container comprising fluid; and
    a conduit including proximal and distal ends, the proximal end adapted for connection to the pressurized gas source, the conduit also adapted for connection to a patient interface intermediate the proximal and distal ends, wherein the distal end further comprises:
        (i) at least one peak inspiratory pressure control conduit adapted for connection to the conduit and configured to be submerged in the body of fluid at varying depths;
        (ii) at least one positive end-expiratory pressure control conduit adapted for connection to the conduit and configured to be submerged in the body of fluid at varying depths; and
        (iii) a valve intermediate the at least one peak inspiratory pressure control conduit and the at least one positive end-expiratory pressure control conduit.

2. The pressure regulating breathing assistance apparatus of claim 1, wherein the distal end of the peak inspiratory pressure control conduit or the end-expiratory pressure control conduit is substantially circular having an inside diameter of between 1-3 cm.

3. The pressure regulating breathing assistance apparatus of claim 1, wherein an angled portion of the distal end of the peak inspiratory pressure control conduit or the end-expiratory pressure control conduit has a length of between 12 cm.

4. The pressure regulating breathing assistance apparatus of claim 1, wherein the distal end of the peak inspiratory pressure control conduit or the end-expiratory pressure control conduit is submerged to a depth of between 3-200 cm.

5. The pressure regulating breathing assistance apparatus of claim 1, wherein the fluid has a density of between 0.5-1.5 g/cm3 at 20° C.

6. The pressure regulating breathing assistance apparatus of claim 1, wherein the fluid is water.

7. The pressure regulating breathing assistance apparatus of claim 1, wherein the peak inspiratory pressure control conduit is configured to produce an oscillating pressure wave having more than 50% of its average power spectra occur below about 7 Hz when a bias flow of gas is at least 2 L/min in a model test lung system comprising a hermetically sealed silastic lung within a calibrated plethysmograph.

8. The pressure regulating breathing assistance apparatus of claim 1, wherein the peak inspiratory pressure control conduit is configured to produce an oscillating pressure wave having more than 50% of its average power spectra occur between 2-5 Hz when a bias flow of gas is 2 L/min in a model test lung system comprising a hermetically sealed silastic lung within a calibrated plethysmograph.

9. The pressure regulating breathing assistance apparatus of claim 1, wherein the peak inspiratory pressure control conduit is configured to produce airway pressure oscillation frequencies of between 1-10 Hz when a bias flow of gas is 6 L/min in a model test lung system comprising a hermetically sealed silastic lung within a calibrated plethysmograph.

10. The pressure regulating breathing assistance apparatus of claim 1, wherein the peak inspiratory pressure control conduit is configured to deliver an average volume of gas greater than 3.0 ml when a bias flow of gas is 8 L/min in a model test lung system comprising a hermetically sealed silastic lung within a calibrated plethysmograph.

11. The pressure regulating breathing assistance apparatus of claim 1, further comprising a conduit swivel member at the distal end of the conduit configured to adjust the angle of the distal end of the conduit with respect to a vertical axis defined by gravity and pointing toward the Earth's center of mass, wherein 0 degrees corresponds to the exit portion of the distal end of the conduit being oriented straight down toward the Earth's center of mass, and 180 degrees corresponds to the to the exit portion of the distal end of the conduit being oriented straight UP, away from the Earth's center of mass.

12. The pressure regulating breathing assistance apparatus of claim 1, wherein the distal end of the at least one peak inspiratory pressure control conduit or the at least one positive end-expiratory pressure control conduit has any angle except 0 and 90 degrees with respect to a vertical axis defined by gravity and pointing toward the Earth's center of mass, wherein 0 degrees corresponds to the exit portion of the distal end of the conduit being oriented straight down toward the Earth's center of mass, and 180 degrees corresponds to the to the exit portion of the distal end of the conduit being oriented straight UP, away from the Earth's center of mass, wherein the pressure regulating breathing assistance apparatus is configured to produce a high amplitude, low frequency broadband oscillating pressure wave having more than 50% of its average power spectra occur below 7 Hz when a bias gas flow is at least 2 L/min in a model test lung system comprising a hermetically sealed silastic lung within a calibrated plethysmograph.

13. The pressure regulating breathing assistance apparatus of claim 1, wherein the distal end of the positive end-expiratory pressure control conduit is angled greater than 90 degrees with respect to a vertical axis defined by gravity and pointing toward the Earth's center of mass, wherein 0 degrees corresponds to the exit portion of the distal end of the conduit being oriented straight down toward the Earth's center of mass, and 180 degrees corresponds to the to the exit portion of the distal end of the conduit being oriented straight UP, away from the Earth's center of mass.

14. The pressure regulating breathing assistance apparatus of claim 13, wherein the distal end of the peak inspiratory pressure control conduit or the end-expiratory pressure control conduit is angled between 91-170 degrees with respect to a vertical axis defined by gravity and pointing toward the Earth's center of mass, wherein 0 degrees corresponds to the exit portion of the distal end of the conduit being oriented straight down toward the Earth's center of mass, and 180 degrees corresponds to the to the exit portion of the distal end of the conduit being oriented straight UP, away from the Earth's center of mass.

15. The pressure regulating breathing assistance apparatus of claim 14, wherein the distal end of the peak inspiratory pressure control conduit or the end-expiratory pressure control conduit is angled to 135 degrees with respect to a vertical axis defined by gravity and pointing toward the Earth's center of mass, wherein 0 degrees corresponds to the exit portion of the distal end of the conduit being oriented straight down toward the Earth's center of mass, and 180 degrees corresponds to the to the exit portion of the distal end of the conduit being oriented straight UP, away from the Earth's center of mass.

16. The pressure regulating breathing assistance apparatus of claim 12, wherein the distal end of the peak inspiratory pressure control conduit or the end-expiratory pressure control conduit is substantially circular having an inside diameter of between 1-3 cm.

17. The pressure regulating breathing assistance apparatus of claim 12, wherein the angled portion of the distal end of the peak inspiratory pressure control conduit or the end-expiratory pressure control conduit has a length of between 5-12 cm.

18. The pressure regulating breathing assistance apparatus of claim 12, wherein the distal end of the peak inspiratory pressure control conduit or the end-expiratory pressure control conduit is submerged to a depth of about between 3-200 cm.

19. The pressure regulating breathing assistance apparatus of claim 12, wherein the fluid has a density of between about 0.5-1.5 g/cm3 at 20° C.

20. The pressure regulating breathing assistance apparatus of claim 12, wherein the fluid is water.

21. The pressure regulating breathing assistance apparatus of claim 12, wherein the peak inspiratory pressure control conduit is configured to produce an oscillating pressure wave having more than 50% of its average power spectra occur below 7 Hz when a bias flow of gas is at least 2 L/min in a model test lung system comprising a hermetically sealed silastic lung within a calibrated plethysmograph.

22. The pressure regulating breathing assistance apparatus of claim 12, wherein the peak inspiratory pressure control conduit is configured to produce an oscillating pressure wave having more than 50% of its average power spectra occur between about 2-5 Hz when a bias flow of gas is 2 L/min in a model test lung system comprising a hermetically sealed silastic lung within a calibrated plethysmograph.

23. The pressure regulating breathing assistance apparatus of claim 12, wherein the peak inspiratory pressure control conduit is configured to produce airway pressure oscillation frequencies of between 1-10 Hz when a bias flow of gas is 6 L/min in a model test lung system comprising a hermetically sealed silastic lung within a calibrated plethysmograph.

24. The pressure regulating breathing assistance apparatus of claim 12, wherein the peak inspiratory pressure control conduit is configured to deliver an average volume of gas greater than 3.0 ml when a bias flow of gas is 8 L/min in a model test lung system comprising a hermetically sealed silastic lung within a calibrated plethysmograph.

25. The pressure regulating breathing assistance apparatus of claim 11, wherein the conduit swivel member further comprises a plurality of marks that indicate the angle of the distal end of said conduit with respect to the vertical axis.

26. The pressure regulating breathing assistance apparatus of claim 11, wherein the conduit swivel member is automated such that a user can manually or automatically adjust the angle of said distal end of said conduit with respect to the vertical axis.

27. The pressure regulating breathing assistance apparatus of claim 26, further comprising a computer configured to operate said swivel member upon user instruction and thereby automatically adjust the angle of said distal end of said conduit with respect to the vertical axis.

28. A method for providing continuous positive airway pressure with oscillating positive end-expiratory pressure to a subject, comprising:
   providing the pressure regulating breathing assistance apparatus as set forth in claim 1;
   releasing gas from said pressurized gas source into said conduit of said pressure regulating breathing assistance apparatus; and
   delivering said gas to said subject.

29. A method for providing continuous positive airway pressure with oscillating positive end-expiratory pressure to a subject, comprising:
   providing the pressure regulating breathing assistance apparatus as set forth in claim 12;
   releasing gas from said pressurized gas source into said conduit of said pressure regulating breathing assistance apparatus; and
   delivering said gas to said subject.

30. The pressure regulating breathing assistance apparatus of claim 1, wherein the distal end of the peak inspiratory pressure control conduit or the end-expiratory pressure control conduit is substantially circular having an inside diameter of between 1.2-2.0 cm.

31. The pressure regulating breathing assistance apparatus of claim 1, wherein the distal end of the peak inspiratory pressure control conduit or the end-expiratory pressure control conduit is substantially circular having an inside diameter of between about 1.3-1.8 cm.

32. The pressure regulating breathing assistance apparatus of claim 1, wherein the distal end of the peak inspiratory pressure control conduit or the end-expiratory pressure control conduit is substantially circular having an inside diameter of between 1.4-1.6 cm.

33. The pressure regulating breathing assistance apparatus of claim 1, wherein an angled portion of the distal end of the peak inspiratory pressure control conduit or the end-expiratory pressure control conduit has a length of between 6-11 cm.

34. The pressure regulating breathing assistance apparatus of claim 1, wherein an angled portion of the distal end of the peak inspiratory pressure control conduit or the end-expiratory pressure control conduit has a length of between 7-10 cm.

35. The pressure regulating breathing assistance apparatus of claim 1, wherein an angled portion of the distal end of the peak inspiratory pressure control conduit or the end-expiratory pressure control conduit has a length of between 8-9.5 cm.

36. The pressure regulating breathing assistance apparatus of claim 1, wherein the distal end of the peak inspiratory pressure control conduit or the end-expiratory pressure control conduit is submerged to a depth of between 5-11 cm.

37. The pressure regulating breathing assistance apparatus of claim 1, wherein the distal end of the peak inspiratory pressure control conduit or the end-expiratory pressure control conduit is submerged to a depth of 5 cm, 7 cm, 9 cm, or 11 cm.

38. The pressure regulating breathing assistance apparatus of claim 1, wherein the peak inspiratory pressure control conduit is configured to produce an oscillating pressure wave having more than 50% of its average power spectra occur between 1-9 Hz when a bias flow of gas is 12 L/min in a model test lung system comprising a hermetically sealed silastic lung within a calibrated plethysmograph.

39. The pressure regulating breathing assistance apparatus of claim 1, wherein the peak inspiratory pressure control conduit is configured to produce airway pressure oscillation frequencies of between 2-9 Hz when a bias flow of gas is 6 L/min in a model test lung system comprising a hermetically sealed silastic lung within a calibrated plethysmograph.

40. The pressure regulating breathing assistance apparatus of claim 1, wherein the peak inspiratory pressure control conduit is configured to produce airway pressure oscillation frequencies of between 2-7 Hz when a bias flow of gas is 6 L/min in a model test lung system comprising a hermetically sealed silastic lung within a calibrated plethysmograph.

41. The pressure regulating breathing assistance apparatus of claim 1, wherein the peak inspiratory pressure control conduit is configured to produce airway pressure oscillation frequencies of between 2-5 Hz when a bias flow of gas is 6 L/min in a model test lung system comprising a hermetically sealed silastic lung within a calibrated plethysmograph.

42. The pressure regulating breathing assistance apparatus of claim 1, wherein the distal end of the peak inspiratory pressure control conduit or the end-expiratory pressure control conduit is angled between 95-165 degrees with respect to a vertical axis defined by gravity and pointing toward the Earth's center of mass, wherein 0 degrees corresponds to the exit portion of the distal end of the conduit being oriented straight down toward the Earth's center of mass, and 180 degrees corresponds to the to the exit portion of the distal end of the conduit being oriented straight up, away from the Earth's center of mass.

43. The pressure regulating breathing assistance apparatus of claim 1, wherein the distal end of the peak inspiratory pressure control conduit or the end-expiratory pressure control conduit is angled between 100-160 degrees with respect to a vertical axis defined by gravity and pointing toward the Earth's center of mass, wherein 0 degrees corresponds to the exit portion of the distal end of the conduit being oriented straight down toward the Earth's center of mass, and 180 degrees corresponds to the to the exit portion of the distal end of the conduit being oriented straight up, away from the Earth's center of mass.

44. The pressure regulating breathing assistance apparatus of claim 1, wherein the distal end of the peak inspiratory pressure control conduit or the end-expiratory pressure control conduit is angled between 105-155 degrees with respect to a vertical axis defined by gravity and pointing toward the Earth's center of mass, wherein 0 degrees corresponds to the exit portion of the distal end of the conduit being oriented straight down toward the Earth's center of mass, and 180 degrees corresponds to the to the exit portion of the distal end of the conduit being oriented straight up, away from the Earth's center of mass.

45. The pressure regulating breathing assistance apparatus of claim 1, wherein the distal end of the peak inspiratory pressure control conduit or the end-expiratory pressure control conduit is angled between 110-150 degrees with respect to a vertical axis defined by gravity and pointing toward the Earth's center of mass, wherein 0 degrees corresponds to the exit portion of the distal end of the conduit being oriented straight down toward the Earth's center of mass, and 180 degrees corresponds to the to the exit portion of the distal end of the conduit being oriented straight up, away from the Earth's center of mass.

46. The pressure regulating breathing assistance apparatus of claim 1, wherein the distal end of the peak inspiratory pressure control conduit or the end-expiratory pressure control conduit is angled between 115-145 degrees with respect to a vertical axis defined by gravity and pointing toward the Earth's center of mass, wherein 0 degrees corresponds to the exit portion of the distal end of the conduit being oriented straight down toward the Earth's center of mass, and 180 degrees corresponds to the to the exit portion of the distal end of the conduit being oriented straight up, away from the Earth's center of mass.

47. The pressure regulating breathing assistance apparatus of claim 1, wherein the distal end of the peak inspiratory pressure control conduit or the end-expiratory pressure control conduit is angled between 120-140 degrees with respect to a vertical axis defined by gravity and pointing toward the Earth's center of mass, wherein 0 degrees corresponds to the exit portion of the distal end of the conduit being oriented straight down toward the Earth's center of mass, and 180 degrees corresponds to the to the exit portion of the distal end of the conduit being oriented straight up, away from the Earth's center of mass.

48. The pressure regulating breathing assistance apparatus of claim 1, wherein the distal end of the peak inspiratory pressure control conduit or the end-expiratory pressure control conduit is angled between 125-135 degrees with respect to a vertical axis defined by gravity and pointing toward the Earth's center of mass, wherein 0 degrees corresponds to the exit portion of the distal end of the conduit being oriented straight down toward the Earth's center of mass, and 180 degrees corresponds to the to the exit portion of the distal end of the conduit being oriented straight up, away from the Earth's center of mass.

49. The pressure regulating breathing assistance apparatus of claim 1, wherein the distal end of the peak inspiratory pressure control conduit or the end-expiratory pressure control conduit is angled between 130-140 degrees with respect to a vertical axis defined by gravity and pointing toward the Earth's center of mass, wherein 0 degrees corresponds to the exit portion of the distal end of the conduit being oriented straight down toward the Earth's center of mass, and 180 degrees corresponds to the to the exit portion of the distal end of the conduit being oriented straight up, away from the Earth's center of mass.

50. The pressure regulating breathing assistance apparatus of claim 12, wherein the distal end of the peak inspiratory pressure control conduit or the end-expiratory pressure control conduit is substantially circular having an inside diameter of between 1.2-2.0 cm.

51. The pressure regulating breathing assistance apparatus of claim 12, wherein the distal end of the peak inspiratory pressure control conduit or the end-expiratory pressure control conduit is substantially circular having an inside diameter of between 1.3-1.8 cm.

52. The pressure regulating breathing assistance apparatus of claim 12, wherein the distal end of the peak inspiratory pressure control conduit or the end-expiratory pressure control conduit is substantially circular having an inside diameter of between 1.4-1.6 cm.

53. The pressure regulating breathing assistance apparatus of claim 12, wherein the angled portion of the distal end of the peak inspiratory pressure control conduit or the end-expiratory pressure control conduit has a length of between 6-11 cm.

54. The pressure regulating breathing assistance apparatus of claim 12, wherein the angled portion of the distal end of the peak inspiratory pressure control conduit or the end-expiratory pressure control conduit has a length of between 7-10 cm.

55. The pressure regulating breathing assistance apparatus of claim 12, wherein the angled portion of the distal end of the peak inspiratory pressure control conduit or the end-expiratory pressure control conduit has a length of between 8-9.5 cm.

56. The pressure regulating breathing assistance apparatus of claim 12, wherein the distal end of the peak inspiratory pressure control conduit or the end-expiratory pressure control conduit is submerged to a depth of between 5-11 cm.

57. The pressure regulating breathing assistance apparatus of claim 12, wherein the distal end of the peak inspiratory pressure control conduit or the end-expiratory pressure control conduit is submerged to a depth of 5 cm, 7 cm, 9 cm, or 11 cm.

58. The pressure regulating breathing assistance apparatus of claim 12, wherein the peak inspiratory pressure control conduit is configured to produce an oscillating pressure wave having more than 50% of its average power spectra occur between 1-9 Hz when a bias flow of gas is 12 L/min in a model test lung system comprising a hermetically sealed silastic lung within a calibrated plethysmograph.

59. The pressure regulating breathing assistance apparatus of claim 12, wherein the peak inspiratory pressure control conduit is configured to produce airway pressure oscillation frequencies of between 2-9 Hz, when a bias flow of gas is 6 L/min in a model test lung system comprising a hermetically sealed silastic lung within a calibrated plethysmograph.

60. The pressure regulating breathing assistance apparatus of claim 12, wherein the peak inspiratory pressure control conduit is configured to produce airway pressure oscillation frequencies of between 2-7 Hz when a bias flow of gas is 6 L/min in a model test lung system comprising a hermetically sealed silastic lung within a calibrated plethysmograph.

61. The pressure regulating breathing assistance apparatus of claim 12, wherein the peak inspiratory pressure control conduit is configured to produce airway pressure oscillation frequencies of between 2-5 Hz when a bias flow of gas is 6 L/min in a model test lung system comprising a hermetically sealed silastic lung within a calibrated plethysmograph.

* * * * *

UNITED STATES PATENT AND TRADEMARK OFFICE
CERTIFICATE OF CORRECTION

| | | |
|---|---|---|
| PATENT NO. | : 8,499,759 B2 | |
| APPLICATION NO. | : 12/899177 | |
| DATED | : August 6, 2013 | |
| INVENTOR(S) | : Robert M. DiBlasi et al. | |

It is certified that error appears in the above-identified patent and that said Letters Patent is hereby corrected as shown below:

On the title page, item (73), Assignee, please delete "Seattle Children's Hospital" and insert therefore --Seattle Children's Hospital d/b/a Seattle Children's Research Institute--.

In the Specification

In column 10, Line 3 Change "of the of the" to --of the--.

In column 18, Line 48 Change "2° C." to --20° C.--.

In the Claims

In column 30, Line 22 In Claim 3, change "12 cm." to --5-12 cm.--.

In column 30, Line 65-66 In Claim 11, change "to the to the" to --to the--.

In column 30, Line 67 In Claim 11, change "UP," to --up,--.

In column 31, Line 9-10 In Claim 12, change "to the to the" to --to the--.

In column 31, Line 11 In Claim 12, change "UP," to --up,--.

In column 31, Line 27 In Claim 13, change "to the to the" to --to the--.

In column 31, Line 28 In Claim 13, change "UP," to --up,--.

In column 31, Line 39 In Claim 14, change "to the to the" to --to the--.

Signed and Sealed this
Seventeenth Day of February, 2015

Michelle K. Lee
*Deputy Director of the United States Patent and Trademark Office*

CERTIFICATE OF CORRECTION (continued)
U.S. Pat. No. 8,499,759 B2

In column 31, Line 40 In Claim 14, change "UP," to --up,--.

In column 31, Line 50 In Claim 15, change "to the to the" to --to the--.

In column 31, Line 51 In Claim 15, change "UP," to --up,--.

In column 34, Line 4 In Claim 42, change "to the to the" to --to the--.

In column 34, Line 15 In Claim 43, change "to the to the" to --to the--.

In column 34, Line 26 In Claim 44, change "to the to the" to --to the--.

In column 34, Line 37 In Claim 45, change "to the to the" to --to the--.

In column 34, Line 48 In Claim 46, change "to the to the" to --to the--.

In column 34, Line 59 In Claim 47, change "to the to the" to --to the--.

In column 35, Line 3 In Claim 48, change "to the to the" to --to the--.

In column 35, Line 13 In Claim 49, change "to the to the" to --to the--.